US011685928B2

(12) United States Patent
Lanquar et al.

(10) Patent No.: US 11,685,928 B2
(45) **Date of Patent: *Jun. 27, 2023**

(54) RECOMBINANT FUSION PROTEINS FOR PRODUCING MILK PROTEINS IN PLANTS

(71) Applicant: Nobell Foods, Inc., South San Francisco, CA (US)

(72) Inventors: Viviane Lanquar, San Carlos, CA (US); Magi El-Richani, San Francisco, CA (US)

(73) Assignee: Nobell Foods, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/851,624

(22) Filed: Jun. 28, 2022

(65) Prior Publication Data

US 2022/0372504 A1 Nov. 24, 2022

Related U.S. Application Data

(60) Continuation of application No. 17/374,125, filed on Jul. 13, 2021, now Pat. No. 11,401,526, which is a division of application No. 17/157,105, filed on Jan. 25, 2021, now Pat. No. 11,072,797, which is a continuation of application No. 17/039,759, filed on Sep. 30, 2020, now Pat. No. 10,947,552.

(51) Int. Cl.
*C12N 15/82* (2006.01)
*A01G 22/40* (2018.01)

(52) U.S. Cl.
CPC ......... *C12N 15/8251* (2013.01); *A01G 22/40* (2018.02)

(58) Field of Classification Search
CPC .................................................. C12N 15/8251
USPC .......................................................... 800/312
See application file for complete search history.

(56) References Cited

U.S. PATENT DOCUMENTS 4,518,616 A 5/1985 Czulak
5,068,118 A 11/1991 Strandholm
5,650,554 A 7/1997 Moloney
5,741,957 A 4/1998 Deboer et al.
5,767,366 A 6/1998 Sathasivan et al.
5,891,433 A 4/1999 Silver
5,959,171 A 9/1999 Hyttinen et al.
5,968,830 A 10/1999 Dan et al.
6,100,447 A 8/2000 Wu et al.
6,127,145 A 10/2000 Sutliff et al.
6,222,094 B1 4/2001 Hansson et al.
6,225,105 B1 5/2001 Sathasivan et al.
6,245,974 B1 6/2001 Michalowski et al.
6,388,066 B1 5/2002 Bruce et al.
6,455,759 B1 9/2002 Vierstra et al.
6,569,831 B1 5/2003 Legrand et al.
6,642,437 B1 11/2003 Lemaux et al.
6,781,044 B2 8/2004 Rodriguez et al.
6,991,824 B2 1/2006 Huang et al.
7,138,150 B2 11/2006 Huang et al.
7,157,629 B2 1/2007 Cho et al.
7,217,858 B2 5/2007 Falco et al.
7,270,989 B2 9/2007 Kappeler et al.
7,304,208 B2 12/2007 Huang et al.
7,354,902 B2 4/2008 Legrand et al.
7,365,240 B2 4/2008 Verbsky et al.
7,390,936 B1 6/2008 Van Rooijen et al.
7,417,178 B2 8/2008 Huang et al.
7,428,875 B2 9/2008 Orvar
7,501,265 B1 3/2009 Moloney et al.
7,531,325 B2 5/2009 Van Rooijen et al.
7,575,898 B2 8/2009 Ludevid et al.
7,589,252 B2 9/2009 Huang et al.
7,718,851 B2 5/2010 Huang et al.
7,854,952 B2 12/2010 Carr et al.
7,960,614 B2 6/2011 Chang et al.
8,017,400 B2 9/2011 Toriyama et al.
8,158,857 B2 4/2012 Huang et al.
8,163,880 B2 4/2012 Heifetz et al.
8,273,954 B1 9/2012 Rogers et al.
8,293,533 B2 10/2012 Falco et al.
8,334,139 B1 12/2012 Fraley et al.
8,334,254 B2 12/2012 Legrand et al.
8,362,317 B2 1/2013 Calabotta et al.
8,609,416 B2 12/2013 Barnett
8,637,316 B2 1/2014 Migiwa et al.
8,686,225 B2 4/2014 Huang et al.
8,802,825 B2 8/2014 Ludevid M Gica et al.
8,809,630 B2 8/2014 Kumimoto et al.
8,822,181 B2 9/2014 Torrent et al.

(Continued)

FOREIGN PATENT DOCUMENTS

EP 3202899 A1 8/2017
EP 1957110 B1 9/2020
EP 3069123 B1 9/2020
EP 3702463 A1 9/2020
EP 3708565 A1 9/2020

(Continued)

OTHER PUBLICATIONS

US 11,071,315 B2, 07/2021, Varadan (withdrawn)
Altschul et al., "Basic Local Alignment Search Tool," J. Mol. Biol. (1990) 215:403-410.
Altschul et al., "Gapped BLAST and PSI-BLAST: a new generation of protein database search programs," Nucleic Acids Research (1997) 25(17):3389-3402.

(Continued)

*Primary Examiner* — Li Zheng
(74) *Attorney, Agent, or Firm* — Cooley LLP

(57) ABSTRACT

Provided herein are compositions and methods for producing milk proteins in plants, which allow for safe, sustainable and humane production of milk proteins for commercial use, such as use in food compositions. The disclosure provides recombinant fusion proteins comprising a milk protein, or fragment thereof and a structured mammalian, avian, plant, or fungal protein, or fragment thereof. The disclosure also provides methods for producing the recombinant fusions proteins, and food compositions comprising the same.

16 Claims, 9 Drawing Sheets

Specification includes a Sequence Listing.

(56) References Cited

U.S. PATENT DOCUMENTS 8,927,809 B2 1/2015 Meyer et al.
9,006,513 B2 4/2015 Calabotta et al.
9,011,949 B2 4/2015 Brown et al.
9,024,114 B2 5/2015 Carlson et al.
9,321,828 B2 4/2016 Zhang et al.
9,555,097 B2 1/2017 Rybicki et al.
9,637,751 B2 5/2017 Ludevid M Gica et al.
9,650,640 B2 5/2017 Kumar et al.
9,700,067 B2 7/2017 Fraser et al.
9,700,071 B2 7/2017 Silver et al.
9,725,731 B2 8/2017 Abbitt
9,737,875 B2 8/2017 Brown et al.
9,738,694 B2 8/2017 Yeo et al.
9,790,512 B2 10/2017 Calabotta et al.
9,808,029 B2 11/2017 Fraser et al.
9,826,772 B2 11/2017 Fraser et al.
9,833,768 B2 12/2017 Brown et al.
9,924,728 B2 3/2018 Pandya et al.
9,938,327 B2 4/2018 Shankar et al.
9,943,096 B2 4/2018 Fraser et al.
10,039,306 B2 8/2018 Vrljic et al.
10,087,434 B2 10/2018 Kale et al.
10,093,913 B2 10/2018 Kale et al.
10,106,806 B2 10/2018 Ko et al.
10,125,373 B2 11/2018 Mason et al.
10,172,380 B2 1/2019 Varadan et al.
10,172,381 B2 1/2019 Vrljic et al.
10,273,492 B2 4/2019 Shankar et al.
10,287,568 B2 5/2019 Kale et al.
10,294,485 B2 5/2019 Gupta et al.
10,314,325 B2 6/2019 Fraser et al.
10,327,464 B2 6/2019 Fraser et al.
10,595,545 B2 3/2020 Pandya et al.
10,618,951 B1 4/2020 Pettit et al.
10,689,656 B2 6/2020 Shankar et al.
10,757,955 B2 9/2020 Yang et al.
10,759,758 B2 9/2020 Thaler et al.
10,760,062 B2 9/2020 Naesby et al.
10,765,116 B2 9/2020 Kausch-Busies et al.
10,765,125 B2 9/2020 Gunes et al.
10,765,318 B2 9/2020 Hockings
10,768,169 B2 9/2020 Rezzi et al.
10,772,332 B2 9/2020 Mosrin et al.
10,781,263 B2 9/2020 Kahnert et al.
10,781,427 B2 9/2020 Barouch et al.
10,781,432 B1 9/2020 Cameron et al.
10,785,976 B2 9/2020 Vandock et al.
10,785,977 B2 9/2020 Vandock et al.
10,793,850 B2 10/2020 Wiessenhaan et al.
10,793,872 B2 10/2020 Poree et al.
10,798,958 B2 10/2020 Varadan et al.
10,798,963 B2 10/2020 Maynard et al.
10,801,045 B2 10/2020 Fischer et al.
10,806,170 B2 10/2020 Braun
10,806,699 B2 10/2020 Burbidge et al.
10,807,968 B2 10/2020 Jansen et al.
10,815,500 B2 10/2020 Juillerat et al.
10,815,514 B2 10/2020 Olsson et al.
10,863,761 B2 12/2020 Brown et al.
10,870,861 B2 12/2020 Noda et al.
10,894,812 B1 * 1/2021 Lanquar ............. C12N 15/8257
10,947,552 B1 * 3/2021 Lanquar ............. C07K 14/4717
10,981,974 B2 4/2021 Pettit et al.
10,986,848 B2 4/2021 Holz-Schietinger et al.
10,988,521 B1 * 4/2021 Lanquar ............. C07K 14/4717
10,993,462 B2 5/2021 Vrljic et al.
11,013,250 B2 5/2021 Vrljic et al.
11,034,743 B1 * 6/2021 Lanquar ............... C12N 9/6483
11,051,532 B2 7/2021 Henderson, Jr. et al.
11,072,797 B1 * 7/2021 Lanquar ............. C07K 14/4732
11,076,615 B2 8/2021 Pandya et al.
11,142,555 B1 * 10/2021 Lanquar ............. C12N 15/8257
11,160,299 B2 11/2021 Mahadevan et al.
11,219,232 B2 1/2022 Fraser et al.
11,224,241 B2 1/2022 Fraser et al.
11,326,176 B2 5/2022 Tobin
11,401,526 B2 * 8/2022 Lanquar ............. C12N 15/8251
2002/0002714 A1 1/2002 Ikegami et al.
2002/0073448 A1 6/2002 Michalowski et al.
2002/0108149 A1 8/2002 Gruis et al.
2002/0155998 A1 10/2002 Young et al.
2002/0192813 A1 12/2002 Conner et al.
2003/0044503 A1 3/2003 Morgan et al.
2003/0056244 A1 3/2003 Huang et al.
2003/0074700 A1 4/2003 Huang et al.
2003/0166162 A1 9/2003 Van Rooijen et al.
2003/0172403 A1 9/2003 Huang et al.
2003/0221223 A1 11/2003 Huang et al.
2003/0229925 A1 12/2003 Legrand et al.
2004/0022918 A1 2/2004 McCarthy et al.
2004/0023257 A1 2/2004 Barton et al.
2004/0063617 A1 4/2004 Huang et al.
2004/0078851 A1 4/2004 Huang et al.
2004/0088754 A1 5/2004 Cho et al.
2004/0111766 A1 6/2004 Huang et al.
2004/0143857 A1 7/2004 Young et al.
2004/0241791 A1 12/2004 Edens et al.
2005/0158832 A1 7/2005 Young et al.
2005/0181482 A1 8/2005 Meade et al.
2005/0229273 A1 10/2005 Huang et al.
2005/0283854 A1 12/2005 Krumm et al.
2007/0150976 A1 6/2007 Yang et al.
2008/0010697 A1 1/2008 Yang et al.
2008/0029003 A1 2/2008 Orvar
2008/0050503 A1 2/2008 Huang et al.
2008/0092252 A1 4/2008 Cammue et al.
2008/0313776 A1 12/2008 Li
2008/0318277 A1 12/2008 Huang et al.
2009/0023212 A1 1/2009 Zhong et al.
2009/0133159 A1 5/2009 Li
2009/0156486 A1 6/2009 Huang et al.
2009/0258004 A1 10/2009 Huang et al.
2010/0003235 A1 1/2010 Hagie et al.
2010/0015713 A1 1/2010 Deeter et al.
2010/0031394 A1 2/2010 Huang et al.
2010/0064383 A1 3/2010 Bogs et al.
2010/0119691 A1 5/2010 Huang et al.
2010/0183589 A1 7/2010 Huang et al.
2010/0223682 A1 9/2010 Katz et al.
2010/0329995 A1 12/2010 Deeter et al.
2011/0092411 A1 4/2011 Legrand et al.
2011/0117131 A1 5/2011 Huang et al.
2011/0189751 A1 8/2011 Barnett
2011/0243975 A1 10/2011 Terakawa et al.
2011/0302672 A1 12/2011 Merlo et al.
2012/0088729 A1 4/2012 Zhang et al.
2012/0195883 A1 8/2012 Huang et al.
2012/0208198 A1 8/2012 Bogs et al.
2012/0315697 A1 12/2012 Pettit et al.
2013/0129899 A1 5/2013 Ummadi et al.
2013/0157356 A1 6/2013 Barnett et al.
2013/0340114 A1 12/2013 Albert et al.
2014/0237688 A1 8/2014 Chang et al.
2015/0080296 A1 3/2015 Silver et al.
2015/0087532 A1 3/2015 Brown et al.
2015/0150822 A1 6/2015 Perumal et al.
2015/0197764 A1 7/2015 Aasen et al.
2015/0203530 A1 7/2015 Yang et al.
2015/0289541 A1 10/2015 Brown et al.
2015/0299726 A1 10/2015 Mcelver et al.
2015/0305361 A1 10/2015 Holz-Schietinger et al.
2015/0305390 A1 10/2015 Vrljic et al.
2015/0351435 A1 12/2015 Fraser et al.
2015/0361446 A1 12/2015 Beatty et al.
2015/0361447 A1 12/2015 Beatty et al.
2015/0366233 A1 12/2015 Brown et al.
2016/0076048 A1 3/2016 Zhang et al.
2016/0160232 A1 6/2016 Ruiter et al.
2016/0213766 A1 7/2016 Huang et al.
2016/0220622 A1 8/2016 Park et al.
2016/0222054 A1 8/2016 Brown et al.
2016/0298129 A1 10/2016 Ruiter et al.
2016/0340411 A1 11/2016 Fraser et al.
2016/0369291 A1 12/2016 Mayfield et al.

(56) References Cited

U.S. PATENT DOCUMENTS

2017/0081676 A1 3/2017 Gupta et al.
2017/0112175 A1 4/2017 Fraser et al.
2017/0164632 A1 6/2017 Pandya et al.
2017/0172169 A1 6/2017 Grzanich et al.
2017/0188612 A1 7/2017 Varadan et al.
2017/0273328 A1 9/2017 Pandya et al.
2017/0290363 A1 10/2017 Fraser et al.
2017/0295833 A1 10/2017 Fraser et al.
2017/0298337 A1 10/2017 Kale et al.
2017/0320041 A1 11/2017 Brown et al.
2017/0321203 A1 11/2017 Kale et al.
2017/0321204 A1 11/2017 Kale et al.
2017/0342131 A1 11/2017 Fraser et al.
2017/0342132 A1 11/2017 Fraser et al.
2017/0349637 A1 12/2017 Shankar et al.
2017/0349906 A1 12/2017 Shankar et al.
2018/0027851 A1 2/2018 Vrljic et al.
2018/0127764 A1 5/2018 Shankar et al.
2018/0142248 A1 5/2018 Martin-Ortigosa et al.
2018/0168209 A1 6/2018 Fraser et al.
2018/0192680 A1 7/2018 Fraser et al.
2018/0195081 A1 7/2018 Shintaku et al.
2018/0199605 A1 7/2018 Fraser et al.
2018/0199606 A1 7/2018 Fraser et al.
2018/0237793 A1 8/2018 Aasen et al.
2018/0243408 A1 8/2018 Fanger et al.
2018/0250369 A1 9/2018 Macmanus et al.
2018/0271111 A1 9/2018 Pandya et al.
2018/0291392 A1 10/2018 El-Richani et al.
2018/0371469 A1 12/2018 Shankar et al.
2019/0008192 A1 1/2019 Brown et al.
2019/0032066 A1 1/2019 Noda et al.
2019/0040404 A1 2/2019 Gupta et al.
2019/0048330 A1 2/2019 Aharoni et al.
2019/0062766 A1 2/2019 Hamada et al.
2019/0070287 A1 3/2019 Fanger et al.
2019/0116855 A1 4/2019 Vrljic et al.
2019/0133162 A1 5/2019 Varadan et al.
2019/0133163 A1 5/2019 Varadan et al.
2019/0200658 A1 7/2019 Vrljic et al.
2019/0203214 A1 7/2019 Sorokin et al.
2019/0216106 A1 7/2019 Geistlinger et al.
2019/0292217 A1 9/2019 Davis et al.
2019/0292555 A1 9/2019 Davis et al.
2019/0336595 A1 11/2019 Ciaramella
2019/0336596 A1 11/2019 Mason et al.
2020/0123556 A1 4/2020 El-Richani et al.
2020/0138066 A1 5/2020 Anchel
2020/0172584 A1 6/2020 Fishman et al.
2020/0247871 A1 8/2020 Pettit et al.
2020/0268026 A1 8/2020 Khare et al.
2020/0268027 A1 8/2020 Gaspard et al.
2020/0269161 A1 8/2020 Kompala
2020/0275660 A1 9/2020 Sudau et al.
2020/0275674 A1 9/2020 Napolitano et al.
2020/0277202 A1 9/2020 Patey
2020/0277588 A1 9/2020 Cameron et al.
2020/0277631 A1 9/2020 Doudna et al.
2020/0281224 A1 9/2020 Kizer et al.
2020/0282341 A1 9/2020 Kompala
2020/0288710 A1 9/2020 Fu Lein et al.
2020/0291043 A1 9/2020 Hager et al.
2020/0291060 A1 9/2020 Singh et al.
2020/0291370 A1 9/2020 Chavez
2020/0291408 A1 9/2020 Jessen et al.
2020/0291442 A1 9/2020 Douchin et al.
2020/0296960 A1 9/2020 Curtis et al.
2020/0296981 A1 9/2020 Barnes et al.
2020/0299412 A1 9/2020 Liu et al.
2020/0305481 A1 10/2020 Carlson et al.
2020/0308597 A1 10/2020 Gray
2020/0308599 A1 10/2020 Church et al.
2020/0308613 A1 10/2020 Louie et al.
2020/0308617 A1 10/2020 Mikkelsen et al.
2020/0315212 A1 10/2020 Watson et al.
2020/0315236 A1 10/2020 Thakkar et al.
2020/0316094 A1 10/2020 Horcajada et al.
2020/0318088 A1 10/2020 Donohoue et al.
2020/0318090 A1 10/2020 Donovan et al.
2020/0318108 A1 10/2020 Allocca et al.
2020/0323227 A1 10/2020 Capronnier et al.
2020/0323231 A1 10/2020 Schelle et al.
2020/0323237 A1 10/2020 Pibarot et al.
2020/0323904 A1 10/2020 Sands et al.
2020/0325462 A1 10/2020 Brouns et al.
2020/0325517 A1 10/2020 Houghton-Larsen et al.
2020/0329685 A1 10/2020 Qimron et al.
2020/0329726 A1 10/2020 Waksman et al.
2020/0329735 A1 10/2020 Cully et al.
2020/0329751 A1 10/2020 Thakkar et al.
2020/0330378 A1 10/2020 Friedman
2020/0331988 A9 10/2020 Manceur et al.
2020/0332248 A1 10/2020 Zhou et al.
2020/0332267 A1 10/2020 Hoyt et al.
2020/0332276 A1 10/2020 Buie et al.
2020/0332286 A1 10/2020 Gibson et al.
2020/0332288 A1 10/2020 Kantardzhieva et al.
2020/0332293 A1 10/2020 Thess
2020/0332564 A1 10/2020 Baum et al.
2020/0337336 A1 10/2020 Rouskey et al.
2020/0340000 A1 10/2020 Roy-Chaudhuri et al.
2020/0397021 A1 12/2020 Henderson, Jr. et al.
2020/0407741 A1 12/2020 Mason et al.
2021/0010017 A1 1/2021 El-Richani et al.
2021/0030014 A1 2/2021 Brown et al.
2021/0037848 A1 2/2021 Pandya et al.
2021/0037849 A1 2/2021 Pandya et al.
2021/0037851 A1 2/2021 Fraser et al.
2021/0051976 A1 2/2021 Fraser et al.
2021/0051977 A1 2/2021 Vrljic et al.
2021/0070842 A1 3/2021 Fraser et al.
2021/0221870 A1 7/2021 Pettit et al.
2021/0222186 A1 7/2021 El-Richani et al.
2021/0227849 A1 7/2021 Kiayei et al.
2021/0235714 A1 8/2021 Geistlinger et al.
2021/0251251 A1 8/2021 Holz-Schietinger et al.
2021/0259290 A1 8/2021 Ajami et al.
2021/0289804 A1 9/2021 Stiles et al.
2021/0289824 A1 9/2021 Brown et al.
2021/0307358 A1 10/2021 Henderson, Jr. et al.
2021/0329941 A1 10/2021 Geistlinger et al.
2021/0386085 A1 12/2021 Ray et al.
2021/0386086 A1 12/2021 Ray et al.
2021/0388310 A1 12/2021 Geistlinger et al.
2022/0007667 A1 1/2022 Ray et al.
2022/0007668 A1 1/2022 Ray et al.
2022/0033788 A1 2/2022 Geistlinger et al.
2022/0061365 A1 3/2022 Vrljic et al.
2022/0071250 A1 3/2022 Brown et al.
2022/0087286 A1 3/2022 Henderson, Jr. et al.
2022/0095654 A1 3/2022 Varadan et al.
2022/0098259 A1 3/2022 Lanquar et al.
2022/0098608 A1 3/2022 Lanquar et al.
2022/0117258 A1 4/2022 Pandya et al.
2022/0117285 A1 4/2022 Mahadevan et al.
2022/0169690 A1 6/2022 Lanquar et al.
2022/0174972 A1 6/2022 Gibson et al.
2022/0192239 A1 6/2022 Geistlinger et al.
2022/0211061 A1 7/2022 Geistlinger et al.

FOREIGN PATENT DOCUMENTS

EP 2597969 B1 10/2020
EP 3307091 B1 10/2020
EP 3409767 B1 10/2020
EP 3718418 A1 10/2020
EP 3721894 A1 10/2020
EP 3722322 A1 10/2020
EP 3722408 A1 10/2020
EP 3722431 A1 10/2020
EP 3725788 A1 10/2020
EP 4017287 A1 6/2022
EP 4027797 A2 7/2022
WO WO-9844139 A1 10/1998

(56) References Cited

FOREIGN PATENT DOCUMENTS

| | | | |
|---|---|---|---|
| WO | WO-9849326 | A1 | 11/1998 |
| WO | WO-9907866 | A1 | 2/1999 |
| WO | WO-9924592 | A1 | 5/1999 |
| WO | WO-9966054 | A2 | 12/1999 |
| WO | WO-0006757 | A1 | 2/2000 |
| WO | WO-0011200 | A2 | 3/2000 |
| WO | WO-0168822 | A2 | 9/2001 |
| WO | WO-0183792 | A2 | 11/2001 |
| WO | WO-02063975 | A2 | 8/2002 |
| WO | WO-02064750 | A2 | 8/2002 |
| WO | WO-02064814 | A2 | 8/2002 |
| WO | WO-03064613 | A2 | 8/2003 |
| WO | WO-2004069848 | A2 | 8/2004 |
| WO | WO-2005017168 | A1 | 2/2005 |
| WO | WO-2005055944 | A9 | 7/2005 |
| WO | WO-2005079232 | A2 | 9/2005 |
| WO | WO-2006016381 | A2 | 2/2006 |
| WO | WO-2013138793 | A2 | 9/2013 |
| WO | WO-2015038796 | A2 | 3/2015 |
| WO | WO-2015042405 | A1 | 3/2015 |
| WO | WO-2015127388 | A1 | 8/2015 |
| WO | WO-2015153666 | A1 | 10/2015 |
| WO | WO-2016029193 | A1 | 2/2016 |
| WO | WO-2016054375 | A1 | 4/2016 |
| WO | WO-2016099568 | A1 | 6/2016 |
| WO | WO-2016131000 | A2 | 8/2016 |
| WO | WO-2016142394 | A1 | 9/2016 |
| WO | WO-2016183163 | A1 | 11/2016 |
| WO | WO-2016197584 | A1 | 12/2016 |
| WO | WO-2017002945 | A1 | 1/2017 |
| WO | WO-2017025590 | A1 | 2/2017 |
| WO | WO-2017139558 | A1 | 8/2017 |
| WO | WO-2017180180 | A2 | 10/2017 |
| WO | WO-2017219046 | A1 | 12/2017 |
| WO | WO-2018042346 | A2 | 3/2018 |
| WO | WO-2018043219 | A1 | 3/2018 |
| WO | WO-2018081590 | A1 | 5/2018 |
| WO | WO-2018081592 | A2 | 5/2018 |
| WO | WO-2018187754 | A1 | 10/2018 |
| WO | WO-2018220188 | A1 | 12/2018 |
| WO | WO-2018220929 | A1 | 12/2018 |
| WO | WO-2019081346 | A1 | 5/2019 |
| WO | WO-2019081396 | A1 | 5/2019 |
| WO | WO-2019081398 | A1 | 5/2019 |
| WO | WO-2019081400 | A1 | 5/2019 |
| WO | WO-2019083940 | A1 | 5/2019 |
| WO | WO-2019086565 | A1 | 5/2019 |
| WO | WO-2019089333 | A1 | 5/2019 |
| WO | WO-2019089796 | A1 | 5/2019 |
| WO | WO-2019089820 | A1 | 5/2019 |
| WO | WO-2019090148 | A2 | 5/2019 |
| WO | WO-2019092069 | A2 | 5/2019 |
| WO | WO-2019092086 | A1 | 5/2019 |
| WO | WO-2019092505 | A1 | 5/2019 |
| WO | WO-2019093957 | A1 | 5/2019 |
| WO | WO-2019101490 | A1 | 5/2019 |
| WO | WO-2019101700 | A1 | 5/2019 |
| WO | WO-2019102381 | A1 | 5/2019 |
| WO | WO-2019104184 | A1 | 5/2019 |
| WO | WO-2019105908 | A1 | 6/2019 |
| WO | WO-2019105972 | A1 | 6/2019 |
| WO | WO-2019106147 | A1 | 6/2019 |
| WO | WO-2019110684 | A1 | 6/2019 |
| WO | WO-2019113132 | A1 | 6/2019 |
| WO | WO-2019115280 | A1 | 6/2019 |
| WO | WO-2019115735 | A1 | 6/2019 |
| WO | WO-2019116182 | A1 | 6/2019 |
| WO | WO-2019116183 | A1 | 6/2019 |
| WO | WO-2019116349 | A1 | 6/2019 |
| WO | WO-2019118480 | A1 | 6/2019 |
| WO | WO-2019118935 | A1 | 6/2019 |
| WO | WO-2019118984 | A2 | 6/2019 |
| WO | WO-2019121698 | A1 | 6/2019 |
| WO | WO-2019121852 | A1 | 6/2019 |
| WO | WO-2019121855 | A1 | 6/2019 |
| WO | WO-2019121856 | A1 | 6/2019 |
| WO | WO-2019122116 | A1 | 6/2019 |
| WO | WO-2019122123 | A1 | 6/2019 |
| WO | WO-2019122135 | A1 | 6/2019 |
| WO | WO-2019122336 | A1 | 6/2019 |
| WO | WO-2019122388 | A1 | 6/2019 |
| WO | WO-2019123430 | A1 | 6/2019 |
| WO | WO-2019125804 | A1 | 6/2019 |
| WO | WO-2019126562 | A1 | 6/2019 |
| WO | WO-2019144124 | A1 | 7/2019 |
| WO | WO-2019169409 | A1 | 9/2019 |
| WO | WO-2019170899 | A1 | 9/2019 |
| WO | WO-2019213155 | A1 | 11/2019 |
| WO | WO-2020061503 | A1 | 3/2020 |
| WO | WO-2020081789 | A1 | 4/2020 |
| WO | WO-2020089383 | A1 | 5/2020 |
| WO | WO-2020089384 | A1 | 5/2020 |
| WO | WO-2020089385 | A1 | 5/2020 |
| WO | WO-2020089444 | A1 | 5/2020 |
| WO | WO-2020089445 | A1 | 5/2020 |
| WO | WO-2020117927 | A1 | 6/2020 |
| WO | WO-2019161141 | A9 | 8/2020 |
| WO | WO-2020160187 | A2 | 8/2020 |
| WO | WO-2020168368 | A1 | 8/2020 |
| WO | WO-2020169389 | A1 | 8/2020 |
| WO | WO-2020169577 | A1 | 8/2020 |
| WO | WO-2020172143 | A1 | 8/2020 |
| WO | WO-2020126610 | A9 | 9/2020 |
| WO | WO-2020173860 | A1 | 9/2020 |
| WO | WO-2020173861 | A1 | 9/2020 |
| WO | WO-2020174070 | A1 | 9/2020 |
| WO | WO-2020176224 | A1 | 9/2020 |
| WO | WO-2020176389 | A1 | 9/2020 |
| WO | WO-2020176547 | A1 | 9/2020 |
| WO | WO-2020178307 | A1 | 9/2020 |
| WO | WO-2020180506 | A1 | 9/2020 |
| WO | WO-2020181101 | A1 | 9/2020 |
| WO | WO-2020181102 | A1 | 9/2020 |
| WO | WO-2020182929 | A1 | 9/2020 |
| WO | WO-2020183414 | A2 | 9/2020 |
| WO | WO-2020183419 | A1 | 9/2020 |
| WO | WO-2020185861 | A1 | 9/2020 |
| WO | WO-2020186059 | A2 | 9/2020 |
| WO | WO-2020190993 | A1 | 9/2020 |
| WO | WO-2020190998 | A1 | 9/2020 |
| WO | WO-2020191293 | A1 | 9/2020 |
| WO | WO-2020191369 | A1 | 9/2020 |
| WO | WO-2020193291 | A1 | 10/2020 |
| WO | WO-2020193385 | A1 | 10/2020 |
| WO | WO-2020193493 | A1 | 10/2020 |
| WO | WO-2020193495 | A1 | 10/2020 |
| WO | WO-2020202157 | A1 | 10/2020 |
| WO | WO-2020206385 | A1 | 10/2020 |
| WO | WO-2020208104 | A1 | 10/2020 |
| WO | WO-2020208190 | A1 | 10/2020 |
| WO | WO-2020208548 | A1 | 10/2020 |
| WO | WO-2020209959 | A1 | 10/2020 |
| WO | WO-2020210122 | A1 | 10/2020 |
| WO | WO-2020210160 | A2 | 10/2020 |
| WO | WO-2020210508 | A1 | 10/2020 |
| WO | WO-2020210810 | A1 | 10/2020 |
| WO | WO-2020212145 | A1 | 10/2020 |
| WO | WO-2020212235 | A1 | 10/2020 |
| WO | WO-2020212798 | A1 | 10/2020 |
| WO | WO-2020214542 | A1 | 10/2020 |
| WO | WO-2020214940 | A1 | 10/2020 |
| WO | WO-2020215017 | A1 | 10/2020 |
| WO | WO-2020219595 | A1 | 10/2020 |
| WO | WO-2020219596 | A1 | 10/2020 |
| WO | WO-2020219972 | A1 | 10/2020 |
| WO | WO-2020223700 | A1 | 11/2020 |
| WO | WO-2021007565 | A1 | 1/2021 |
| WO | WO-2021034980 | A1 | 2/2021 |
| WO | WO-2021050759 | A2 | 3/2021 |
| WO | WO-2021101647 | A1 | 5/2021 |
| WO | WO-2021130758 | A1 | 7/2021 |
| WO | WO-2021154806 | A1 | 8/2021 |
| WO | WO-2021168343 | A2 | 8/2021 |
| WO | WO-2021174226 | A1 | 9/2021 |

(56) References Cited

FOREIGN PATENT DOCUMENTS

| | | | |
|---|---|---|---|
| WO | WO-2021191914 | A1 | 9/2021 |
| WO | WO-2022031941 | A1 | 2/2022 |
| WO | WO-2022055513 | A1 | 3/2022 |
| WO | WO-2022072718 | | 4/2022 |
| WO | WO-2022072833 | A2 | 4/2022 |
| WO | WO-2022072846 | A2 | 4/2022 |
| WO | WO-2022076615 | A1 | 4/2022 |
| WO | WO-2022098835 | A1 | 5/2022 |
| WO | WO-2022098853 | A1 | 5/2022 |
| WO | WO-2022104227 | A1 | 5/2022 |
| WO | WO-2022117916 | A1 | 6/2022 |

OTHER PUBLICATIONS

Alvarez et al., "Higher accumulation of F1-V fusion recombinant protein in plants after induction of protein body formation," Plant Mol Biol 72:75-89 (2010).

Batt, C. A. et al., "Expression of recombinant bovine beta-lactoglobulin in *Escherichia coli*", Agricultural and biological chemistry, 54(4): 949-955 (1990).

Benchabane et al., "Preventing Unintended Proteolysis in Plant Protein Biofactories," Plant Biotechnology Journal 6:633:648 (2008).

Berry D., "Acid Makes Milk Much More," Dairy Foods, Jan. 2007, Retrieved from the Internet: URL: https://www.dairyfoods.com/articles/82509-%20all-about-acid, 4 pages.

Bradley and Vanderwarn, "Determination of moisture in cheese and cheese products," J. AOAC 84:570-592 (2001).

Breene, "Application of texture profile analysis to instrumental food texture evaluation," J. Texture Stud. 6:53-82 (1975).

Chen et al., "Textural analysis of cheese," J. Dairy Sci. 62:901-907 (1979).

Chiera et al., "Isolation of two highly active soybean (*Glycine max* (L.) Merr.) promoters and their characterization using a new automated image collection and analysis system," Plant Cell Reports,26(9):1501-1509 (2007).

Chong et al., "Expression of full-length bioactive antimicrobial human lactoferrin in potato plants," Transgenic Res. 9(1):71-78 (2000).

Chong et al., "Expression of the human milk protein beta-casein in transgenic potato plants," Transgenic Res. 6(4):289-296 (1997).

Cramer et al., "Transgenic Plants for Therapeutic Proteins: Linking Upstream and Downstream Strategies," J. Hammond et al (eds.), Plant Biotechnology, pp. 95-118 (2000).

Creamer 1974; Beta casein degradation in Gouda and cheddar cheese. Journal of Dairy Science 58(3): 287-292.

De La Torre et al., "The intron and 5' distal region of the soybean Gmubi promoter contribute to very high levels of gene expression in transiently and stably transformed tissues," Plant Cell Reports 34:111-120 (2015).

Deiss et al., "Functional Domains within the a Sequence Involved in the Cleavage-Packaging of Herpes Simplex Virus DNA," Journal of Virology, Sep. 1986, vol. 59, No. 3, pp. 605-618.

Devereux et al. "A comprehensive set of sequence analysis programs for the VAX" Nucleic Acids Research 12(1):387-395 (1984).

Diamos et al. "Chimeric 3' flanking regions strongly enhance gene expression in plants," Plant Biotechnology Journal 16(12):1971-1982 (2018).

Drake et al., "Relationship between instrumental and sensory measurements of cheese texture," J. Texture Stud. 30:451-476 (1999).

Dunwell, "Transgenic Crops: The Next Generation, or an Example of 2020 Vision," Annals of Botany 84:269-277 (1999).

Ems-Mcclung et al., "Expression of Maize Gamma Zein C-Terminus in *Escherichia coli*," Protein Expression and Purification 13, 1-8 (1998), Article No. PT980858.

Ferrer-Miralles et al., "Bacterial cell factories for recombinant protein production; expanding the catalogue," Microb Cell Fact. 12:113, pp. 1-4 (2013).

Fife et al., "Test for measuring the stretchability of melted cheese," J. Dairy Sci. 85(12):3539-3545 (2002).

Finer et al., "Transformation of soybean via particle bombardment of embryogenic suspension culture tissue," In Vitro Cell and Develop Biol—Plant 27P:175-182 (1991).

Galeaz. K, "Soy Cheese," Indiana Soybean Board, pp. 1-3, 1998.

GenBank Accession No. CAA25231, dated Jan. 31, 2003, 1 page.

GenBank accession No. Glyma.02G012600: Retrieved Oct. 14, 2020, from http://soykb.org/gene_card.php?gene=Glyma.02G012600.1, 4 pages.

GenBank accession No. J01263.1, dated Jun. 17, 1998, 3 pages.

GenBank accession No. L22576.1, dated Dec. 28, 2007, 2 pages.

GenBank Accession No. M15132.1, dated Apr. 26, 1993, 1 page.

GenBank accession No. X14712.1, dated Mar. 13, 1995, 2 pages.

GenBank accession No. X51514.1 dated Apr. 18, 2005, 2pages.

GenBank Accession No. X59836.1, dated Jul. 20, 1992, 2 pages.

GenBank accession No. Z50202.1, dated Aug. 21, 1998, 3 pages.

Ghag et al., Heterologous protein production in plant systems, GM Crops & Food, DOI: 10.1080/21645698.2016.1244599, 49 pages (2016).

Greenberg et al., "Human beta-casein. Amino acid sequence and identification of phosphorylation sites," J. Biol. Chem. 259(8):5132-5138 (1984).

Herman, "Soybean seed proteome rebalancing," Frontiers in plant science, 5, 437, 8 pages (2014).

Hernandez-Garcia, "A soybean (*Glycine max*) polyubiquitin promoter gives strong constitutive expression in transgenic soybean,"Plant cell reports,28(5):837-849 (2009).

Hernandez-Garcia et al., "High level transgenic expression of soybean (*Glycine max*) GmERF and Gmubi gene promoters isolated by a novel promoter analysis pipeline," BMC plant biology,10(1), 237, 16 pages (2010).

Horvath et al., "The production of recombinant proteins in transgenic barley grains," Proc. Natl. Acad. Sci. USA, 97:1914-1919 (2000).

Hudson et al., "Optimizing Recombinant Protein Expression in Soybean," Soybean—Molecular Aspects of Breeding, 24 pages (2011).

Imafidon et al., "Isolation, purification, and alteration of some functional groups of major milk proteins: a review," Crit. Rev. Food. Sci. Nutr. 37(7):663-689, (1997).

International Search Report and Written Opinion for International Application No. PCT/US2021/053002 dated Jan. 25, 2022, 18 pages.

International Search Report and Written Opinion issued by The International Searching Authority for Application No. PCT/US2018/026572, dated Jul. 20, 2018, 20 pages.

Jana et al., "Functional properties of Mozzarella cheese for its end use application," J. Food Sci Technol 54(12):3776-3778 (2017).

Kaminski et al., "Polymorphism of bovine beta-casein and its potential effect on human health," Journal of applied genetics,48(3), 189-198 (2007).

Kapoor et al., "Comparison of pilot scale and rapid visco analyzer process cheese manufacture," J. Dairy Sci. 87:2813-2821 (2004).

Kapoor et al., "Small-scale manufacture of process cheese using arapid visco analyzer," J. Dairy Sci. 88:3382-3391 (2005).

Karlin S., et al., "Applications And Statistics For Multiple High-scoring Segments In Molecular Sequences," Proceedings of National Academy of Sciences, Jun. 15, 1993, vol. 90, No. 12, pp. 5873-5877.

K-Casein (2018) download from "wikipedia.org/w/index.php?title=K-Casein&oldid=845015288"; pp. 1-5 (Year: 2018).

Kim, et al., Genetic modification of the soybean to enhance the -carotene content through seed-specific expression. PLoS One, 7(10), e48287, 12 pages (2012).

Kinney, "Development of genetically engineered soybean oils for food applications. Journal of Food Lipids," 3(4), 273-292 (1996).

Kuhn et al., "The baculovirus expression vector pBSV-8His directs secretion of histidine-tagged proteins," Gene, 162 225-229 (1995).

Loch, J. I. et al., "Engineered β-Lactoglobulin Produced in *E. coli*: Purification, Biophysical and Structural Characterisation", Molecular Biotechnology; 58:605-618 (2016).

Manninen, "Protein Hydrolysates in Sports Nutrition," Nutr Metab (Lond) 6:38, pp. 1-5 (2009).

(56) References Cited

OTHER PUBLICATIONS

Maughan et al., "Biolistic transformation, expression, and inheritance of bovine-casein in soybean (*Glycine max*)," In Vitro Cellular & Developmental Biology—Plant, 35(4):344-349 (1999).
Metzger et al., "RVA: Process cheese manufacture," Aust. J. Dairy Technol. 57:136 (2002).
Morison et al., "Viscosity and Non-Newtonian Behaviour of Concentrated Milk and Cream," International Journal of Food Properties 16(4):882-894 (2013).
Needleman & Wunsch, "A general method applicable to the search for similarities in the amino acid sequence of two proteins," J Mol. Biol. 48(3):443-453 (1970).
Nilshizawa & Ishimoto, "Maturation of somatic embryos as a model for soybean seed development," Plant biotechnology, 26(5), 543-550 (2009).
Old Europe Cheese; A lactose intolerant's guide to cheese. (2022) downloaded from https://oldeuropecheese.com/blog/a-lactose-intolerants-guide-to-cheese/ on Jun. 1, 2022; pp. 1-6.
Pearson and Lipman, "Improved tools for biological sequence comparison," PNAS USA, Apr. 1988, 85:2444-2448.
Philip, et al., "Processing and localization of bovine-casein expressed in transgenic soybean seeds under control of a soybean lectin expression cassette," Plant Science 161:323-335 (2001).
Pierce et al., "Ketocarotenoid production in soybean seeds through metabolic engineering," PloS one, 10(9), e0138196, 15 pages (2015).
Prevention, "Foods For Bone Health: Get Your Calcium Here," May 2012, Retrieved from the Internet: URL: https://www.prevention.com/health/a20446986/dietary-sources-of-calcium/, 3 pages.
Prow et al., "Melt analysis of process cheese spread or product using a rapid visco analyzer," J. Dairy Sci. 88:1277-1287 (2005).
Salmon et al., "Production of human lactoferrin in transgenic tobacco," Protein Expression and Purification 13:127-135 (1998).
Sanders.G.P., et al., "Curd tension of Milk and its Relationship to Firmness of Curd in Cheesemaking," Journal of Dairy Science; pp. 395-404, 1936.
Sathasivan et al., "Nucleotide sequence of a mutant acetolactate synthase gene from an imidazolinone-resistant *Arabidopsis thaliana* var. Columbia," Nucleic Acids Research 18(8):2188, 1 page (1990).
Substantially; definition (2021) Definition of Substantially, downloaded from the world wide web on Oct. 19, 2021; at https://www.dictionary.com/browse/substantially; definition pasted into body of Office Action. (Year: 2021).
Takaiwa et al., "Compensatory rebalancing of rice prolamins by production of recombinant prolamin/bioactive peptide fusion proteins within ER-derived protein bodies," Plant Cell Rep 37:209-223 (2018).
Takase et al., "Expression of human alpha-lactalbuminin transgenic tobacco," Journal of Biochemistry (Tokyo) 123:440-444 (1998).
Torrent et al., "Lysine-rich modified γ-zeins accumulate in protein bodies of transiently transformed maize endosperms," Plant Molecular Biology 34:139-149 (1997).
Truong et al., "Influence of carbon to nitrogen ratios on soybean somatic embryo (cv. Jack) growth and composition," Journal of experimental botany, 64(10), 2985-2995 (2013).
Uniprot Accession No. P02662, dated Aug. 12, 2020, 5 pages.
Uniprot Accession No. P02663.2, dated Aug. 12, 2020, 3 pages.
Uniprot Accession No. P02666.2, dated Oct. 7, 2020, 6 pages.
Uniprot Accession No. P02668.1, dated Aug. 12, 2020, 6 pages.
Uniprot Accession No. P33049.1, dated Dec. 11, 2019, 3 pages.
Webpage for AB-BLAST Basic Local Alignment Search Tool, dated Jun. 2, 2020: Retrieved Oct. 12, 2020, at http://blast.wustl/edu/blast/README.html, 22 pages.
West 2017; 6 dairy foods that are naturally low in lactose. Healthline, on the world wide web at healthline.com/nutrition/ dairy-foods-low-in-lactose, pp. 1-14.
Wong et al., "Improved co-expression of multiple genes in vectors containing internal ribosome entry sites (IRESes) from human genes," Gene Therapy 9:337-344 (2002).
Worley et al., "Engineering in vivo Instability of Firefly Luciferase and *Escherichia coli*-Glucuronidase in Higher Plants Using Recognition Elements from the Ubiquitin Pathway," Plant Molecular Biology 37:337-347 (1998).
Yang et al., "Comparative studies of the serum half-life extension of a protein via site-specific conjugation to a species-matched or -mismatched albumin," Biomaterials Science 6(8):2092-2100 (2018).
Zhang et al., "Isolation and characterization of "GmScream" promoters that regulate highly expressing soybean (*Glycine max* Merr.) genes," Plant Science 241:189-198 (2015).
International Search Report and Written Opinion issued by The International Searching Authority for Application No. PCT/US22/30788, dated Oct. 5, 2022, 17 pages.
Yun et al. "Role of the Phosphoryl Group of B-Casein in Milk Curdling" Agricultural and Biological Chemistry 46(6):1505-1511 (1982).
U.S. Appl. No. 15/947,596 (Abandoned).
U.S. Appl. No. 16/423,654 (Abandoned).
U.S. Appl. No. 16/862,011 (Pending).
U.S. Appl. No. 17/171,646 (Abandoned).
U.S. Appl. No. 17/039,759 (U.S. Pat. No. 10,947,552).
U.S. Appl. No. 17/039,760 (U.S. Pat. No. 10,894,812).
U.S. Appl. No. 17/127,090 (U.S. Pat. No. 11,034,743).
U.S. Appl. No. 17/127,418 (U.S. Pat. No. 10,988,521).
U.S. Appl. No. 17/157,105 (U.S. Pat. No. 11,072,797).
U.S. Appl. No. 17/326,785 (U.S. Pat. No. 11,142,555).
U.S. Appl. No. 17/374,125 (U.S. Pat. No. 11,401,526).
U.S. Appl. No. 17/493,100 (Pending).
U.S. Appl. No. 17/590,774 (Pending).

* cited by examiner

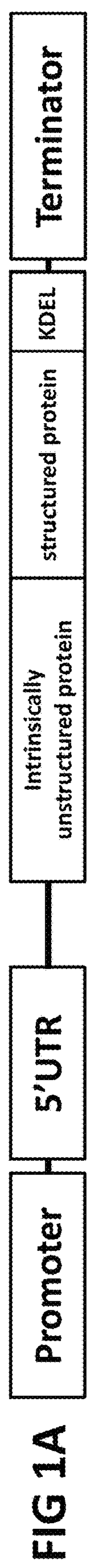
FIG 1A
Promoter
5'UTR
Intrinsically unstructured protein
structured protein
KDEL
Terminator

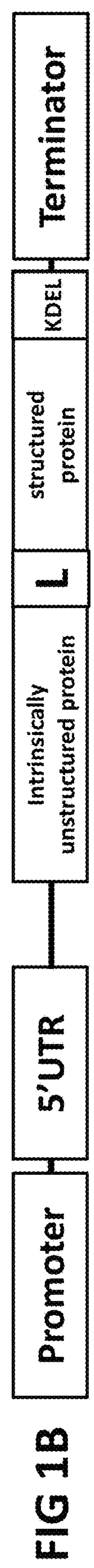
FIG 1B
Promoter
5'UTR
Intrinsically unstructured protein
L
structured protein
KDEL
Terminator

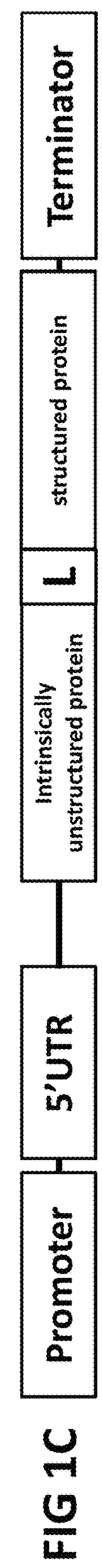
FIG 1C
Promoter
5'UTR
Intrinsically unstructured protein
L
structured protein
Terminator

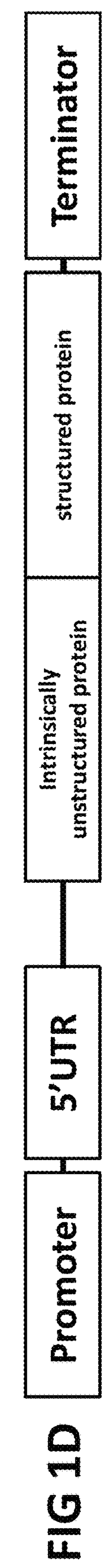
FIG 1D
Promoter
5'UTR
Intrinsically unstructured protein
structured protein
Terminator

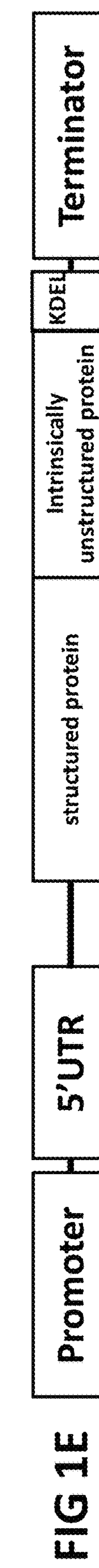
FIG 1E
Promoter
5'UTR
structured protein
Intrinsically unstructured protein
KDEL
Terminator

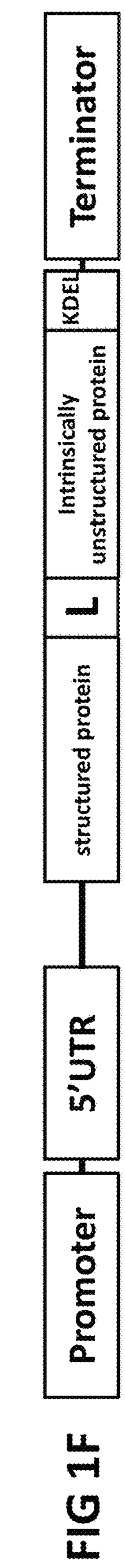
FIG 1F
Promoter
5'UTR
structured protein
L
Intrinsically unstructured protein
KDEL
Terminator FIG 1G
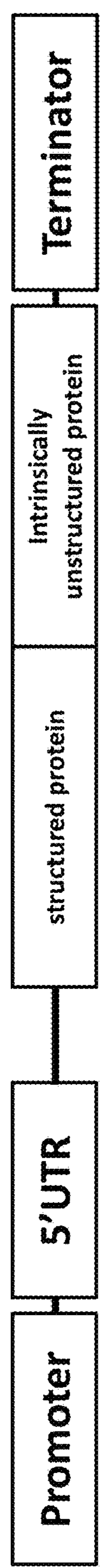
FIG 1H
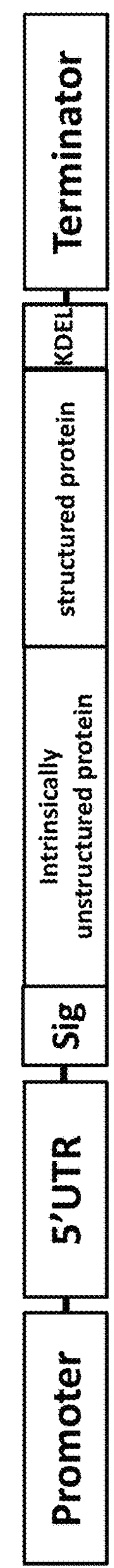
FIG 1I
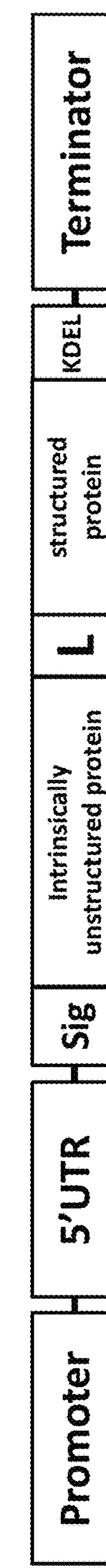
FIG 1J
FIG 1K
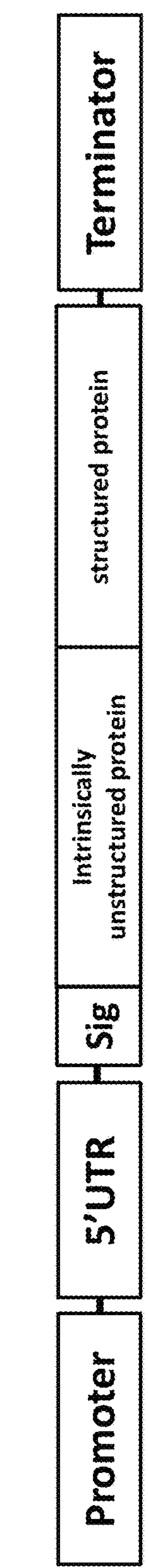
FIG 1L FIG 1M
Promoter
5'UTR
Sig
structured protein
Intrinsically unstructured protein
KDEL
Terminator

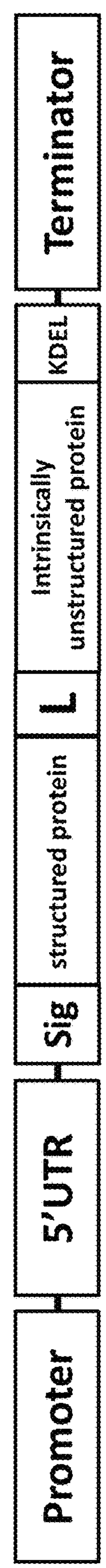
FIG 1N
Promoter
5'UTR
Sig
structured protein
L
Intrinsically unstructured protein
KDEL
Terminator FIG 1O
Promoter
5'UTR
Sig
structured protein
L
Intrinsically unstructured protein
Terminator

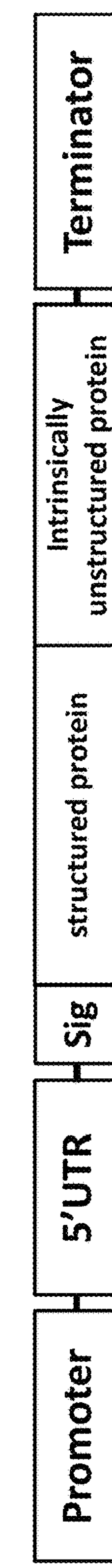
FIG 1P
Promoter
5'UTR
Sig
structured protein
Intrinsically unstructured protein
Terminator

SEQUENCE LISTING

```
<160> NUMBER OF SEQ ID NOS: 137

<210> SEQ ID NO 1
<211> LENGTH: 318
<212> TYPE: DNA
<213> ORGANISM: Artificial Sequence
<220> FEATURE:
<223> OTHER INFORMATION: Optimized para-kappa-casein truncated version 1
      (paraOKC1-T)

<400> SEQUENCE: 1

caagagcaga atcaagagca gccaatccgt tgtgagaagg acgagaggtt cttctcagac      60

aagatcgcca aatatatacc catacaatat gtactctcac gctaccctag ctacgggctt     120
```

```
aactactatc agcaaaaacc tgtagcactg ataaataacc agtttctccc ctatccctat    180

tatgctaaac ctgccgccgt gaggagtcca gcacaaatac ttcagtggca agtgctcagt    240

aacaccgtgc cagcaaaaag ctgccaggct cagcccacca caatggcccg tcatccccat    300

cctcacctta gcttcatg                                                  318


<210> SEQ ID NO 2
<211> LENGTH: 106
<212> TYPE: PRT
<213> ORGANISM: Artificial Sequence
<220> FEATURE:
<223> OTHER INFORMATION: Optimized para-kappa-casein truncated version 1
      (paraOKC1-T)

<400> SEQUENCE: 2

Gln Glu Gln Asn Gln Glu Gln Pro Ile Arg Cys Glu Lys Asp Glu Arg
1               5                   10                  15

Phe Phe Ser Asp Lys Ile Ala Lys Tyr Ile Pro Ile Gln Tyr Val Leu
            20                  25                  30

Ser Arg Tyr Pro Ser Tyr Gly Leu Asn Tyr Tyr Gln Gln Lys Pro Val
        35                  40                  45

Ala Leu Ile Asn Asn Gln Phe Leu Pro Tyr Pro Tyr Tyr Ala Lys Pro
    50                  55                  60

Ala Ala Val Arg Ser Pro Ala Gln Ile Leu Gln Trp Gln Val Leu Ser
65                  70                  75                  80

Asn Thr Val Pro Ala Lys Ser Cys Gln Ala Gln Pro Thr Thr Met Ala
                85                  90                  95

Arg His Pro His Pro His Leu Ser Phe Met
            100                 105


<210> SEQ ID NO 3
<211> LENGTH: 507
<212> TYPE: DNA
<213> ORGANISM: Artificial Sequence
<220> FEATURE:
<223> OTHER INFORMATION: Optimized kappa-casein truncated version 1
      (OKC1-T)

<400> SEQUENCE: 3

caagagcaga atcaagagca gccaatccgt tgtgagaagg acgagaggtt cttctcagac     60

aagatcgcca aatatatacc catacaatat gtactctcac gctaccctag ctacgggctt    120

aactactatc agcaaaaacc tgtagcactg ataaataacc agtttctccc ctatccctat    180

tatgctaaac ctgccgccgt gaggagtcca gcacaaatac ttcagtggca agtgctcagt    240

aacaccgtgc cagcaaaaag ctgccaggct cagcccacca caatggcccg tcatccccat    300

cctcacctta gcttcatggc aatcccacca aagaagaatc aagacaagac cgaaatacct    360

accatcaaca caattgcatc tggagagcct accagtacac caacaactga ggcagtagag    420

tctactgttg ctacccttga ggacagcccc gaggttatag agtccccacc tgagataaat    480

accgtgcagg tgacaagtac cgccgta                                        507


<210> SEQ ID NO 4
<211> LENGTH: 169
<212> TYPE: PRT
<213> ORGANISM: Artificial Sequence
<220> FEATURE:
<223> OTHER INFORMATION: Optimized kappa-casein truncated version 1
      (OKC1-T)
```

<400> SEQUENCE: 4

```
Gln Glu Gln Asn Gln Glu Gln Pro Ile Arg Cys Glu Lys Asp Glu Arg
1               5                   10                  15

Phe Phe Ser Asp Lys Ile Ala Lys Tyr Ile Pro Ile Gln Tyr Val Leu
            20                  25                  30

Ser Arg Tyr Pro Ser Tyr Gly Leu Asn Tyr Tyr Gln Gln Lys Pro Val
        35                  40                  45

Ala Leu Ile Asn Asn Gln Phe Leu Pro Tyr Pro Tyr Tyr Ala Lys Pro
    50                  55                  60

Ala Ala Val Arg Ser Pro Ala Gln Ile Leu Gln Trp Gln Val Leu Ser
65                  70                  75                  80

Asn Thr Val Pro Ala Lys Ser Cys Gln Ala Gln Pro Thr Thr Met Ala
                85                  90                  95

Arg His Pro His Pro His Leu Ser Phe Met Ala Ile Pro Pro Lys Lys
            100                 105                 110

Asn Gln Asp Lys Thr Glu Ile Pro Thr Ile Asn Thr Ile Ala Ser Gly
        115                 120                 125

Glu Pro Thr Ser Thr Pro Thr Thr Glu Ala Val Glu Ser Thr Val Ala
    130                 135                 140

Thr Leu Glu Asp Ser Pro Glu Val Ile Glu Ser Pro Pro Glu Ile Asn
145                 150                 155                 160

Thr Val Gln Val Thr Ser Thr Ala Val
                165
```

<210> SEQ ID NO 5
<211> LENGTH: 627
<212> TYPE: DNA
<213> ORGANISM: Artificial Sequence
<220> FEATURE:
<223> OTHER INFORMATION: Optimized beta-casein truncated version 2 (OBC-T2)

<400> SEQUENCE: 5

```
cgcgaactgg aagagttgaa cgtaccagga gagattgtag aatcactgag ctcctcagag     60

gagtctatta ctcgtatcaa caagaagata gagaagttcc aatccgagga gcaacaacaa    120

acagaggacg aattgcagga caagatacat cctttcgcac agacccagag cctcgtctat    180

ccctttccag gtccaatccc taactctctc ccccagaata tcccaccctt gactcagact    240

cccgtggtcg taccccctt cttgcaaccc gaggtgatgg gggtttctaa agtcaaagag    300

gctatggctc ctaaacataa ggaaatgcct tttcccaaat atccagtgga gccattcact    360

gagagccagt ctctgacact tacagatgtg gaaaacttgc acctgccctt gccactttttg    420

cagtcctgga tgcaccaacc acatcaaccc ttgcccccca cagtgatgtt tcctccacaa    480

tcagttctta gtctctccca aagcaaagtc cttccagtgc ctcagaaggc cgtcccatac    540

ccccagagag atatgccaat acaggcattc ttgctttacc aggaaccagt gctcggtcct    600

gtacgtggcc cattccctat catagtg                                         627
```

<210> SEQ ID NO 6
<211> LENGTH: 209
<212> TYPE: PRT
<213> ORGANISM: Artificial Sequence
<220> FEATURE:
<223> OTHER INFORMATION: Optimized beta-casein truncated version 2 (OBC-T2)

<400> SEQUENCE: 6

```
Arg Glu Leu Glu Glu Leu Asn Val Pro Gly Glu Ile Val Glu Ser Leu
1               5                   10                  15

Ser Ser Ser Glu Glu Ser Ile Thr Arg Ile Asn Lys Lys Ile Glu Lys
            20                  25                  30

Phe Gln Ser Glu Glu Gln Gln Gln Thr Glu Asp Glu Leu Gln Asp Lys
        35                  40                  45

Ile His Pro Phe Ala Gln Thr Gln Ser Leu Val Tyr Pro Phe Pro Gly
    50                  55                  60

Pro Ile Pro Asn Ser Leu Pro Gln Asn Ile Pro Pro Leu Thr Gln Thr
65                  70                  75                  80

Pro Val Val Val Pro Pro Phe Leu Gln Pro Glu Val Met Gly Val Ser
                85                  90                  95

Lys Val Lys Glu Ala Met Ala Pro Lys His Lys Glu Met Pro Phe Pro
            100                 105                 110

Lys Tyr Pro Val Glu Pro Phe Thr Glu Ser Gln Ser Leu Thr Leu Thr
        115                 120                 125

Asp Val Glu Asn Leu His Leu Pro Leu Pro Leu Leu Gln Ser Trp Met
    130                 135                 140

His Gln Pro His Gln Pro Leu Pro Pro Thr Val Met Phe Pro Pro Gln
145                 150                 155                 160

Ser Val Leu Ser Leu Ser Gln Ser Lys Val Leu Pro Val Pro Gln Lys
                165                 170                 175

Ala Val Pro Tyr Pro Gln Arg Asp Met Pro Ile Gln Ala Phe Leu Leu
            180                 185                 190

Tyr Gln Glu Pro Val Leu Gly Pro Val Arg Gly Pro Phe Pro Ile Ile
        195                 200                 205

Val
```

<210> SEQ ID NO 7
<211> LENGTH: 597
<212> TYPE: DNA
<213> ORGANISM: Artificial Sequence
<220> FEATURE:
<223> OTHER INFORMATION: Optimized alpha S1-casein truncated version 1(OaS1-T)

<400> SEQUENCE: 7

```
cgcccaaaac atcccataaa acatcaagga ttgccccagg aagtactcaa cgagaatctc     60

ctccgttttt tcgttgctcc tttccccgaa gtgttcggga aggaaaaagt aaacgagctt    120

tcaaaggaca tcggctctga aagtaccgag gatcaggcta tggaagatat caagcaaatg    180

gaggccgaat ctataagttc ttcagaagaa atagttccca actcagtgga gcagaagcac    240

attcagaaag aagacgtgcc cagcgagcgc tatctgggat atttggaaca gctgctcaga    300

ctgaaaaagt acaaggtgcc tcagctcgaa atcgtaccca atagtgctga agaaaggttg    360

cactcaatga aagaggggat tcacgcacaa caaaaagagc ctatgatcgg agtaaatcaa    420

gaactggcat acttttatcc cgagttgttt cgccaattct atcaactgga tgcctaccct    480

tccggtgcat ggtactacgt acccctcggt actcaatata ccgatgctcc ctccttttcc    540

gacattccta atcctatagg ttccgagaat agcgaaaaga ccaccatgcc cttatgg       597
```

<210> SEQ ID NO 8
<211> LENGTH: 199
<212> TYPE: PRT
<213> ORGANISM: Artificial Sequence
<220> FEATURE:
<223> OTHER INFORMATION: Optimized alpha S1-casein truncated version 1(OaS1-T)

<400> SEQUENCE: 8

```
Arg Pro Lys His Pro Ile Lys His Gln Gly Leu Pro Gln Glu Val Leu
1               5                   10                  15

Asn Glu Asn Leu Leu Arg Phe Phe Val Ala Pro Phe Pro Glu Val Phe
            20                  25                  30

Gly Lys Glu Lys Val Asn Glu Leu Ser Lys Asp Ile Gly Ser Glu Ser
        35                  40                  45

Thr Glu Asp Gln Ala Met Glu Asp Ile Lys Gln Met Glu Ala Glu Ser
    50                  55                  60

Ile Ser Ser Ser Glu Glu Ile Val Pro Asn Ser Val Glu Gln Lys His
65                  70                  75                  80

Ile Gln Lys Glu Asp Val Pro Ser Glu Arg Tyr Leu Gly Tyr Leu Glu
                85                  90                  95

Gln Leu Leu Arg Leu Lys Lys Tyr Lys Val Pro Gln Leu Glu Ile Val
            100                 105                 110

Pro Asn Ser Ala Glu Glu Arg Leu His Ser Met Lys Glu Gly Ile His
        115                 120                 125

Ala Gln Gln Lys Glu Pro Met Ile Gly Val Asn Gln Glu Leu Ala Tyr
    130                 135                 140

Phe Tyr Pro Glu Leu Phe Arg Gln Phe Tyr Gln Leu Asp Ala Tyr Pro
145                 150                 155                 160

Ser Gly Ala Trp Tyr Tyr Val Pro Leu Gly Thr Gln Tyr Thr Asp Ala
                165                 170                 175

Pro Ser Phe Ser Asp Ile Pro Asn Pro Ile Gly Ser Glu Asn Ser Glu
            180                 185                 190

Lys Thr Thr Met Pro Leu Trp
        195
```

<210> SEQ ID NO 9
<211> LENGTH: 486
<212> TYPE: DNA
<213> ORGANISM: Artificial Sequence
<220> FEATURE:
<223> OTHER INFORMATION: Optimized Beta Lactoglobulin 1 (OLG1)

<400> SEQUENCE: 9

```
ttgatcgtaa cacagactat gaagggtctt gatatacaga aggtggccgg gacttggtac     60

agtttggcaa tggccgcatc cgacatctcc ttgttggacg cacaatcagc ccattgcgt    120

gtgtacgtag aagagcttaa accaactccc gagggggatc tggaaattct gctccagaaa    180

tgggagaacg gtgagtgcgc ccagaagaag atcatcgcag agaagaccaa aattccagca    240

gtattcaaaa tcgacgcatt gaacgaaaat aaggtgctcg tactggacac tgattataag    300

aagtatctcc ttttctgtat ggagaactca gcagagcctg aacagagtct tgcctgccaa    360

tgccttgttc gtaccccaga ggtagatgat gaagctctgg aaaagttcga taaggccctt    420

aaggctctgc ctatgcacat taggctttct ttcaatccaa ctcaacttga ggaacaatgt    480

cacatt                                                               486
```

<210> SEQ ID NO 10
<211> LENGTH: 162
<212> TYPE: PRT
<213> ORGANISM: Artificial Sequence

```
<220> FEATURE:
<223> OTHER INFORMATION: Optimized Beta Lactoglobulin 1 (OLG1)

<400> SEQUENCE: 10

Leu Ile Val Thr Gln Thr Met Lys Gly Leu Asp Ile Gln Lys Val Ala
1               5                   10                  15

Gly Thr Trp Tyr Ser Leu Ala Met Ala Ala Ser Asp Ile Ser Leu Leu
            20                  25                  30

Asp Ala Gln Ser Ala Pro Leu Arg Val Tyr Val Glu Glu Leu Lys Pro
        35                  40                  45

Thr Pro Glu Gly Asp Leu Glu Ile Leu Leu Gln Lys Trp Glu Asn Gly
    50                  55                  60

Glu Cys Ala Gln Lys Lys Ile Ile Ala Glu Lys Thr Lys Ile Pro Ala
65                  70                  75                  80

Val Phe Lys Ile Asp Ala Leu Asn Glu Asn Lys Val Leu Val Leu Asp
                85                  90                  95

Thr Asp Tyr Lys Lys Tyr Leu Leu Phe Cys Met Glu Asn Ser Ala Glu
            100                 105                 110

Pro Glu Gln Ser Leu Ala Cys Gln Cys Leu Val Arg Thr Pro Glu Val
        115                 120                 125

Asp Asp Glu Ala Leu Glu Lys Phe Asp Lys Ala Leu Lys Ala Leu Pro
    130                 135                 140

Met His Ile Arg Leu Ser Phe Asn Pro Thr Gln Leu Glu Glu Gln Cys
145                 150                 155                 160

His Ile


<210> SEQ ID NO 11
<211> LENGTH: 486
<212> TYPE: DNA
<213> ORGANISM: Artificial Sequence
<220> FEATURE:
<223> OTHER INFORMATION: Optimized Beta Lactoglobulin 2 (OLG2)

<400> SEQUENCE: 11

cttattgtga cccaaaccat gaagggcctc gacattcaaa aggttgccgg aacctggtac      60

tcccttgcta tggctgcttc cgatatctcc ttgctcgatg ctcaatccgc tccacttagg     120

gtgtacgtgg aagagttgaa gccaactcca gagggcgatc ttgagatctt gcttcaaaag     180

tgggagaacg atgagtgcgc ccagaagaag attatcgccg aaaagaccaa gattcccgcc     240

gtgttcaaga tcgatgctct caacgagaac aaggtgctcg tgctcgatac cgactacaag     300

aagtaccttc tcgtctgcat ggaaaactcc gctgagccag agcaatctct tgtttgccaa     360

tgccttgtga ggaccccaga ggttgacgat gaagctcttg agaagttcga caaggctctc     420

aaggctttgc ctatgcacat ccgccttagc ttcaacccaa ctcagcttga ggaacagtgc     480

cacatc                                                                486


<210> SEQ ID NO 12
<211> LENGTH: 486
<212> TYPE: DNA
<213> ORGANISM: Artificial Sequence
<220> FEATURE:
<223> OTHER INFORMATION: Optimized Beta Lactoglobulin 3 (OLG3)

<400> SEQUENCE: 12

ctcattgtta cacaaaccat gaagggtctt gacattcaga aggttgctgg gacatggtat      60

tcactagcga tggctgcttc tgatatctcc ctgttggatg cacagtctgc ccccctgaga     120
```

```
gtgtatgttg aagaactgaa accgacacct gaaggagact tggaaatttt actccagaaa    180

tgggaaaatg atgagtgtgc ccaaaagaag ataatagccg agaagaccaa aattcctgct    240

gtgtttaaga ttgatgcttt gaatgagaac aaagtactag tcctcgacac tgattacaag    300

aaatacttat tagtgtgcat ggaaaacagc gcagagccag aacaatcact tgtttgtcaa    360

tgtttggtcc gtactccaga ggtagatgat gaagcattgg agaaatttga taaagcattg    420

aaggcacttc caatgcatat aaggcttagt ttcaatccta ctcagcttga agagcaatgc    480

cacatc                                                                486


<210> SEQ ID NO 13
<211> LENGTH: 486
<212> TYPE: DNA
<213> ORGANISM: Artificial Sequence
<220> FEATURE:
<223> OTHER INFORMATION: Optimized Beta Lactoglobulin 4 (OLG4)

<400> SEQUENCE: 13

cttatagtaa ctcaaaccat gaagggactt gatatccaaa aagttgcagg aacctggtac     60

tcactggcta tggcagcttc cgacatctcc ttgttggacg cacaatccgc accattgcgc    120

gtctacgttg aggagttgaa acctacacca gagggggatc ttgagatttt gctccagaaa    180

tgggagaacg acgagtgtgc ccagaaaaaa attatagcag agaagactaa aattcctgct    240

gtttttaaga ttgatgccct gaacgagaat aaggtactgg tcctcgacac tgattataaa    300

aagtatttgc tggtgtgtat ggagaacagt gctgaacctg aacagagcct ggtctgtcaa    360

tgtcttgtaa ggacacctga ggttgatgac gaggcacttg aaaaattcga caaggccctt    420

aaggctctgc ctatgcacat ccgtctgagt ttcaacccta ctcagttgga ggaacaatgt    480

catatt                                                                486


<210> SEQ ID NO 14
<211> LENGTH: 96
<212> TYPE: DNA
<213> ORGANISM: Glycine max

<400> SEQUENCE: 14

atggctactt caaagttgaa aacccagaat gtggttgtat ctctctccct aaccttaacc     60

ttggtactgg tgctactgac cagcaaggca aactca                               96


<210> SEQ ID NO 15
<211> LENGTH: 32
<212> TYPE: PRT
<213> ORGANISM: Glycine max

<400> SEQUENCE: 15

Met Ala Thr Ser Lys Leu Lys Thr Gln Asn Val Val Val Ser Leu Ser
1               5                   10                  15

Leu Thr Leu Thr Leu Val Leu Val Leu Leu Thr Ser Lys Ala Asn Ser
            20                  25                  30


<210> SEQ ID NO 16
<211> LENGTH: 57
<212> TYPE: DNA
<213> ORGANISM: Glycine max

<400> SEQUENCE: 16

atggccaagc tagtttttc cctttgtttt ctgcttttca gtggctgctg cttcgct         57
```

<210> SEQ ID NO 17
<211> LENGTH: 19
<212> TYPE: PRT
<213> ORGANISM: Glycine max

<400> SEQUENCE: 17

```
Met Ala Lys Leu Val Phe Ser Leu Cys Phe Leu Leu Phe Ser Gly Cys
1               5                   10                  15

Cys Phe Ala
```

<210> SEQ ID NO 18
<211> LENGTH: 1543
<212> TYPE: DNA
<213> ORGANISM: Glycine max

<400> SEQUENCE: 18

```
cattgtactc ccagtatcat tatagtgaaa gttttggctc tctcgccggt ggttttttac      60

ctctatttaa aggggttttc cacctaaaaa ttctggtatc attctcactt tacttgttac     120

tttaatttct cataatcttt ggttgaaatt atcacgcttc cgcacacgat atccctacaa     180

atttattatt tgttaaacat tttcaaaccg cataaaattt tatgaagtcc cgtctatctt     240

taatgtagtc taacattttc atattgaaat atataattta cttaatttta gcgttggtag     300

aaagcataat gatttattct tattcttctt catataaatg tttaatatac aatataaaca     360

aattctttac cttaagaagg atttcccatt ttatatttta aaaatatatt tatcaaatat     420

ttttcaacca cgtaaatcac ataataataa gttgtttcaa aagtaataaa atttaactcc     480

ataatttttt tatttgactg atcttaaagc aacacccagt gacacaacta gccatttttt     540

tctttgaata aaaaaatcca attatcattg tatttttttt atacaatgaa aatttcacca     600

aacaatgatt tgtggtattt ctgaagcaag tcatgttatg caaaattcta taattcccat     660

ttgacactac ggaagtaact gaagatctgc ttttacatgc gagacacatc ttctaaagta     720

attttaataa tagttactat attcaagatt tcatatatca aatactcaat attacttcta     780

aaaaattaat tagatataat taaaatatta ctttttttaat tttaagttta attgttgaat     840

ttgtgactat tgatttatta ttctactatg tttaaattgt tttataggta gtttaaagta     900

aatataagta atgtagtaga gtgttagagt gttaccctaa accataaact ataagattta     960

tggtggacta attttcatat atttcttatt gcttttacct tttcttggta tgtaagtccg    1020

taactggaat tactgtgggt tgccatgaca ctctgtggtc ttttggttca tgcatggatg    1080

cttgcgcaag aaaaagacaa agaacaaaga aaaaagacaa aacagagaga caaaacgcaa    1140

tcacacaacc aactcaaatt agtcactggc tgatcaagat cgccgcgtcc atgtatgtct    1200

aaatgccatg caaagcaaca cgtgcttaac atgcacttta aatggctcac ccatcccaac    1260

ccactcacaa acacattgcc tttttcttca tcatcaccac aaccacctgt atatattcat    1320

tctcttccgc cacctcaatt tcttcacttc aacacacgtc aacctgcata tgcgtgtcat    1380

cccatgccca aatctccatg catgttccta ccaccttctc tcttatataa tacctataaa    1440

tacctctaat atcactcact tctttcatca tccatccatc cagagtacta ctactctact    1500

actataatac cccaacccaa ctcatattca atactactct act                      1543
```

<210> SEQ ID NO 19
<211> LENGTH: 1384
<212> TYPE: DNA
<213> ORGANISM: Glycine max

<400> SEQUENCE: 19
aacacaagct tcaagtttta aaaggaaaaa tgtcagccaa aaactttaaa taaaatggta 60
acaaggaaat tattcaaaaa ttacaaacct cgtcaaaata ggaaagaaaa aaagtttagg 120
gatttagaaa aaacatcaat ctagttccac cttattttat agagagaaga aactaatata 180
taagaactaa aaaacagaag aatagaaaaa aaaagtattg acaggaaaga aaaagtagct 240
gtatgcttat aagtactttg aggatttgaa ttctctctta taaaacacaa acacaatttt 300
tagattttat ttaaataatc atcaatccga ttataattat ttatatattt ttctattttc 360
aaagaagtaa atcatgagct tttccaactc aacatctatt ttttttctct caaccttttt 420
cacatcttaa gtagtctcac cctttatata tataacttat ttcttacctt ttacattatg 480
taacttttat caccaaaacc aacaacttta aaattttatt aaatagactc cacaagtaac 540
ttgacactct tacattcatc gacattaact tttatctgtt ttataaatat tattgtgata 600
taatttaatc aaaataacca caaactttca taaaaggttc ttattaagca tggcatttaa 660
taagcaaaaa caactcaatc actttcatat aggaggtagc ctaagtacgt actcaaaatg 720
ccaacaaata aaaaaaaagt tgctttaata atgccaaaac aaattaataa aacacttaca 780
acaccggatt ttttttaatt aaaatgtgcc atttaggata aatagttaat atttttaata 840
attatttaaa aagccgtatc tactaaaatg atttttattt ggttgaaaat attaatatgt 900
ttaaatcaac acaatctatc aaaattaaac taaaaaaaaa ataagtgtac gtggttaaca 960
ttagtacagt aatataagag gaaaatgaga aattaagaaa ttgaaagcga gtctaatttt 1020
taaattatga acctgcatat ataaaaggaa agaaagaatc caggaagaaa agaaatgaaa 1080
ccatgcatgg tcccctcgtc atcacgagtt tctgccattt gcaatagaaa cactgaaaca 1140
cctttctctt tgtcacttaa ttgagatgcc gaagccacct cacaccatga acttcatgag 1200
gtgtagcacc caaggcttcc atagccatgc atactgaaga atgtctcaag ctcagcaccc 1260
tacttctgtg acgtgtccct cattcacctt cctctcttcc ctataaataa ccacgcctca 1320
ggttctccgc ttcacaactc aaacattctc tccattggtc cttaaacact catcagtcat 1380
cacc 1384

<210> SEQ ID NO 20
<211> LENGTH: 13
<212> TYPE: DNA
<213> ORGANISM: Glycine max

<400> SEQUENCE: 20
tgaatgcatg atc 13

<210> SEQ ID NO 21
<211> LENGTH: 1197
<212> TYPE: DNA
<213> ORGANISM: Glycine max

<400> SEQUENCE: 21
aataaataaa atgggagcaa taaataaaat gggagctcat atatttacac catttacact 60
gtctattatt caccatgcca attattactt cataatttta aaattatgtc atttttaaaa 120
attgcttaat gatggaaagg attattataa gttaaaagta taacatagat aaactaacca 180
caaaacaaat caatataaac taacttactc tcccatctaa tttttattta aatttcttta 240
cacttctctt ccatttctat ttctacaaca ttatttaaca tttttattgt atttttctta 300
ctttctaact ctattcattt caaaaatcaa tatatgttta tcaccacctc tctaaaaaaa 360

```
actttacaat cattggtcca gaaaagttaa atcacgagat ggtcatttta gcattaaaac    420

aacgattctt gtatcactat ttttcagcat gtagtccatt ctcttcaaac aaagacagcg    480

gctatataat cgttgtgtta tattcagtct aaaacaattg ttatggtaaa agtcgtcatt    540

ttacgccttt ttaaaagata taaaatgaca gttatggtta aaagtcatca tgttagatcc    600

tccttaaaga tataaaatga cagttttgga taaaaagtgg tcattttata cgctcttgaa    660

agatataaaa cgacggttat ggtaaaagct gccattttaa atgaaatatt tttgttttag    720

ttcattttgt ttaatgctaa tcccatttaa attgacttgt acaattaaaa ctcacccacc    780

cagatacaat ataaactaac ttactctcac agctaagttt tatttaaatt tctttacact    840

tcttttccat ttctatttct atgacattaa ctaacatttt tctcgtaatt ttttttctta    900

ttttctaact ctatccattt caaatcgata tatgtttatc accaccactt taaaaagaaa    960

atttacaatt tctcgtgcaa aaaagctaaa tcatgaccgt cattttagca ttaaaacaac   1020

gattcttgta tcgttgtttt tcagcatgta gtccattctt ttcaagcaaa gacaacagct   1080

atataatcat cgtgttatat tcagtctaaa acaacagtaa tgataaaagt catcatttta   1140

ggcctttctg aaatatatag aacgacattc atggtaaaaa atcgtcattt tagatcc      1197
```

<210> SEQ ID NO 22
<211> LENGTH: 253
<212> TYPE: DNA
<213> ORGANISM: Glycine max

<400> SEQUENCE: 22

```
gatcgttcaa acatttggca ataaagtttc ttaagattga atcctgttgc cggtcttgcg     60

atgattatca tataatttct gttgaattac gttaagcatg taataattaa catgtaatgc    120

atgacgttat ttatgagatg ggtttttatg attagagtcc cgcaattata catttaatac    180

gcgatagaaa acaaaatata gcgcgcaaac taggataaat tatcgcgcgc ggtgtcatct    240

atgttactag atc                                                       253
```

<210> SEQ ID NO 23
<211> LENGTH: 4
<212> TYPE: PRT
<213> ORGANISM: Unknown
<220> FEATURE:
<223> OTHER INFORMATION: Carboxy-terminal endoplasmic reticulum retention/retrieval signal

<400> SEQUENCE: 23

Lys Asp Glu Leu
1

<210> SEQ ID NO 24
<211> LENGTH: 4
<212> TYPE: PRT
<213> ORGANISM: Unknown
<220> FEATURE:
<223> OTHER INFORMATION: Carboxy-terminal endoplasmic reticulum retention/retrieval signal

<400> SEQUENCE: 24

His Asp Glu Leu
1

<210> SEQ ID NO 25
<211> LENGTH: 4
<212> TYPE: PRT
<213> ORGANISM: Unknown

<220> FEATURE:
<223> OTHER INFORMATION: Carboxy-terminal endoplasmic reticulum retention/retrieval signal

<400> SEQUENCE: 25

His Asp Glu Phe
1

<210> SEQ ID NO 26
<211> LENGTH: 4
<212> TYPE: PRT
<213> ORGANISM: Unknown
<220> FEATURE:
<223> OTHER INFORMATION: Carboxy-terminal endoplasmic reticulum retention/retrieval signal

<400> SEQUENCE: 26

Arg Asp Glu Phe
1

<210> SEQ ID NO 27
<211> LENGTH: 4
<212> TYPE: PRT
<213> ORGANISM: Unknown
<220> FEATURE:
<223> OTHER INFORMATION: Carboxy-terminal endoplasmic reticulum retention/retrieval signal

<400> SEQUENCE: 27

Arg Asp Glu Leu
1

<210> SEQ ID NO 28
<211> LENGTH: 4
<212> TYPE: PRT
<213> ORGANISM: Unknown
<220> FEATURE:
<223> OTHER INFORMATION: Carboxy-terminal endoplasmic reticulum retention/retrieval signal

<400> SEQUENCE: 28

Trp Asp Glu Leu
1

<210> SEQ ID NO 29
<211> LENGTH: 4
<212> TYPE: PRT
<213> ORGANISM: Unknown
<220> FEATURE:
<223> OTHER INFORMATION: Carboxy-terminal endoplasmic reticulum retention/retrieval signal

<400> SEQUENCE: 29

Tyr Asp Glu Leu
1

<210> SEQ ID NO 30
<211> LENGTH: 4
<212> TYPE: PRT
<213> ORGANISM: Unknown
<220> FEATURE:
<223> OTHER INFORMATION: Carboxy-terminal endoplasmic reticulum retention/retrieval signal

<400> SEQUENCE: 30

His Glu Glu Phe
1

<210> SEQ ID NO 31
<211> LENGTH: 4
<212> TYPE: PRT
<213> ORGANISM: Unknown
<220> FEATURE:
<223> OTHER INFORMATION: Carboxy-terminal endoplasmic reticulum
retention/retrieval signal

<400> SEQUENCE: 31

His Glu Glu Leu
1

<210> SEQ ID NO 32
<211> LENGTH: 4
<212> TYPE: PRT
<213> ORGANISM: Unknown
<220> FEATURE:
<223> OTHER INFORMATION: Carboxy-terminal endoplasmic reticulum
retention/retrieval signal

<400> SEQUENCE: 32

Lys Glu Glu Leu
1

<210> SEQ ID NO 33
<211> LENGTH: 4
<212> TYPE: PRT
<213> ORGANISM: Unknown
<220> FEATURE:
<223> OTHER INFORMATION: Carboxy-terminal endoplasmic reticulum
retention/retrieval signal

<400> SEQUENCE: 33

Arg Glu Glu Leu
1

<210> SEQ ID NO 34
<211> LENGTH: 4
<212> TYPE: PRT
<213> ORGANISM: Unknown
<220> FEATURE:
<223> OTHER INFORMATION: Carboxy-terminal endoplasmic reticulum
retention/retrieval signal

<400> SEQUENCE: 34

Lys Ala Glu Leu
1

<210> SEQ ID NO 35
<211> LENGTH: 4
<212> TYPE: PRT
<213> ORGANISM: Unknown
<220> FEATURE:
<223> OTHER INFORMATION: Carboxy-terminal endoplasmic reticulum
retention/retrieval signal

<400> SEQUENCE: 35

Lys Cys Glu Leu
1

<210> SEQ ID NO 36
<211> LENGTH: 4
<212> TYPE: PRT
<213> ORGANISM: Unknown
<220> FEATURE:
<223> OTHER INFORMATION: Carboxy-terminal endoplasmic reticulum
retention/retrieval signal

<400> SEQUENCE: 36

Lys Phe Glu Leu
1

<210> SEQ ID NO 37
<211> LENGTH: 4
<212> TYPE: PRT
<213> ORGANISM: Unknown
<220> FEATURE:
<223> OTHER INFORMATION: Carboxy-terminal endoplasmic reticulum retention/retrieval signal

<400> SEQUENCE: 37

Lys Gly Glu Leu
1

<210> SEQ ID NO 38
<211> LENGTH: 4
<212> TYPE: PRT
<213> ORGANISM: Unknown
<220> FEATURE:
<223> OTHER INFORMATION: Carboxy-terminal endoplasmic reticulum retention/retrieval signal

<400> SEQUENCE: 38

Lys His Glu Leu
1

<210> SEQ ID NO 39
<211> LENGTH: 4
<212> TYPE: PRT
<213> ORGANISM: Unknown
<220> FEATURE:
<223> OTHER INFORMATION: Carboxy-terminal endoplasmic reticulum retention/retrieval signal

<400> SEQUENCE: 39

Lys Leu Glu Leu
1

<210> SEQ ID NO 40
<211> LENGTH: 4
<212> TYPE: PRT
<213> ORGANISM: Unknown
<220> FEATURE:
<223> OTHER INFORMATION: Carboxy-terminal endoplasmic reticulum retention/retrieval signal

<400> SEQUENCE: 40

Lys Asn Glu Leu
1

<210> SEQ ID NO 41
<211> LENGTH: 4
<212> TYPE: PRT
<213> ORGANISM: Unknown
<220> FEATURE:
<223> OTHER INFORMATION: Carboxy-terminal endoplasmic reticulum retention/retrieval signal

<400> SEQUENCE: 41

Lys Gln Glu Leu
1

<210> SEQ ID NO 42
<211> LENGTH: 4
<212> TYPE: PRT
<213> ORGANISM: Unknown
<220> FEATURE:
<223> OTHER INFORMATION: Carboxy-terminal endoplasmic reticulum retention/retrieval signal

<400> SEQUENCE: 42

Lys Arg Glu Leu
1

<210> SEQ ID NO 43
<211> LENGTH: 4
<212> TYPE: PRT
<213> ORGANISM: Unknown
<220> FEATURE:
<223> OTHER INFORMATION: Carboxy-terminal endoplasmic reticulum retention/retrieval signal

<400> SEQUENCE: 43

Lys Ser Glu Leu
1

<210> SEQ ID NO 44
<211> LENGTH: 4
<212> TYPE: PRT
<213> ORGANISM: Unknown
<220> FEATURE:
<223> OTHER INFORMATION: Carboxy-terminal endoplasmic reticulum retention/retrieval signal

<400> SEQUENCE: 44

Lys Val Glu Leu
1

<210> SEQ ID NO 45
<211> LENGTH: 4
<212> TYPE: PRT
<213> ORGANISM: Unknown
<220> FEATURE:
<223> OTHER INFORMATION: Carboxy-terminal endoplasmic reticulum retention/retrieval signal

<400> SEQUENCE: 45

Lys Trp Glu Leu
1

<210> SEQ ID NO 46
<211> LENGTH: 4
<212> TYPE: PRT
<213> ORGANISM: Unknown
<220> FEATURE:
<223> OTHER INFORMATION: Carboxy-terminal endoplasmic reticulum retention/retrieval signal

<400> SEQUENCE: 46

Lys Tyr Glu Leu
1

<210> SEQ ID NO 47
<211> LENGTH: 4
<212> TYPE: PRT
<213> ORGANISM: Unknown
<220> FEATURE:
<223> OTHER INFORMATION: Carboxy-terminal endoplasmic reticulum retention/retrieval signal

<400> SEQUENCE: 47

Lys Glu Asp Leu
1

<210> SEQ ID NO 48
<211> LENGTH: 4
<212> TYPE: PRT
<213> ORGANISM: Unknown
<220> FEATURE:
<223> OTHER INFORMATION: Carboxy-terminal endoplasmic reticulum retention/retrieval signal

<400> SEQUENCE: 48

Lys Ile Glu Leu
1

<210> SEQ ID NO 49
<211> LENGTH: 4
<212> TYPE: PRT
<213> ORGANISM: Unknown
<220> FEATURE:
<223> OTHER INFORMATION: Carboxy-terminal endoplasmic reticulum retention/retrieval signal

<400> SEQUENCE: 49

Asp Lys Glu Leu
1

<210> SEQ ID NO 50
<211> LENGTH: 4
<212> TYPE: PRT
<213> ORGANISM: Unknown
<220> FEATURE:
<223> OTHER INFORMATION: Carboxy-terminal endoplasmic reticulum retention/retrieval signal

<400> SEQUENCE: 50

Phe Asp Glu Leu
1

<210> SEQ ID NO 51
<211> LENGTH: 4
<212> TYPE: PRT
<213> ORGANISM: Unknown
<220> FEATURE:
<223> OTHER INFORMATION: Carboxy-terminal endoplasmic reticulum retention/retrieval signal

<400> SEQUENCE: 51

Lys Asp Glu Phe
1

<210> SEQ ID NO 52
<211> LENGTH: 4
<212> TYPE: PRT
<213> ORGANISM: Unknown
<220> FEATURE:
<223> OTHER INFORMATION: Carboxy-terminal endoplasmic reticulum retention/retrieval signal

<400> SEQUENCE: 52

Lys Lys Glu Leu
1

<210> SEQ ID NO 53
<211> LENGTH: 4
<212> TYPE: PRT
<213> ORGANISM: Unknown
<220> FEATURE:
<223> OTHER INFORMATION: Carboxy-terminal endoplasmic reticulum retention/retrieval signal

<400> SEQUENCE: 53

His Ala Asp Leu
1

<210> SEQ ID NO 54
<211> LENGTH: 4
<212> TYPE: PRT
<213> ORGANISM: Unknown
<220> FEATURE:
<223> OTHER INFORMATION: Carboxy-terminal endoplasmic reticulum retention/retrieval signal

<400> SEQUENCE: 54

His Ala Glu Leu
1

<210> SEQ ID NO 55
<211> LENGTH: 4
<212> TYPE: PRT
<213> ORGANISM: Unknown
<220> FEATURE:
<223> OTHER INFORMATION: Carboxy-terminal endoplasmic reticulum retention/retrieval signal

<400> SEQUENCE: 55

His Ile Glu Leu
1

<210> SEQ ID NO 56
<211> LENGTH: 4
<212> TYPE: PRT
<213> ORGANISM: Unknown
<220> FEATURE:
<223> OTHER INFORMATION: Carboxy-terminal endoplasmic reticulum retention/retrieval signal

<400> SEQUENCE: 56

His Asn Glu Leu
1

<210> SEQ ID NO 57
<211> LENGTH: 4
<212> TYPE: PRT
<213> ORGANISM: Unknown
<220> FEATURE:
<223> OTHER INFORMATION: Carboxy-terminal endoplasmic reticulum retention/retrieval signal

<400> SEQUENCE: 57

His Thr Glu Leu
1

<210> SEQ ID NO 58
<211> LENGTH: 4
<212> TYPE: PRT
<213> ORGANISM: Unknown
<220> FEATURE:
<223> OTHER INFORMATION: Carboxy-terminal endoplasmic reticulum retention/retrieval signal

<400> SEQUENCE: 58

Lys Thr Glu Leu
1

<210> SEQ ID NO 59
<211> LENGTH: 4
<212> TYPE: PRT
<213> ORGANISM: Unknown
<220> FEATURE:
<223> OTHER INFORMATION: Carboxy-terminal endoplasmic reticulum retention/retrieval signal

<400> SEQUENCE: 59

His Val Glu Leu
1

<210> SEQ ID NO 60
<211> LENGTH: 4
<212> TYPE: PRT
<213> ORGANISM: Unknown
<220> FEATURE:
<223> OTHER INFORMATION: Carboxy-terminal endoplasmic reticulum retention/retrieval signal

<400> SEQUENCE: 60

Asn Asp Glu Leu
1

<210> SEQ ID NO 61
<211> LENGTH: 4
<212> TYPE: PRT
<213> ORGANISM: Unknown
<220> FEATURE:
<223> OTHER INFORMATION: Carboxy-terminal endoplasmic reticulum retention/retrieval signal

<400> SEQUENCE: 61

Gln Asp Glu Leu
1

<210> SEQ ID NO 62
<211> LENGTH: 4
<212> TYPE: PRT
<213> ORGANISM: Unknown
<220> FEATURE:
<223> OTHER INFORMATION: Carboxy-terminal endoplasmic reticulum retention/retrieval signal

<400> SEQUENCE: 62

Arg Glu Asp Leu
1

<210> SEQ ID NO 63
<211> LENGTH: 4
<212> TYPE: PRT
<213> ORGANISM: Unknown
<220> FEATURE:
<223> OTHER INFORMATION: Carboxy-terminal endoplasmic reticulum retention/retrieval signal

<400> SEQUENCE: 63

Arg Asn Glu Leu
1

<210> SEQ ID NO 64
<211> LENGTH: 4
<212> TYPE: PRT
<213> ORGANISM: Unknown
<220> FEATURE:
<223> OTHER INFORMATION: Carboxy-terminal endoplasmic reticulum retention/retrieval signal

<400> SEQUENCE: 64

Arg Thr Asp Leu
1

<210> SEQ ID NO 65
<211> LENGTH: 4
<212> TYPE: PRT
<213> ORGANISM: Unknown
<220> FEATURE:
<223> OTHER INFORMATION: Carboxy-terminal endoplasmic reticulum retention/retrieval signal

<400> SEQUENCE: 65

Arg Thr Glu Leu
1

<210> SEQ ID NO 66
<211> LENGTH: 4
<212> TYPE: PRT
<213> ORGANISM: Unknown
<220> FEATURE:
<223> OTHER INFORMATION: Carboxy-terminal endoplasmic reticulum retention/retrieval signal

<400> SEQUENCE: 66

Ser Asp Glu Leu
1

<210> SEQ ID NO 67
<211> LENGTH: 4
<212> TYPE: PRT
<213> ORGANISM: Unknown
<220> FEATURE:
<223> OTHER INFORMATION: Carboxy-terminal endoplasmic reticulum retention/retrieval signal

<400> SEQUENCE: 67

Thr Asp Glu Leu
1

<210> SEQ ID NO 68
<211> LENGTH: 4
<212> TYPE: PRT
<213> ORGANISM: Unknown
<220> FEATURE:
<223> OTHER INFORMATION: Carboxy-terminal endoplasmic reticulum retention/retrieval signal

<400> SEQUENCE: 68

Ser Lys Glu Leu
1

<210> SEQ ID NO 69
<211> LENGTH: 4
<212> TYPE: PRT
<213> ORGANISM: Unknown
<220> FEATURE:
<223> OTHER INFORMATION: Carboxy-terminal endoplasmic reticulum retention/retrieval signal

<400> SEQUENCE: 69

Ser Thr Glu Leu
1

<210> SEQ ID NO 70
<211> LENGTH: 4
<212> TYPE: PRT
<213> ORGANISM: Unknown
<220> FEATURE:
<223> OTHER INFORMATION: Carboxy-terminal endoplasmic reticulum retention/retrieval signal

<400> SEQUENCE: 70

Glu Asp Glu Leu
1

<210> SEQ ID NO 71
<211> LENGTH: 367
<212> TYPE: PRT
<213> ORGANISM: Artificial Sequence
<220> FEATURE:
<223> OTHER INFORMATION: Fusion protein sig10:OKC1-T:OLG1:KDEL

<400> SEQUENCE: 71

```
Met Ala Thr Ser Lys Leu Lys Thr Gln Asn Val Val Val Ser Leu Ser
1               5                   10                  15

Leu Thr Leu Thr Leu Val Leu Val Leu Leu Thr Ser Lys Ala Asn Ser
            20                  25                  30

Gln Glu Gln Asn Gln Glu Gln Pro Ile Arg Cys Glu Lys Asp Glu Arg
        35                  40                  45

Phe Phe Ser Asp Lys Ile Ala Lys Tyr Ile Pro Ile Gln Tyr Val Leu
    50                  55                  60

Ser Arg Tyr Pro Ser Tyr Gly Leu Asn Tyr Tyr Gln Gln Lys Pro Val
65                  70                  75                  80

Ala Leu Ile Asn Asn Gln Phe Leu Pro Tyr Pro Tyr Tyr Ala Lys Pro
                85                  90                  95

Ala Ala Val Arg Ser Pro Ala Gln Ile Leu Gln Trp Gln Val Leu Ser
            100                 105                 110

Asn Thr Val Pro Ala Lys Ser Cys Gln Ala Gln Pro Thr Thr Met Ala
        115                 120                 125

Arg His Pro His Pro His Leu Ser Phe Met Ala Ile Pro Pro Lys Lys
    130                 135                 140

Asn Gln Asp Lys Thr Glu Ile Pro Thr Ile Asn Thr Ile Ala Ser Gly
145                 150                 155                 160

Glu Pro Thr Ser Thr Pro Thr Thr Glu Ala Val Glu Ser Thr Val Ala
                165                 170                 175

Thr Leu Glu Asp Ser Pro Glu Val Ile Glu Ser Pro Pro Glu Ile Asn
            180                 185                 190

Thr Val Gln Val Thr Ser Thr Ala Val Leu Ile Val Thr Gln Thr Met
        195                 200                 205

Lys Gly Leu Asp Ile Gln Lys Val Ala Gly Thr Trp Tyr Ser Leu Ala
    210                 215                 220

Met Ala Ala Ser Asp Ile Ser Leu Leu Asp Ala Gln Ser Ala Pro Leu
225                 230                 235                 240

Arg Val Tyr Val Glu Glu Leu Lys Pro Thr Pro Glu Gly Asp Leu Glu
                245                 250                 255

Ile Leu Leu Gln Lys Trp Glu Asn Gly Glu Cys Ala Gln Lys Lys Ile
            260                 265                 270
```

```
Ile Ala Glu Lys Thr Lys Ile Pro Ala Val Phe Lys Ile Asp Ala Leu
        275                 280                 285

Asn Glu Asn Lys Val Leu Val Leu Asp Thr Asp Tyr Lys Lys Tyr Leu
    290                 295                 300

Leu Phe Cys Met Glu Asn Ser Ala Glu Pro Glu Gln Ser Leu Ala Cys
305                 310                 315                 320

Gln Cys Leu Val Arg Thr Pro Glu Val Asp Asp Glu Ala Leu Glu Lys
                325                 330                 335

Phe Asp Lys Ala Leu Lys Ala Leu Pro Met His Ile Arg Leu Ser Phe
            340                 345                 350

Asn Pro Thr Gln Leu Glu Glu Gln Cys His Ile Lys Asp Glu Leu
        355                 360                 365


<210> SEQ ID NO 72
<211> LENGTH: 1104
<212> TYPE: DNA
<213> ORGANISM: Artificial Sequence
<220> FEATURE:
<223> OTHER INFORMATION: Nucleic acid sequence encoding fusion protein
      sig10:OKC1-T:OLG1:KDEL

<400> SEQUENCE: 72

atggctactt caaagttgaa aacccagaat gtggttgtat ctctctccct aaccttaacc     60

ttggtactgg tgctactgac cagcaaggca aactcacaag agcagaatca agagcagcca    120

atccgttgtg agaaggacga gaggttcttc tcagacaaga tcgccaaata tatacccata    180

caatatgtac tctcacgcta ccctagctac gggcttaact actatcagca aaaacctgta    240

gcactgataa ataaccagtt tctcccctat ccctattatg ctaaacctgc cgccgtgagg    300

agtccagcac aaatacttca gtggcaagtg ctcagtaaca ccgtgccagc aaaaagctgc    360

caggctcagc ccaccacaat ggcccgtcat ccccatcctc accttagctt catggcaatc    420

ccaccaaaga agaatcaaga caagaccgaa atacctacca tcaacacaat tgcatctgga    480

gagcctacca gtacaccaac aactgaggca gtagagtcta ctgttgctac ccttgaggac    540

agccccgagg ttatagagtc cccacctgag ataaataccg tgcaggtgac aagtaccgcc    600

gtattgatcg taacacagac tatgaagggt cttgatatac agaaggtggc cgggacttgg    660

tacagtttgg caatggccgc atccgacatc tccttgttgg acgcacaatc agccccattg    720

cgtgtgtacg tagaagagct taaaccaact cccgaggggg atctggaaat tctgctccag    780

aaatgggaga acggtgagtg cgcccagaag aagatcatcg cagagaagac caaaattcca    840

gcagtattca aaatcgacgc attgaacgaa aataaggtgc tcgtactgga cactgattat    900

aagaagtatc tccttttctg tatggagaac tcagcagagc ctgaacagag tcttgcctgc    960

caatgccttg ttcgtacccc agaggtagat gatgaagctc tggaaaagtt cgataaggcc   1020

cttaaggctc tgcctatgca cattaggctt tctttcaatc caactcaact tgaggaacaa   1080

tgtcacatta aggatgagct ttaa                                          1104


<210> SEQ ID NO 73
<211> LENGTH: 405
<212> TYPE: PRT
<213> ORGANISM: Artificial Sequence
<220> FEATURE:
<223> OTHER INFORMATION: Fusion protein sig10:OBC-T2:FM:OLG1
```

<400> SEQUENCE: 73

```
Met Ala Thr Ser Lys Leu Lys Thr Gln Asn Val Val Val Ser Leu Ser
1               5                   10                  15

Leu Thr Leu Thr Leu Val Leu Val Leu Leu Thr Ser Lys Ala Asn Ser
            20                  25                  30

Arg Glu Leu Glu Glu Leu Asn Val Pro Gly Glu Ile Val Glu Ser Leu
        35                  40                  45

Ser Ser Ser Glu Glu Ser Ile Thr Arg Ile Asn Lys Lys Ile Glu Lys
    50                  55                  60

Phe Gln Ser Glu Glu Gln Gln Gln Thr Glu Asp Glu Leu Gln Asp Lys
65                  70                  75                  80

Ile His Pro Phe Ala Gln Thr Gln Ser Leu Val Tyr Pro Phe Pro Gly
                85                  90                  95

Pro Ile Pro Asn Ser Leu Pro Gln Asn Ile Pro Pro Leu Thr Gln Thr
            100                 105                 110

Pro Val Val Val Pro Pro Phe Leu Gln Pro Glu Val Met Gly Val Ser
        115                 120                 125

Lys Val Lys Glu Ala Met Ala Pro Lys His Lys Glu Met Pro Phe Pro
    130                 135                 140

Lys Tyr Pro Val Glu Pro Phe Thr Glu Ser Gln Ser Leu Thr Leu Thr
145                 150                 155                 160

Asp Val Glu Asn Leu His Leu Pro Leu Pro Leu Leu Gln Ser Trp Met
                165                 170                 175

His Gln Pro His Gln Pro Leu Pro Pro Thr Val Met Phe Pro Pro Gln
            180                 185                 190

Ser Val Leu Ser Leu Ser Gln Ser Lys Val Leu Pro Val Pro Gln Lys
        195                 200                 205

Ala Val Pro Tyr Pro Gln Arg Asp Met Pro Ile Gln Ala Phe Leu Leu
    210                 215                 220

Tyr Gln Glu Pro Val Leu Gly Pro Val Arg Gly Pro Phe Pro Ile Ile
225                 230                 235                 240

Val Phe Met Leu Ile Val Thr Gln Thr Met Lys Gly Leu Asp Ile Gln
                245                 250                 255

Lys Val Ala Gly Thr Trp Tyr Ser Leu Ala Met Ala Ala Ser Asp Ile
            260                 265                 270

Ser Leu Leu Asp Ala Gln Ser Ala Pro Leu Arg Val Tyr Val Glu Glu
        275                 280                 285

Leu Lys Pro Thr Pro Glu Gly Asp Leu Glu Ile Leu Leu Gln Lys Trp
    290                 295                 300

Glu Asn Gly Glu Cys Ala Gln Lys Lys Ile Ile Ala Glu Lys Thr Lys
305                 310                 315                 320

Ile Pro Ala Val Phe Lys Ile Asp Ala Leu Asn Glu Asn Lys Val Leu
                325                 330                 335

Val Leu Asp Thr Asp Tyr Lys Lys Tyr Leu Leu Phe Cys Met Glu Asn
            340                 345                 350

Ser Ala Glu Pro Glu Gln Ser Leu Ala Cys Gln Cys Leu Val Arg Thr
        355                 360                 365

Pro Glu Val Asp Asp Glu Ala Leu Glu Lys Phe Asp Lys Ala Leu Lys
    370                 375                 380

Ala Leu Pro Met His Ile Arg Leu Ser Phe Asn Pro Thr Gln Leu Glu
385                 390                 395                 400

Glu Gln Cys His Ile
                405
```

<210> SEQ ID NO 74
<211> LENGTH: 1218
<212> TYPE: DNA
<213> ORGANISM: Artificial Sequence
<220> FEATURE:
<223> OTHER INFORMATION: Nucleic acid encoding fusion protein sig10:OBC-T2:FM:OLG1

<400> SEQUENCE: 74

```
atggctactt caaagttgaa aacccagaat gtggttgtat ctctctccct aaccttaacc      60

ttggtactgg tgctactgac cagcaaggca aactcacgcg aactggaaga gttgaacgta     120

ccaggagaga ttgtagaatc actgagctcc tcagaggagt ctattactcg tatcaacaag     180

aagatagaga agttccaatc cgaggagcaa caacaaacag aggacgaatt gcaggacaag     240

atacatcctt tcgcacagac ccagagcctc gtctatccct ttccaggtcc aatccctaac     300

tctctccccc agaatatccc acccttgact cagactcccg tggtcgtacc ccctttcttg     360

caacccgagg tgatgggggt ttctaaagtc aaagaggcta tggctcctaa acataaggaa     420

atgccttttc ccaaatatcc agtggagcca ttcactgaga gccagtctct gacacttaca     480

gatgtggaaa acttgcacct gcccttgcca cttttgcagt cctggatgca ccaaccacat     540

caacccttgc cccccacagt gatgtttcct ccacaatcag ttcttagtct ctcccaaagc     600

aaagtccttc cagtgcctca gaaggccgtc ccatacccccc agagagatat gccaatacag     660

gcattcttgc tttaccagga accagtgctc ggtcctgtac gtggcccatt ccctatcata     720

gtgttcatgt tgatcgtaac acagactatg aagggtcttg atatacagaa ggtggccggg     780

acttggtaca gtttggcaat ggccgcatcc gacatctcct tgttggacgc acaatcagcc     840

ccattgcgtg tgtacgtaga agagcttaaa ccaactcccg aggggggatct ggaaattctg     900

ctccagaaat gggagaacgg tgagtgcgcc cagaagaaga tcatcgcaga gaagaccaaa     960

attccagcag tattcaaaat cgacgcattg aacgaaaata aggtgctcgt actggacact    1020

gattataaga agtatctcct tttctgtatg gagaactcag cagagcctga acagagtctt    1080

gcctgccaat gccttgttcg taccccagag gtagatgatg aagctctgga aaagttcgat    1140

aaggccctta aggctctgcc tatgcacatt aggctttctt tcaatccaac tcaacttgag    1200

gaacaatgtc acatttaa                                                  1218
```

<210> SEQ ID NO 75
<211> LENGTH: 395
<212> TYPE: PRT
<213> ORGANISM: Artificial Sequence
<220> FEATURE:
<223> OTHER INFORMATION: Fusion protein sig10:OaS1-T:FM:OLG1

<400> SEQUENCE: 75

```
Met Ala Thr Ser Lys Leu Lys Thr Gln Asn Val Val Val Ser Leu Ser
1               5                   10                  15

Leu Thr Leu Thr Leu Val Leu Val Leu Leu Thr Ser Lys Ala Asn Ser
            20                  25                  30

Arg Pro Lys His Pro Ile Lys His Gln Gly Leu Pro Gln Glu Val Leu
        35                  40                  45

Asn Glu Asn Leu Leu Arg Phe Phe Val Ala Pro Phe Pro Glu Val Phe
    50                  55                  60

Gly Lys Glu Lys Val Asn Glu Leu Ser Lys Asp Ile Gly Ser Glu Ser
65                  70                  75                  80

Thr Glu Asp Gln Ala Met Glu Asp Ile Lys Gln Met Glu Ala Glu Ser
                85                  90                  95
```

```
Ile Ser Ser Ser Glu Glu Ile Val Pro Asn Ser Val Glu Gln Lys His
            100                 105                 110

Ile Gln Lys Glu Asp Val Pro Ser Glu Arg Tyr Leu Gly Tyr Leu Glu
        115                 120                 125

Gln Leu Leu Arg Leu Lys Lys Tyr Lys Val Pro Gln Leu Glu Ile Val
    130                 135                 140

Pro Asn Ser Ala Glu Glu Arg Leu His Ser Met Lys Glu Gly Ile His
145                 150                 155                 160

Ala Gln Gln Lys Glu Pro Met Ile Gly Val Asn Gln Glu Leu Ala Tyr
                165                 170                 175

Phe Tyr Pro Glu Leu Phe Arg Gln Phe Tyr Gln Leu Asp Ala Tyr Pro
            180                 185                 190

Ser Gly Ala Trp Tyr Tyr Val Pro Leu Gly Thr Gln Tyr Thr Asp Ala
        195                 200                 205

Pro Ser Phe Ser Asp Ile Pro Asn Pro Ile Gly Ser Glu Asn Ser Glu
    210                 215                 220

Lys Thr Thr Met Pro Leu Trp Phe Met Leu Ile Val Thr Gln Thr Met
225                 230                 235                 240

Lys Gly Leu Asp Ile Gln Lys Val Ala Gly Thr Trp Tyr Ser Leu Ala
                245                 250                 255

Met Ala Ala Ser Asp Ile Ser Leu Leu Asp Ala Gln Ser Ala Pro Leu
            260                 265                 270

Arg Val Tyr Val Glu Glu Leu Lys Pro Thr Pro Glu Gly Asp Leu Glu
        275                 280                 285

Ile Leu Leu Gln Lys Trp Glu Asn Gly Glu Cys Ala Gln Lys Lys Ile
    290                 295                 300

Ile Ala Glu Lys Thr Lys Ile Pro Ala Val Phe Lys Ile Asp Ala Leu
305                 310                 315                 320

Asn Glu Asn Lys Val Leu Val Leu Asp Thr Asp Tyr Lys Lys Tyr Leu
                325                 330                 335

Leu Phe Cys Met Glu Asn Ser Ala Glu Pro Glu Gln Ser Leu Ala Cys
            340                 345                 350

Gln Cys Leu Val Arg Thr Pro Glu Val Asp Asp Glu Ala Leu Glu Lys
        355                 360                 365

Phe Asp Lys Ala Leu Lys Ala Leu Pro Met His Ile Arg Leu Ser Phe
    370                 375                 380

Asn Pro Thr Gln Leu Glu Glu Gln Cys His Ile
385                 390                 395


<210> SEQ ID NO 76
<211> LENGTH: 1188
<212> TYPE: DNA
<213> ORGANISM: Artificial Sequence
<220> FEATURE:
<223> OTHER INFORMATION: Nucleic acid encoding fusion protein
      sig10:OaS1-T:FM:OLG1

<400> SEQUENCE: 76

atggctactt caaagttgaa aacccagaat gtggttgtat ctctctccct aaccttaacc     60

ttggtactgg tgctactgac cagcaaggca aactcacgcc caaaacatcc cataaaacat    120

caaggattgc cccaggaagt actcaacgag aatctcctcc gttttttcgt tgctcctttc    180

cccgaagtgt tcgggaagga aaaagtaaac gagctttcaa aggacatcgg ctctgaaagt    240

accgaggatc aggctatgga agatatcaag caaatggagg ccgaatctat aagttcttca    300

gaagaaatag ttcccaactc agtggagcag aagcacattc agaaagaaga cgtgcccagc    360
```

```
gagcgctatc tgggatattt ggaacagctg ctcagactga aaaagtacaa ggtgcctcag    420

ctcgaaatcg tacccaatag tgctgaagaa aggttgcact caatgaaaga ggggattcac    480

gcacaacaaa aagagcctat gatcggagta aatcaagaac tggcatactt ttatcccgag    540

ttgtttcgcc aattctatca actggatgcc taccettccg gtgcatggta ctacgtaccc    600

ctcggtactc aatataccga tgctccctcc ttttccgaca ttcctaatcc tataggttcc    660

gagaatagcg aaaagaccac catgccctta tggttcatgt tgatcgtaac acagactatg    720

aagggtcttg atatacagaa ggtggccggg acttggtaca gtttggcaat ggccgcatcc    780

gacatctcct tgttggacgc acaatcagcc ccattgcgtg tgtacgtaga agagcttaaa    840

ccaactcccg agggggatct ggaaattctg ctccagaaat gggagaacgg tgagtgcgcc    900

cagaagaaga tcatcgcaga gaagaccaaa attccagcag tattcaaaat cgacgcattg    960

aacgaaaata aggtgctcgt actggacact gattataaga agtatctcct tttctgtatg   1020

gagaactcag cagagcctga acagagtctt gcctgccaat gccttgttcg taccccagag   1080

gtagatgatg aagctctgga aaagttcgat aaggccctta aggctctgcc tatgcacatt   1140

aggctttctt tcaatccaac tcaacttgag gaacaatgtc acatttaa                1188
```

```
<210> SEQ ID NO 77
<211> LENGTH: 304
<212> TYPE: PRT
<213> ORGANISM: Artificial Sequence
<220> FEATURE:
<223> OTHER INFORMATION: Fusion protein sig10:paraOKC1-T:FM:OLG1:KDEL

<400> SEQUENCE: 77

Met Ala Thr Ser Lys Leu Lys Thr Gln Asn Val Val Val Ser Leu Ser
1               5                   10                  15

Leu Thr Leu Thr Leu Val Leu Val Leu Leu Thr Ser Lys Ala Asn Ser
            20                  25                  30

Gln Glu Gln Asn Gln Glu Gln Pro Ile Arg Cys Glu Lys Asp Glu Arg
        35                  40                  45

Phe Phe Ser Asp Lys Ile Ala Lys Tyr Ile Pro Ile Gln Tyr Val Leu
    50                  55                  60

Ser Arg Tyr Pro Ser Tyr Gly Leu Asn Tyr Tyr Gln Gln Lys Pro Val
65                  70                  75                  80

Ala Leu Ile Asn Asn Gln Phe Leu Pro Tyr Pro Tyr Tyr Ala Lys Pro
                85                  90                  95

Ala Ala Val Arg Ser Pro Ala Gln Ile Leu Gln Trp Gln Val Leu Ser
            100                 105                 110

Asn Thr Val Pro Ala Lys Ser Cys Gln Ala Gln Pro Thr Thr Met Ala
        115                 120                 125

Arg His Pro His Pro His Leu Ser Phe Met Leu Ile Val Thr Gln Thr
    130                 135                 140

Met Lys Gly Leu Asp Ile Gln Lys Val Ala Gly Thr Trp Tyr Ser Leu
145                 150                 155                 160

Ala Met Ala Ala Ser Asp Ile Ser Leu Leu Asp Ala Gln Ser Ala Pro
                165                 170                 175

Leu Arg Val Tyr Val Glu Glu Leu Lys Pro Thr Pro Glu Gly Asp Leu
            180                 185                 190

Glu Ile Leu Leu Gln Lys Trp Glu Asn Gly Glu Cys Ala Gln Lys Lys
        195                 200                 205

Ile Ile Ala Glu Lys Thr Lys Ile Pro Ala Val Phe Lys Ile Asp Ala
    210                 215                 220
```

```
Leu Asn Glu Asn Lys Val Leu Val Leu Asp Thr Asp Tyr Lys Lys Tyr
225                 230                 235                 240

Leu Leu Phe Cys Met Glu Asn Ser Ala Glu Pro Glu Gln Ser Leu Ala
                245                 250                 255

Cys Gln Cys Leu Val Arg Thr Pro Glu Val Asp Asp Glu Ala Leu Glu
            260                 265                 270

Lys Phe Asp Lys Ala Leu Lys Ala Leu Pro Met His Ile Arg Leu Ser
        275                 280                 285

Phe Asn Pro Thr Gln Leu Glu Glu Gln Cys His Ile Lys Asp Glu Leu
    290                 295                 300


<210> SEQ ID NO 78
<211> LENGTH: 915
<212> TYPE: DNA
<213> ORGANISM: Artificial Sequence
<220> FEATURE:
<223> OTHER INFORMATION: Nucleic acid encoding fusion protein
      sig10:paraOKC1-T:FM:OLG1:KDEL

<400> SEQUENCE: 78

atggctactt caaagttgaa aacccagaat gtggttgtat ctctctccct aaccttaacc      60

ttggtactgg tgctactgac cagcaaggca aactcacaag agcagaatca agagcagcca     120

atccgttgtg agaaggacga gaggttcttc tcagacaaga tcgccaaata tataccccata     180

caatatgtac tctcacgcta ccctagctac gggcttaact actatcagca aaaacctgta     240

gcactgataa ataaccagtt tctcccctat ccctattatg ctaaacctgc cgccgtgagg     300

agtccagcac aaatacttca gtggcaagtg ctcagtaaca ccgtgccagc aaaaagctgc     360

caggctcagc ccaccacaat ggcccgtcat ccccatcctc accttagctt catgttgatc     420

gtaacacaga ctatgaaggg tcttgatata cagaaggtgg ccgggacttg gtacagtttg     480

gcaatggccg catccgacat ctccttgttg gacgcacaat cagcccccatt gcgtgtgtac     540

gtagaagagc ttaaaccaac tcccgagggg gatctggaaa ttctgctcca gaaatgggag     600

aacggtgagt gcgcccagaa gaagatcatc gcagagaaga ccaaaattcc agcagtattc     660

aaaatcgacg cattgaacga aaataaggtg ctcgtactgg acactgatta taagaagtat     720

ctccttttct gtatggagaa ctcagcagag cctgaacaga gtcttgcctg ccaatgcctt     780

gttcgtaccc cagaggtaga tgatgaagct ctggaaaagt tcgataaggc ccttaaggct     840

ctgcctatgc acattaggct ttctttcaat ccaactcaac ttgaggaaca atgtcacatt     900

aaggatgagc tttaa                                                      915


<210> SEQ ID NO 79
<211> LENGTH: 300
<212> TYPE: PRT
<213> ORGANISM: Artificial Sequence
<220> FEATURE:
<223> OTHER INFORMATION: Fusion protein sig10:paraOKC1-T:FM:OLG1

<400> SEQUENCE: 79

Met Ala Thr Ser Lys Leu Lys Thr Gln Asn Val Val Val Ser Leu Ser
1               5                   10                  15

Leu Thr Leu Thr Leu Val Leu Val Leu Leu Thr Ser Lys Ala Asn Ser
            20                  25                  30

Gln Glu Gln Asn Gln Glu Gln Pro Ile Arg Cys Glu Lys Asp Glu Arg
        35                  40                  45

Phe Phe Ser Asp Lys Ile Ala Lys Tyr Ile Pro Ile Gln Tyr Val Leu
    50                  55                  60
```

```
Ser Arg Tyr Pro Ser Tyr Gly Leu Asn Tyr Tyr Gln Gln Lys Pro Val
65                  70                  75                  80

Ala Leu Ile Asn Asn Gln Phe Leu Pro Tyr Pro Tyr Tyr Ala Lys Pro
                85                  90                  95

Ala Ala Val Arg Ser Pro Ala Gln Ile Leu Gln Trp Gln Val Leu Ser
            100                 105                 110

Asn Thr Val Pro Ala Lys Ser Cys Gln Ala Gln Pro Thr Thr Met Ala
        115                 120                 125

Arg His Pro His Pro His Leu Ser Phe Met Leu Ile Val Thr Gln Thr
    130                 135                 140

Met Lys Gly Leu Asp Ile Gln Lys Val Ala Gly Thr Trp Tyr Ser Leu
145                 150                 155                 160

Ala Met Ala Ala Ser Asp Ile Ser Leu Leu Asp Ala Gln Ser Ala Pro
                165                 170                 175

Leu Arg Val Tyr Val Glu Glu Leu Lys Pro Thr Pro Glu Gly Asp Leu
            180                 185                 190

Glu Ile Leu Leu Gln Lys Trp Glu Asn Gly Glu Cys Ala Gln Lys Lys
        195                 200                 205

Ile Ile Ala Glu Lys Thr Lys Ile Pro Ala Val Phe Lys Ile Asp Ala
    210                 215                 220

Leu Asn Glu Asn Lys Val Leu Val Leu Asp Thr Asp Tyr Lys Lys Tyr
225                 230                 235                 240

Leu Leu Phe Cys Met Glu Asn Ser Ala Glu Pro Glu Gln Ser Leu Ala
                245                 250                 255

Cys Gln Cys Leu Val Arg Thr Pro Glu Val Asp Asp Glu Ala Leu Glu
            260                 265                 270

Lys Phe Asp Lys Ala Leu Lys Ala Leu Pro Met His Ile Arg Leu Ser
        275                 280                 285

Phe Asn Pro Thr Gln Leu Glu Glu Gln Cys His Ile
    290                 295                 300
```

```
<210> SEQ ID NO 80
<211> LENGTH: 903
<212> TYPE: DNA
<213> ORGANISM: Artificial Sequence
<220> FEATURE:
<223> OTHER INFORMATION: Nucleic acid encoding fusion protein
      sig10:paraOKC1-T:FM:OLG1

<400> SEQUENCE: 80

atggctactt caaagttgaa aacccagaat gtggttgtat ctctctccct aaccttaacc     60

ttggtactgg tgctactgac cagcaaggca aactcacaag agcagaatca agagcagcca    120

atccgttgtg agaaggacga gaggttcttc tcagacaaga tcgccaaata tataccccata    180

caatatgtac tctcacgcta ccctagctac gggcttaact actatcagca aaaacctgta    240

gcactgataa ataaccagtt tctcccctat ccctattatg ctaaacctgc cgccgtgagg    300

agtccagcac aaatacttca gtggcaagtg ctcagtaaca ccgtgccagc aaaaagctgc    360

caggctcagc ccaccacaat ggcccgtcat ccccatcctc accttagctt catgttgatc    420

gtaacacaga ctatgaaggg tcttgatata cagaaggtgg ccgggacttg gtacagtttg    480

gcaatggccg catccgacat ctccttgttg gacgcacaat cagccccatt gcgtgtgtac    540

gtagaagagc ttaaaccaac tcccgagggg gatctggaaa ttctgctcca gaaatgggag    600

aacggtgagt gcgcccagaa gaagatcatc gcagagaaga ccaaaattcc agcagtattc    660

aaaatcgacg cattgaacga aaataaggtg ctcgtactgg acactgatta taagaagtat    720
```

```
ctccttttct gtatggagaa ctcagcagag cctgaacaga gtcttgcctg ccaatgcctt    780

gttcgtaccc cagaggtaga tgatgaagct ctggaaaagt tcgataaggc ccttaaggct    840

ctgcctatgc acattaggct ttctttcaat ccaactcaac ttgaggaaca atgtcacatt    900

taa                                                                  903


<210> SEQ ID NO 81
<211> LENGTH: 354
<212> TYPE: PRT
<213> ORGANISM: Artificial Sequence
<220> FEATURE:
<223> OTHER INFORMATION: Fusion protein sig2:OKC1-T:OLG1:KDEL

<400> SEQUENCE: 81

Met Ala Lys Leu Val Phe Ser Leu Cys Phe Leu Leu Phe Ser Gly Cys
1               5                   10                  15

Cys Phe Ala Gln Glu Gln Asn Gln Glu Gln Pro Ile Arg Cys Glu Lys
            20                  25                  30

Asp Glu Arg Phe Phe Ser Asp Lys Ile Ala Lys Tyr Ile Pro Ile Gln
        35                  40                  45

Tyr Val Leu Ser Arg Tyr Pro Ser Tyr Gly Leu Asn Tyr Tyr Gln Gln
    50                  55                  60

Lys Pro Val Ala Leu Ile Asn Asn Gln Phe Leu Pro Tyr Pro Tyr Tyr
65                  70                  75                  80

Ala Lys Pro Ala Ala Val Arg Ser Pro Ala Gln Ile Leu Gln Trp Gln
                85                  90                  95

Val Leu Ser Asn Thr Val Pro Ala Lys Ser Cys Gln Ala Gln Pro Thr
            100                 105                 110

Thr Met Ala Arg His Pro His Pro His Leu Ser Phe Met Ala Ile Pro
        115                 120                 125

Pro Lys Lys Asn Gln Asp Lys Thr Glu Ile Pro Thr Ile Asn Thr Ile
    130                 135                 140

Ala Ser Gly Glu Pro Thr Ser Thr Pro Thr Thr Glu Ala Val Glu Ser
145                 150                 155                 160

Thr Val Ala Thr Leu Glu Asp Ser Pro Glu Val Ile Glu Ser Pro Pro
                165                 170                 175

Glu Ile Asn Thr Val Gln Val Thr Ser Thr Ala Val Leu Ile Val Thr
            180                 185                 190

Gln Thr Met Lys Gly Leu Asp Ile Gln Lys Val Ala Gly Thr Trp Tyr
        195                 200                 205

Ser Leu Ala Met Ala Ala Ser Asp Ile Ser Leu Leu Asp Ala Gln Ser
    210                 215                 220

Ala Pro Leu Arg Val Tyr Val Glu Glu Leu Lys Pro Thr Pro Glu Gly
225                 230                 235                 240

Asp Leu Glu Ile Leu Leu Gln Lys Trp Glu Asn Gly Glu Cys Ala Gln
                245                 250                 255

Lys Lys Ile Ile Ala Glu Lys Thr Lys Ile Pro Ala Val Phe Lys Ile
            260                 265                 270

Asp Ala Leu Asn Glu Asn Lys Val Leu Val Leu Asp Thr Asp Tyr Lys
        275                 280                 285

Lys Tyr Leu Leu Phe Cys Met Glu Asn Ser Ala Glu Pro Glu Gln Ser
    290                 295                 300

Leu Ala Cys Gln Cys Leu Val Arg Thr Pro Glu Val Asp Asp Glu Ala
305                 310                 315                 320
```

```
Leu Glu Lys Phe Asp Lys Ala Leu Lys Ala Leu Pro Met His Ile Arg
                325                 330                 335

Leu Ser Phe Asn Pro Thr Gln Leu Glu Glu Gln Cys His Ile Lys Asp
            340                 345                 350

Glu Leu
```

<210> SEQ ID NO 82
<211> LENGTH: 1065
<212> TYPE: DNA
<213> ORGANISM: Artificial Sequence
<220> FEATURE:
<223> OTHER INFORMATION: Nucleic acid encoding fusion protein sig2:OKC1-T:OLG1:KDEL

<400> SEQUENCE: 82

```
atggccaagc tagtttttc cctttgtttt ctgcttttca gtggctgctg cttcgctcaa      60

gagcagaatc aagagcagcc aatccgttgt gagaaggacg agaggttctt ctcagacaag    120

atcgccaaat atatacccat acaatatgta ctctcacgct accctagcta cgggcttaac    180

tactatcagc aaaaacctgt agcactgata aataaccagt ttctcccta tccctattat    240

gctaaacctg ccgccgtgag gagtccagca caaatacttc agtggcaagt gctcagtaac    300

accgtgccag caaaaagctg ccaggctcag cccaccacaa tggcccgtca tccccatcct    360

caccttagct tcatggcaat cccaccaaag aagaatcaag acaagaccga aatacctacc    420

atcaacacaa ttgcatctgg agagcctacc agtacaccaa caactgaggc agtagagtct    480

actgttgcta cccttgagga cagccccgag gttatagagt ccccacctga gataaatacc    540

gtgcaggtga caagtaccgc cgtattgatc gtaacacaga ctatgaaggg tcttgatata    600

cagaaggtgg ccgggacttg gtacagtttg gcaatggccg catccgacat ctccttgttg    660

gacgcacaat cagccccatt gcgtgtgtac gtagaagagc ttaaaccaac tcccgagggg    720

gatctggaaa ttctgctcca gaaatgggag aacggtgagt gcgcccagaa gaagatcatc    780

gcagagaaga ccaaaattcc agcagtattc aaaatcgacg cattgaacga aaataaggtg    840

ctcgtactgg acactgatta taagaagtat ctccttttct gtatggagaa ctcagcagag    900

cctgaacaga gtcttgcctg ccaatgcctt gttcgtaccc cagaggtaga tgatgaagct    960

ctggaaaagt tcgataaggc ccttaaggct ctgcctatgc acattaggct ttctttcaat   1020

ccaactcaac ttgaggaaca atgtcacatt aaggatgagc tttaa                   1065
```

<210> SEQ ID NO 83
<211> LENGTH: 621
<212> TYPE: PRT
<213> ORGANISM: Artificial Sequence
<220> FEATURE:
<223> OTHER INFORMATION: Optimized alpha S2-casein truncated version 1(OaS2-T)

<400> SEQUENCE: 83

```
Ala Ala Gly Ala Ala Thr Ala Cys Thr Ala Thr Gly Gly Ala Ala Cys
1               5                   10                  15

Ala Cys Gly Thr Ala Ala Gly Cys Thr Cys Ala Ala Gly Thr Gly Ala
            20                  25                  30

Ala Gly Ala Ala Thr Cys Thr Ala Thr Ala Ala Thr Ala Ala Gly Thr
        35                  40                  45

Cys Ala Ala Gly Ala Gly Ala Cys Ala Thr Ala Thr Ala Ala Gly Cys
    50                  55                  60
```

Ala Ala Gly Ala Gly Ala Ala Ala Ala Ala Cys Ala Thr Gly Gly Cys
65 70 75 80

Ala Ala Thr Ala Ala Ala Thr Cys Cys Cys Thr Cys Cys Ala Ala Gly
85 90 95

Gly Ala Gly Ala Ala Thr Cys Thr Thr Thr Gly Thr Ala Gly Cys Ala
100 105 110

Cys Thr Thr Thr Thr Thr Gly Cys Ala Ala Ala Gly Ala Ala Gly Thr
115 120 125

Thr Gly Thr Gly Ala Gly Ala Ala Ala Thr Gly Cys Ala Ala Ala Thr
130 135 140

Gly Ala Gly Gly Ala Ala Gly Ala Ala Thr Ala Cys Thr Cys Ala Ala
145 150 155 160

Thr Ala Gly Gly Cys Ala Gly Cys Thr Cys Thr Thr Cys Cys Gly Ala
165 170 175

Ala Gly Ala Ala Thr Cys Thr Gly Cys Thr Gly Ala Ala Gly Thr Cys
180 185 190

Gly Cys Thr Ala Cys Thr Gly Ala Ala Gly Ala Gly Gly Thr Cys Ala
195 200 205

Ala Ala Ala Thr Ala Ala Cys Ala Gly Thr Thr Gly Ala Cys Gly Ala
210 215 220

Cys Ala Ala Gly Cys Ala Thr Thr Ala Thr Cys Ala Ala Ala Ala Ala
225 230 235 240

Gly Cys Cys Cys Thr Gly Ala Ala Thr Gly Ala Ala Ala Thr Ala Ala
245 250 255

Ala Cys Cys Ala Gly Thr Thr Cys Thr Ala Cys Cys Ala Ala Ala Ala
260 265 270

Ala Thr Thr Thr Cys Cys Cys Cys Ala Ala Thr Ala Cys Cys Thr Cys
275 280 285

Cys Ala Gly Thr Ala Cys Cys Thr Thr Thr Ala Thr Cys Ala Ala Gly
290 295 300

Gly Ala Cys Cys Cys Ala Thr Ala Gly Thr Cys Cys Thr Cys Ala Ala
305 310 315 320

Cys Cys Cys Thr Thr Gly Gly Gly Ala Thr Cys Ala Gly Gly Thr Cys
325 330 335

Ala Ala Gly Cys Gly Thr Ala Ala Thr Gly Cys Thr Gly Thr Thr Cys
340 345 350

Cys Ala Ala Thr Ala Ala Cys Ala Cys Cys Ala Ala Cys Ala Cys Thr
355 360 365

Cys Ala Ala Thr Cys Gly Thr Gly Ala Ala Cys Ala Ala Cys Thr Gly
370 375 380

Thr Cys Thr Ala Cys Cys Thr Cys Ala Gly Ala Ala Gly Ala Ala Ala
385 390 395 400

Ala Thr Thr Cys Cys Ala Ala Ala Ala Ala Ala Ala Cys Thr Gly Thr
405 410 415

Gly Gly Ala Thr Ala Thr Gly Gly Ala Ala Ala Gly Thr Ala Cys Ala
420 425 430

Gly Ala Ala Gly Thr Thr Thr Thr Thr Ala Cys Thr Ala Ala Ala Ala
435 440 445

Ala Gly Ala Cys Cys Ala Ala Gly Cys Thr Cys Ala Cys Cys Gly Ala
450 455 460

Gly Gly Ala Gly Gly Ala Ala Ala Ala Ala Ala Ala Thr Ala Gly Ala
465 470 475 480

Thr Thr Gly Ala Ala Thr Thr Thr Thr Cys Thr Thr Ala Ala Gly Ala
485 490 495

Ala Gly Ala Thr Cys Ala Gly Thr Cys Ala Ala Cys Gly Cys Thr Ala
500 505 510

Thr Cys Ala Gly Ala Ala Gly Thr Thr Cys Gly Cys Cys Cys Thr Thr
515 520 525

Cys Cys Ala Cys Ala Ala Thr Ala Cys Cys Thr Cys Ala Ala Gly Ala
530 535 540

Cys Thr Gly Thr Ala Thr Ala Cys Cys Ala Ala Cys Ala Thr Cys Ala
545 550 555 560

Gly Ala Ala Gly Gly Cys Cys Ala Thr Gly Ala Ala Gly Cys Cys Thr
565 570 575

Thr Gly Gly Ala Thr Thr Cys Ala Gly Cys Cys Cys Ala Ala Ala Ala
580 585 590

Cys Ala Ala Ala Gly Gly Thr Ala Ala Thr Cys Cys Cys Cys Thr Ala
595 600 605

Thr Gly Thr Thr Ala Gly Ala Thr Ala Cys Thr Thr Gly
610 615 620

<210> SEQ ID NO 84
<211> LENGTH: 207
<212> TYPE: PRT
<213> ORGANISM: Artificial Sequence
<220> FEATURE:
<223> OTHER INFORMATION: Optimized alpha S2-casein truncated version 1(OaS2-T)

<400> SEQUENCE: 84

Lys Asn Thr Met Glu His Val Ser Ser Ser Glu Glu Ser Ile Ile Ser
1 5 10 15

Gln Glu Thr Tyr Lys Gln Glu Lys Asn Met Ala Ile Asn Pro Ser Lys
20 25 30

Glu Asn Leu Cys Ser Thr Phe Cys Lys Glu Val Val Arg Asn Ala Asn
35 40 45

Glu Glu Glu Tyr Ser Ile Gly Ser Ser Ser Glu Glu Ser Ala Glu Val
50 55 60

Ala Thr Glu Glu Val Lys Ile Thr Val Asp Asp Lys His Tyr Gln Lys
65 70 75 80

Ala Leu Asn Glu Ile Asn Gln Phe Tyr Gln Lys Phe Pro Gln Tyr Leu
85 90 95

Gln Tyr Leu Tyr Gln Gly Pro Ile Val Leu Asn Pro Trp Asp Gln Val
100 105 110

Lys Arg Asn Ala Val Pro Ile Thr Pro Thr Leu Asn Arg Glu Gln Leu
115 120 125

Ser Thr Ser Glu Glu Asn Ser Lys Lys Thr Val Asp Met Glu Ser Thr
130 135 140

Glu Val Phe Thr Lys Lys Thr Lys Leu Thr Glu Glu Glu Lys Asn Arg
145 150 155 160

Leu Asn Phe Leu Lys Lys Ile Ser Gln Arg Tyr Gln Lys Phe Ala Leu
165 170 175

Pro Gln Tyr Leu Lys Thr Val Tyr Gln His Gln Lys Ala Met Lys Pro
180 185 190

Trp Ile Gln Pro Lys Thr Lys Val Ile Pro Tyr Val Arg Tyr Leu
195 200 205

<210> SEQ ID NO 85
<211> LENGTH: 171
<212> TYPE: PRT
<213> ORGANISM: Capra hircus

<400> SEQUENCE: 85

Gln Glu Gln Asn Gln Glu Gln Pro Ile Cys Cys Glu Lys Asp Glu Arg
1 5 10 15

Phe Phe Asp Asp Lys Ile Ala Lys Tyr Ile Pro Ile Gln Tyr Val Leu
20 25 30

Ser Arg Tyr Pro Ser Tyr Gly Leu Asn Tyr Tyr Gln Gln Arg Pro Val
35 40 45

Ala Leu Ile Asn Asn Gln Phe Leu Pro Tyr Pro Tyr Tyr Ala Lys Pro
50 55 60

Val Ala Val Arg Ser Pro Ala Gln Thr Leu Gln Trp Gln Val Leu Pro
65 70 75 80

Asn Thr Val Pro Ala Lys Ser Cys Gln Asp Gln Pro Thr Thr Leu Ala
85 90 95

Arg His Pro His Pro His Leu Ser Phe Met Ala Ile Pro Pro Lys Lys
100 105 110

Asp Gln Asp Lys Thr Glu Val Pro Ala Ile Asn Thr Ile Ala Ser Ala
115 120 125

Glu Pro Thr Val His Ser Thr Pro Thr Thr Glu Ala Ile Val Asn Thr
130 135 140

Val Asp Asn Pro Glu Ala Ser Ser Glu Ser Ile Ala Ser Ala Ser Glu
145 150 155 160

Thr Asn Thr Ala Gln Val Thr Ser Thr Glu Val
165 170

<210> SEQ ID NO 86
<211> LENGTH: 171
<212> TYPE: PRT
<213> ORGANISM: Ovis aries

<400> SEQUENCE: 86

Gln Glu Gln Asn Gln Glu Gln Arg Ile Cys Cys Glu Lys Asp Glu Arg
1 5 10 15

Phe Phe Asp Asp Lys Ile Ala Lys Tyr Ile Pro Ile Gln Tyr Val Leu
20 25 30

Ser Arg Tyr Pro Ser Tyr Gly Leu Asn Tyr Tyr Gln Gln Arg Pro Val
35 40 45

Ala Leu Ile Asn Asn Gln Phe Leu Pro Tyr Pro Tyr Tyr Ala Lys Pro
50 55 60

Val Ala Val Arg Ser Pro Ala Gln Thr Leu Gln Trp Gln Val Leu Pro
65 70 75 80

Asn Ala Val Pro Ala Lys Ser Cys Gln Asp Gln Pro Thr Ala Met Ala
85 90 95

Arg His Pro His Pro His Leu Ser Phe Met Ala Ile Pro Pro Lys Lys
100 105 110

Asp Gln Asp Lys Thr Glu Ile Pro Ala Ile Asn Thr Ile Ala Ser Ala
115 120 125

Glu Pro Thr Val His Ser Thr Pro Thr Thr Glu Ala Val Val Asn Ala
130 135 140

```
Val Asp Asn Pro Glu Ala Ser Ser Glu Ser Ile Ala Ser Ala Pro Glu
145                 150                 155                 160

Thr Asn Thr Ala Gln Val Thr Ser Thr Glu Val
                165                 170


<210> SEQ ID NO 87
<211> LENGTH: 165
<212> TYPE: PRT
<213> ORGANISM: Bubalus bubalis

<400> SEQUENCE: 87

Gln Glu Gln Asn Gln Glu Gln Pro Ile Arg Cys Glu Lys Glu Glu Arg
1               5                   10                  15

Phe Phe Asn Asp Lys Ile Ala Lys Tyr Ile Pro Ile Gln Tyr Val Leu
            20                  25                  30

Ser Arg Tyr Pro Ser Tyr Gly Leu Asn Tyr Tyr Gln Gln Lys Pro Val
        35                  40                  45

Ala Leu Ile Asn Asn Gln Phe Leu Pro Tyr Pro Tyr Tyr Ala Lys Pro
    50                  55                  60

Ala Ala Val Arg Ser Pro Ala Gln Ile Leu Gln Trp Gln Val Leu Pro
65                  70                  75                  80

Asn Thr Val Pro Ala Lys Ser Cys Gln Ala Gln Pro Thr Thr Met Thr
                85                  90                  95

Arg His Pro His Pro His Leu Ser Phe Met Ala Ile Pro Pro Lys Lys
            100                 105                 110

Asn Gln Asp Lys Thr Glu Ile Pro Thr Ile Asn Thr Ile Val Ser Val
        115                 120                 125

Glu Pro Thr Ser Thr Pro Thr Thr Glu Ala Ile Glu Asn Thr Val Ala
    130                 135                 140

Thr Leu Glu Ala Ser Ser Glu Val Ile Glu Ser Val Pro Glu Thr Asn
145                 150                 155                 160

Thr Ala Gln Val Thr
                165


<210> SEQ ID NO 88
<211> LENGTH: 162
<212> TYPE: PRT
<213> ORGANISM: Camelus dromedaries

<400> SEQUENCE: 88

Glu Val Gln Asn Gln Glu Gln Pro Thr Cys Phe Glu Lys Val Glu Arg
1               5                   10                  15

Leu Leu Asn Glu Lys Thr Val Lys Tyr Phe Pro Ile Gln Phe Val Gln
            20                  25                  30

Ser Arg Tyr Pro Ser Tyr Gly Ile Asn Tyr Tyr Gln His Arg Leu Ala
        35                  40                  45

Val Pro Ile Asn Asn Gln Phe Ile Pro Tyr Pro Asn Tyr Ala Lys Pro
    50                  55                  60

Val Ala Ile Arg Leu His Ala Gln Ile Pro Gln Cys Gln Ala Leu Pro
65                  70                  75                  80

Asn Ile Asp Pro Pro Thr Val Glu Arg Arg Pro Arg Pro Arg Pro Ser
                85                  90                  95

Phe Ile Ala Ile Pro Pro Lys Lys Thr Gln Asp Lys Thr Val Asn Pro
            100                 105                 110

Ala Ile Asn Thr Val Ala Thr Val Glu Pro Pro Val Ile Pro Thr Ala
        115                 120                 125
```

```
Glu Pro Ala Val Asn Thr Val Val Ile Ala Glu Ala Ser Ser Glu Phe
    130                 135                 140

Ile Thr Thr Ser Thr Pro Glu Thr Thr Thr Val Gln Ile Thr Ser Thr
145                 150                 155                 160

Glu Ile


<210> SEQ ID NO 89
<211> LENGTH: 162
<212> TYPE: PRT
<213> ORGANISM: Camelus bactrianus

<400> SEQUENCE: 89

Glu Val Gln Asn Gln Glu Gln Pro Thr Cys Cys Glu Lys Val Glu Arg
1               5                   10                  15

Leu Leu Asn Glu Lys Thr Val Lys Tyr Phe Pro Ile Gln Phe Val Gln
            20                  25                  30

Ser Arg Tyr Pro Ser Tyr Gly Ile Asn Tyr Tyr Gln His Arg Leu Ala
        35                  40                  45

Val Pro Ile Asn Asn Gln Phe Ile Pro Tyr Pro Asn Tyr Ala Lys Pro
    50                  55                  60

Val Ala Ile Arg Leu His Ala Gln Ile Pro Gln Cys Gln Ala Leu Pro
65                  70                  75                  80

Asn Ile Asp Pro Pro Thr Val Glu Arg Arg Pro Arg Pro Arg Pro Ser
                85                  90                  95

Phe Ile Ala Ile Pro Pro Lys Lys Thr Gln Asp Lys Thr Val Asn Pro
            100                 105                 110

Ala Ile Asn Thr Val Ala Thr Val Glu Pro Pro Val Ile Pro Thr Ala
        115                 120                 125

Glu Pro Ala Val Asn Thr Val Val Ile Ala Glu Ala Ser Ser Glu Phe
    130                 135                 140

Ile Thr Thr Ser Thr Pro Glu Thr Thr Thr Val Gln Ile Thr Ser Thr
145                 150                 155                 160

Glu Ile


<210> SEQ ID NO 90
<211> LENGTH: 173
<212> TYPE: PRT
<213> ORGANISM: Bos mutus

<400> SEQUENCE: 90

Gln Glu Gln Asn Gln Glu Gln Pro Ile Arg Cys Glu Lys Asp Glu Arg
1               5                   10                  15

Phe Phe Ser Asp Lys Ile Ala Lys Tyr Ile Pro Ile Gln Tyr Val Leu
            20                  25                  30

Ser Arg Tyr Pro Ser Tyr Gly Leu Asn Tyr Tyr Gln Gln Lys Pro Val
        35                  40                  45

Ala Leu Ile Asn Asn Gln Phe Leu Pro Tyr Pro Tyr Tyr Ala Lys Pro
    50                  55                  60

Ala Ala Val Arg Ser Pro Ala Gln Ile Leu Gln Trp Gln Val Leu Ser
65                  70                  75                  80

Asn Thr Val Pro Ala Lys Ser Cys Gln Ala Gln Pro Thr Thr Met Ala
                85                  90                  95

Arg His Pro His Pro His Leu Ser Phe Met Ala Ile Pro Pro Lys Lys
            100                 105                 110

Asn Gln Asp Lys Thr Glu Ile Pro Thr Ile Asn Thr Ile Ala Ser Gly
        115                 120                 125
```

```
Glu Pro Thr Ser Thr Pro Thr Thr Glu Ala Val Glu Ser Thr Val Ala
    130                 135                 140

Thr Leu Glu Ala Ser Pro Glu Ala Ser Pro Glu Val Ile Glu Ser Pro
145                 150                 155                 160

Pro Glu Ile Asn Thr Val Gln Val Thr Ser Thr Ala Val
                165                 170


<210> SEQ ID NO 91
<211> LENGTH: 165
<212> TYPE: PRT
<213> ORGANISM: Equus caballus

<400> SEQUENCE: 91

Glu Val Gln Asn Gln Glu Gln Pro Thr Cys His Lys Asn Asp Glu Arg
1               5                   10                  15

Phe Phe Asp Leu Lys Thr Val Lys Tyr Ile Pro Ile Tyr Tyr Val Leu
            20                  25                  30

Asn Ser Ser Pro Arg Tyr Glu Pro Ile Tyr Tyr Gln His Arg Leu Ala
        35                  40                  45

Leu Leu Ile Asn Asn Gln His Met Pro Tyr Gln Tyr Tyr Ala Arg Pro
    50                  55                  60

Ala Ala Val Arg Pro His Val Gln Ile Pro Gln Trp Gln Val Leu Pro
65                  70                  75                  80

Asn Ile Tyr Pro Ser Thr Val Val Arg His Pro Cys Pro His Pro Ser
                85                  90                  95

Phe Ile Ala Ile Pro Pro Lys Lys Leu Gln Glu Ile Thr Val Ile Pro
            100                 105                 110

Lys Ile Asn Thr Ile Ala Thr Val Glu Pro Thr Pro Ile Pro Thr Pro
        115                 120                 125

Glu Pro Thr Val Asn Asn Ala Val Ile Pro Asp Ala Ser Ser Glu Phe
    130                 135                 140

Ile Ile Ala Ser Thr Pro Glu Thr Thr Thr Val Pro Val Thr Ser Pro
145                 150                 155                 160

Val Val Gln Lys Leu
                165


<210> SEQ ID NO 92
<211> LENGTH: 162
<212> TYPE: PRT
<213> ORGANISM: Equus asinus

<400> SEQUENCE: 92

Glu Val Gln Asn Gln Glu Gln Pro Thr Cys Arg Lys Asn Asp Glu Arg
1               5                   10                  15

Phe Phe Asp Leu Lys Thr Val Lys Tyr Ile Pro Ile Tyr Tyr Val Leu
            20                  25                  30

Asn Ser Ser Pro Arg Asn Glu Pro Ile Tyr Tyr Gln His Arg Leu Ala
        35                  40                  45

Val Leu Ile Asn Asn Gln His Met Pro Tyr Gln Tyr Tyr Ala Arg Pro
    50                  55                  60

Ala Ala Val Arg Pro His Val Gln Ile Pro Gln Trp Gln Val Leu Pro
65                  70                  75                  80

Asn Ile Tyr Pro Ser Thr Val Val Arg His Pro Arg Pro His Pro Ser
                85                  90                  95

Phe Ile Ala Ile Pro Pro Lys Lys Leu Gln Glu Lys Thr Val Ile Pro
            100                 105                 110
```

```
Lys Ile Asn Thr Ile Ala Thr Val Glu Pro Thr Pro Ile Pro Thr Pro
        115                 120                 125

Glu Pro Thr Val Asn Asn Ala Val Ile Pro Asp Ala Ser Ser Glu Phe
    130                 135                 140

Ile Ile Ala Ser Thr Pro Glu Thr Thr Thr Val Pro Val Thr Ser Pro
145                 150                 155                 160

Val Val


<210> SEQ ID NO 93
<211> LENGTH: 122
<212> TYPE: PRT
<213> ORGANISM: Rangifer tarandus

<400> SEQUENCE: 93

Val Ala Leu Ile Asn Asn Gln Phe Leu Pro Tyr Pro Tyr Tyr Ala Lys
1               5                   10                  15

Pro Gly Ala Val Arg Ser Pro Ala Gln Ile Leu Gln Trp Gln Val Leu
            20                  25                  30

Pro Asn Thr Val Pro Ala Lys Ser Cys Gln Ala Gln Pro Thr Thr Leu
        35                  40                  45

Ala Arg His Pro His Pro Arg Leu Ser Phe Met Ala Ile Pro Pro Lys
    50                  55                  60

Lys Asn Gln Asp Lys Thr Asp Ile Pro Thr Ile Asn Thr Ile Ala Thr
65                  70                  75                  80

Val Glu Ser Thr Ile Thr Pro Thr Thr Glu Ala Ile Val Asp Thr Val
                85                  90                  95

Ala Thr Leu Glu Ala Ser Ser Glu Val Ile Glu Ser Ala Pro Glu Thr
            100                 105                 110

Asn Thr Asp Gln Val Thr Ser Thr Val Val
        115                 120


<210> SEQ ID NO 94
<211> LENGTH: 141
<212> TYPE: PRT
<213> ORGANISM: Alces alces

<400> SEQUENCE: 94

Lys Ile Val Lys Tyr Ile Pro Ile Gln Tyr Ala Leu Ser Arg Tyr Pro
1               5                   10                  15

Ser Tyr Gly Leu Ser Tyr Tyr Gln His Arg Pro Val Ala Leu Ile Asn
            20                  25                  30

Asn Gln Phe Leu Pro Tyr Pro Tyr Tyr Ala Lys Pro Gly Ala Val Arg
        35                  40                  45

Ser Pro Ala Gln Ile Leu Gln Trp Gln Val Leu Pro Asn Thr Val Pro
    50                  55                  60

Ala Lys Ser Cys Gln Ala Gln Pro Thr Thr Met Ala Arg His Pro Arg
65                  70                  75                  80

Pro Arg Leu Ser Phe Met Ala Ile Pro Pro Lys Lys Asn Gln Asp Lys
                85                  90                  95

Thr Asp Ile Pro Thr Ile Asn Thr Ile Ala Thr Val Glu Ser Thr Ile
            100                 105                 110

Thr Pro Thr Thr Glu Ala Ile Glu Asp Asn Val Ala Thr Leu Glu Ala
        115                 120                 125

Ser Ser Glu Val Ile Glu Ser Ala Pro Glu Thr Asn Thr
    130                 135                 140
```

```
<210> SEQ ID NO 95
<211> LENGTH: 162
<212> TYPE: PRT
<213> ORGANISM: Vicugna pacos

<400> SEQUENCE: 95

Glu Val Gln Asn Gln Glu Gln Pro Thr Cys Cys Glu Lys Val Glu Arg
1               5                   10                  15

Leu Leu Asn Glu Lys Thr Val Lys Tyr Phe Pro Ile Gln Phe Val Gln
            20                  25                  30

Ser Arg Tyr Pro Ser Tyr Gly Ile Asn Tyr Tyr Gln His Arg Leu Ala
        35                  40                  45

Val Pro Ile Asn Asn Gln Phe Ile Pro Tyr Pro Asn Tyr Ala Lys Pro
    50                  55                  60

Val Ala Ile Arg Leu His Ala Gln Ile Pro Gln Cys Gln Ala Leu Pro
65                  70                  75                  80

Asn Ile Asp Pro Pro Thr Val Glu Arg Arg Pro Arg Pro Arg Pro Ser
                85                  90                  95

Phe Ile Ala Ile Pro Pro Lys Lys Thr Gln Asp Lys Thr Val Ile Pro
            100                 105                 110

Ala Ile Asn Thr Val Ala Thr Ala Glu Pro Pro Val Ile Pro Thr Ala
        115                 120                 125

Glu Pro Val Val Asn Thr Val Val Ile Ala Glu Ala Ser Ser Glu Phe
    130                 135                 140

Ile Thr Thr Ser Thr Pro Glu Thr Thr Thr Val Gln Ile Thr Ser Thr
145                 150                 155                 160

Glu Ile


<210> SEQ ID NO 96
<211> LENGTH: 160
<212> TYPE: PRT
<213> ORGANISM: Bos indicus

<400> SEQUENCE: 96

Arg Cys Glu Lys Asp Glu Arg Phe Phe Ser Asp Lys Ile Ala Lys Tyr
1               5                   10                  15

Ile Pro Ile Gln Tyr Val Leu Ser Arg Tyr Pro Ser Tyr Gly Leu Asn
            20                  25                  30

Tyr Tyr Gln Gln Lys Pro Val Ala Leu Ile Asn Asn Gln Phe Leu Pro
        35                  40                  45

Tyr Pro Tyr Tyr Ala Lys Pro Ala Ala Val Arg Ser Pro Ala Gln Ile
    50                  55                  60

Leu Gln Trp Gln Val Leu Ser Asn Thr Val Pro Ala Lys Ser Cys Gln
65                  70                  75                  80

Ala Gln Pro Thr Thr Met Ala Arg His Pro His Pro His Leu Ser Phe
                85                  90                  95

Met Ala Ile Pro Pro Lys Lys Asn Gln Asp Lys Thr Glu Ile Pro Thr
            100                 105                 110

Ile Asn Thr Ile Ala Ser Gly Glu Pro Thr Ser Thr Pro Thr Thr Glu
        115                 120                 125

Ala Val Glu Ser Thr Val Ala Thr Leu Glu Asp Ser Pro Glu Val Ile
    130                 135                 140

Glu Ser Pro Pro Glu Ile Asn Thr Val Gln Val Thr Ser Thr Ala Val
145                 150                 155                 160
```

<210> SEQ ID NO 97
<211> LENGTH: 162
<212> TYPE: PRT
<213> ORGANISM: Lama glama

<400> SEQUENCE: 97

```
Glu Val Gln Asn Gln Glu Gln Pro Thr Cys Cys Glu Lys Val Glu Arg
1               5                   10                  15

Leu Leu Asn Glu Lys Thr Val Lys Tyr Phe Pro Ile Gln Phe Val Gln
            20                  25                  30

Ser Arg Tyr Pro Ser Tyr Gly Ile Asn Tyr Tyr Gln His Arg Leu Ala
        35                  40                  45

Val Pro Ile Asn Asn Gln Phe Ile Pro Tyr Pro Asn Tyr Ala Lys Pro
    50                  55                  60

Val Ala Ile Arg Leu His Ala Gln Ile Pro Gln Cys Gln Ala Leu Pro
65                  70                  75                  80

Asn Ile Asp Pro Pro Thr Val Glu Arg Arg Pro Arg Pro Arg Pro Ser
                85                  90                  95

Phe Ile Ala Ile Pro Pro Lys Lys Thr Gln Asp Lys Thr Val Ile Pro
            100                 105                 110

Ala Ile Asn Thr Val Ala Thr Val Glu Pro Pro Val Ile Pro Thr Ala
        115                 120                 125

Glu Pro Val Val Asn Thr Val Val Ile Ala Glu Ala Ser Ser Glu Phe
    130                 135                 140

Ile Thr Thr Ser Thr Pro Glu Thr Thr Thr Val Gln Ile Thr Ser Thr
145                 150                 155                 160

Glu Ile
```

<210> SEQ ID NO 98
<211> LENGTH: 162
<212> TYPE: PRT
<213> ORGANISM: Homo sapiens

<400> SEQUENCE: 98

```
Glu Val Gln Asn Gln Lys Gln Pro Ala Cys His Glu Asn Asp Glu Arg
1               5                   10                  15

Pro Phe Tyr Gln Lys Thr Ala Pro Tyr Val Pro Met Tyr Tyr Val Pro
            20                  25                  30

Asn Ser Tyr Pro Tyr Tyr Gly Thr Asn Leu Tyr Gln Arg Arg Pro Ala
        35                  40                  45

Ile Ala Ile Asn Asn Pro Tyr Val Pro Arg Thr Tyr Tyr Ala Asn Pro
    50                  55                  60

Ala Val Val Arg Pro His Ala Gln Ile Pro Gln Arg Gln Tyr Leu Pro
65                  70                  75                  80

Asn Ser His Pro Pro Thr Val Val Arg Arg Pro Asn Leu His Pro Ser
                85                  90                  95

Phe Ile Ala Ile Pro Pro Lys Lys Ile Gln Asp Lys Ile Ile Ile Pro
            100                 105                 110

Thr Ile Asn Thr Ile Ala Thr Val Glu Pro Thr Pro Ala Pro Ala Thr
        115                 120                 125

Glu Pro Thr Val Asp Ser Val Val Thr Pro Glu Ala Phe Ser Glu Ser
    130                 135                 140

Ile Ile Thr Ser Thr Pro Glu Thr Thr Thr Val Ala Val Thr Pro Pro
145                 150                 155                 160

Thr Ala
```

```
<210> SEQ ID NO 99
<211> LENGTH: 199
<212> TYPE: PRT
<213> ORGANISM: Capra hircus

<400> SEQUENCE: 99

Arg Pro Lys His Pro Ile Asn His Arg Gly Leu Ser Pro Glu Val Pro
1               5                   10                  15

Asn Glu Asn Leu Leu Arg Phe Val Val Ala Pro Phe Pro Glu Val Phe
            20                  25                  30

Arg Lys Glu Asn Ile Asn Glu Leu Ser Lys Asp Ile Gly Ser Glu Ser
        35                  40                  45

Thr Glu Asp Gln Ala Met Glu Asp Ala Lys Gln Met Lys Ala Gly Ser
    50                  55                  60

Ser Ser Ser Ser Glu Glu Ile Val Pro Asn Ser Ala Glu Gln Lys Tyr
65                  70                  75                  80

Ile Gln Lys Glu Asp Val Pro Ser Glu Arg Tyr Leu Gly Tyr Leu Glu
                85                  90                  95

Gln Leu Leu Arg Leu Lys Lys Tyr Asn Val Pro Gln Leu Glu Ile Val
            100                 105                 110

Pro Lys Ser Ala Glu Glu Gln Leu His Ser Met Lys Glu Gly Asn Pro
        115                 120                 125

Ala His Gln Lys Gln Pro Met Ile Ala Val Asn Gln Glu Leu Ala Tyr
    130                 135                 140

Phe Tyr Pro Gln Leu Phe Arg Gln Phe Tyr Gln Leu Asp Ala Tyr Pro
145                 150                 155                 160

Ser Gly Ala Trp Tyr Tyr Leu Pro Leu Gly Thr Gln Tyr Thr Asp Ala
                165                 170                 175

Pro Ser Phe Ser Asp Ile Pro Asn Pro Ile Gly Ser Glu Asn Ser Gly
            180                 185                 190

Lys Thr Thr Met Pro Leu Trp
        195


<210> SEQ ID NO 100
<211> LENGTH: 199
<212> TYPE: PRT
<213> ORGANISM: Ovis aris

<400> SEQUENCE: 100

Arg Pro Lys His Pro Ile Lys His Gln Gly Leu Ser Ser Glu Val Leu
1               5                   10                  15

Asn Glu Asn Leu Leu Arg Phe Val Val Ala Pro Phe Pro Glu Val Phe
            20                  25                  30

Arg Lys Glu Asn Ile Asn Glu Leu Ser Lys Asp Ile Gly Ser Glu Ser
        35                  40                  45

Ile Glu Asp Gln Ala Met Glu Asp Ala Lys Gln Met Lys Ala Gly Ser
    50                  55                  60

Ser Ser Ser Ser Glu Glu Ile Val Pro Asn Ser Ala Glu Gln Lys Tyr
65                  70                  75                  80

Ile Gln Lys Glu Asp Val Pro Ser Glu Arg Tyr Leu Gly Tyr Leu Glu
                85                  90                  95

Gln Leu Leu Arg Leu Lys Lys Tyr Asn Val Pro Gln Leu Glu Ile Val
            100                 105                 110

Pro Lys Ser Ala Glu Glu Gln Leu His Ser Met Lys Glu Gly Asn Pro
        115                 120                 125
```

```
Ala His Gln Lys Gln Pro Met Ile Ala Val Asn Gln Glu Leu Ala Tyr
    130                 135                 140

Phe Tyr Pro Gln Leu Phe Arg Gln Phe Tyr Gln Leu Asp Ala Tyr Pro
145                 150                 155                 160

Ser Gly Ala Trp Tyr Tyr Leu Pro Leu Gly Thr Gln Tyr Thr Asp Ala
                165                 170                 175

Pro Ser Phe Ser Asp Ile Pro Asn Pro Ile Gly Ser Glu Asn Ser Gly
            180                 185                 190

Lys Ile Thr Met Pro Leu Trp
        195


<210> SEQ ID NO 101
<211> LENGTH: 199
<212> TYPE: PRT
<213> ORGANISM: Bubalus bubalis

<400> SEQUENCE: 101

Arg Pro Lys Gln Pro Ile Lys His Gln Gly Leu Pro Gln Gly Val Leu
1               5                   10                  15

Asn Glu Asn Leu Leu Arg Phe Phe Val Ala Pro Phe Pro Glu Val Phe
            20                  25                  30

Gly Lys Glu Lys Val Asn Glu Leu Ser Thr Asp Ile Gly Ser Glu Ser
        35                  40                  45

Thr Glu Asp Gln Ala Met Glu Asp Ile Lys Gln Met Glu Ala Glu Ser
    50                  55                  60

Ile Ser Ser Ser Glu Glu Ile Val Pro Ile Ser Val Glu Gln Lys His
65                  70                  75                  80

Ile Gln Lys Glu Asp Val Pro Ser Glu Arg Tyr Leu Gly Tyr Leu Glu
                85                  90                  95

Gln Leu Leu Arg Leu Lys Lys Tyr Asn Val Pro Gln Leu Glu Ile Val
            100                 105                 110

Pro Asn Leu Ala Glu Glu Gln Leu His Ser Met Lys Glu Gly Ile His
        115                 120                 125

Ala Gln Gln Lys Glu Pro Met Ile Gly Val Asn Gln Glu Leu Ala Tyr
    130                 135                 140

Phe Tyr Pro Gln Leu Phe Arg Gln Phe Tyr Gln Leu Asp Ala Tyr Pro
145                 150                 155                 160

Ser Gly Ala Trp Tyr Tyr Val Pro Leu Gly Thr Gln Tyr Pro Asp Ala
                165                 170                 175

Pro Ser Phe Ser Asp Ile Pro Asn Pro Ile Gly Ser Glu Asn Ser Gly
            180                 185                 190

Lys Thr Thr Met Pro Leu Trp
        195


<210> SEQ ID NO 102
<211> LENGTH: 154
<212> TYPE: PRT
<213> ORGANISM: Camelus dromedaries

<400> SEQUENCE: 102

Asp Thr Glu Arg Lys Glu Ser Gly Ser Ser Ser Ser Glu Glu Val Val
1               5                   10                  15

Ser Ser Thr Thr Glu Gln Lys Asp Ile Leu Lys Glu Asp Met Pro Ser
            20                  25                  30

Gln Arg Tyr Leu Glu Glu Leu His Arg Leu Asn Lys Tyr Lys Leu Leu
        35                  40                  45
```

```
Gln Leu Glu Ala Ile Arg Asp Gln Lys Leu Ile Pro Arg Val Lys Leu
    50                  55                  60

Ser Ser His Pro Tyr Leu Glu Gln Leu Tyr Arg Ile Asn Glu Asp Asn
65                  70                  75                  80

His Pro Gln Leu Gly Glu Pro Val Lys Val Val Thr Gln Glu Gln Ala
                85                  90                  95

Tyr Phe His Leu Glu Pro Phe Pro Gln Phe Phe Gln Leu Gly Ala Ser
            100                 105                 110

Pro Tyr Val Ala Trp Tyr Tyr Pro Pro Gln Val Met Gln Tyr Ile Ala
        115                 120                 125

His Pro Ser Ser Tyr Asp Thr Pro Glu Gly Ile Ala Ser Glu Asp Gly
    130                 135                 140

Gly Lys Thr Asp Val Met Pro Gln Trp Trp
145                 150


<210> SEQ ID NO 103
<211> LENGTH: 207
<212> TYPE: PRT
<213> ORGANISM: Camelus bactrianus

<400> SEQUENCE: 103

Arg Pro Lys Tyr Pro Leu Arg Tyr Pro Glu Val Phe Gln Asn Glu Pro
1               5                   10                  15

Asp Ser Ile Glu Glu Val Leu Asn Lys Arg Lys Ile Leu Glu Leu Ala
            20                  25                  30

Val Val Ser Pro Ile Gln Phe Arg Gln Glu Asn Ile Asp Glu Leu Lys
        35                  40                  45

Asp Thr Arg Asn Glu Pro Thr Glu Asp His Ile Met Glu Asp Thr Glu
    50                  55                  60

Arg Lys Glu Ser Gly Ser Ser Ser Ser Glu Glu Val Val Ser Ser Thr
65                  70                  75                  80

Thr Glu Gln Lys Asp Ile Leu Lys Glu Asp Met Pro Ser Gln Arg Tyr
                85                  90                  95

Leu Glu Glu Leu His Arg Leu Asn Lys Tyr Lys Leu Leu Gln Leu Glu
            100                 105                 110

Ala Ile Arg Asp Gln Lys Leu Ile Pro Arg Val Lys Leu Ser Ser His
        115                 120                 125

Pro Tyr Leu Glu Gln Leu Tyr Arg Ile Asn Glu Asp Asn His Pro Gln
    130                 135                 140

Leu Gly Glu Pro Val Lys Val Val Thr Gln Pro Phe Pro Gln Phe Phe
145                 150                 155                 160

Gln Leu Gly Ala Ser Pro Tyr Val Ala Trp Tyr Tyr Pro Pro Gln Val
                165                 170                 175

Met Gln Tyr Ile Ala His Pro Ser Ser Tyr Asp Thr Pro Glu Gly Ile
            180                 185                 190

Ala Ser Glu Asp Gly Gly Lys Thr Asp Val Met Pro Gln Trp Trp
        195                 200                 205


<210> SEQ ID NO 104
<211> LENGTH: 199
<212> TYPE: PRT
<213> ORGANISM: Bos mutus
```

<400> SEQUENCE: 104

```
Arg Pro Lys His Pro Ile Lys His Gln Gly Leu Pro Gln Glu Val Leu
1               5                   10                  15

Asn Glu Asn Leu Leu Arg Phe Phe Val Ala Pro Phe Pro Glu Val Phe
            20                  25                  30

Gly Lys Glu Lys Val Asn Glu Leu Ser Lys Asp Ile Gly Ser Glu Ser
        35                  40                  45

Thr Glu Asp Gln Ala Met Glu Asp Ile Lys Gln Met Glu Ala Glu Ser
    50                  55                  60

Ile Ser Ser Ser Glu Glu Ile Val Pro Asn Ser Val Glu Gln Lys His
65                  70                  75                  80

Ile Gln Lys Glu Asp Val Pro Ser Glu His Tyr Leu Gly Tyr Leu Glu
                85                  90                  95

Gln Leu Leu Arg Leu Lys Lys Tyr Lys Val Pro Gln Leu Glu Ile Val
            100                 105                 110

Pro Asn Ser Ala Glu Glu Arg Leu His Ser Met Lys Glu Gly Ile His
        115                 120                 125

Ala Gln Gln Lys Glu Pro Met Ile Gly Val Asn Gln Glu Leu Ala Tyr
    130                 135                 140

Phe Tyr Pro Glu Leu Phe Arg Gln Phe Tyr Gln Leu Asp Ala Tyr Pro
145                 150                 155                 160

Ser Gly Ala Trp Tyr Tyr Val Pro Leu Gly Thr Gln Tyr Thr Asp Ala
                165                 170                 175

Pro Ser Phe Ser Asp Ile Pro Asn Pro Ile Gly Ser Glu Asn Ser Gly
            180                 185                 190

Lys Thr Thr Met Pro Leu Trp
        195
```

<210> SEQ ID NO 105
<211> LENGTH: 226
<212> TYPE: PRT
<213> ORGANISM: Equus caballus

<400> SEQUENCE: 105

```
Arg Glu Lys Glu Glu Leu Asn Val Ser Ser Glu Thr Val Glu Ser Leu
1               5                   10                  15

Ser Ser Asn Glu Pro Asp Ser Ser Ser Glu Glu Ser Ile Thr His Ile
            20                  25                  30

Asn Lys Glu Lys Leu Gln Lys Phe Lys His Glu Gly Gln Gln Gln Arg
        35                  40                  45

Glu Val Glu Arg Gln Asp Lys Ile Ser Arg Phe Val Gln Pro Gln Pro
    50                  55                  60

Val Val Tyr Pro Tyr Ala Glu Pro Val Pro Tyr Ala Val Val Pro Gln
65                  70                  75                  80

Ser Ile Leu Pro Leu Ala Gln Pro Pro Ile Leu Pro Phe Leu Gln Pro
                85                  90                  95

Glu Ile Met Glu Val Ser Gln Ala Lys Glu Thr Ile Leu Pro Lys Arg
            100                 105                 110

Lys Val Met Pro Phe Leu Lys Ser Pro Ile Val Pro Phe Ser Glu Arg
        115                 120                 125

Gln Ile Leu Asn Pro Thr Asn Gly Glu Asn Leu Arg Leu Pro Val His
    130                 135                 140

Leu Ile Gln Pro Phe Met His Gln Val Pro Gln Ser Leu Leu Gln Thr
145                 150                 155                 160
```

```
Leu Met Leu Pro Ser Gln Pro Val Leu Ser Pro Pro Gln Ser Lys Val
                165                 170                 175

Ala Pro Phe Pro Gln Pro Val Val Pro Tyr Pro Gln Arg Asp Thr Pro
            180                 185                 190

Val Gln Ala Phe Leu Leu Tyr Gln Asp Pro Arg Leu Gly Pro Thr Gly
        195                 200                 205

Glu Leu Asp Pro Ala Thr Gln Pro Ile Val Ala Val His Asn Pro Val
    210                 215                 220

Ile Val
225


<210> SEQ ID NO 106
<211> LENGTH: 202
<212> TYPE: PRT
<213> ORGANISM: Equus asinus

<400> SEQUENCE: 106

Arg Pro Lys Leu Pro His Arg His Pro Glu Ile Ile Gln Asn Glu Gln
1               5                   10                  15

Asp Ser Arg Glu Lys Val Leu Lys Glu Arg Lys Phe Pro Ser Phe Ala
            20                  25                  30

Leu His Thr Pro Arg Glu Glu Tyr Ile Asn Glu Leu Asn Arg Gln Arg
        35                  40                  45

Glu Leu Leu Lys Glu Lys Gln Lys Asp Glu His Lys Glu Tyr Leu Ile
    50                  55                  60

Glu Asp Pro Glu Gln Gln Glu Ser Ser Ser Thr Ser Ser Ser Glu Glu
65                  70                  75                  80

Val Val Pro Ile Asn Thr Glu Gln Lys Arg Ile Pro Arg Glu Asp Met
                85                  90                  95

Leu Tyr Gln His Thr Leu Glu Gln Leu Arg Arg Leu Ser Lys Tyr Asn
            100                 105                 110

Gln Leu Gln Leu Gln Ala Ile Tyr Ala Gln Glu Gln Leu Ile Arg Met
        115                 120                 125

Lys Glu Asn Ser Gln Arg Lys Pro Met Arg Val Val Asn Gln Glu Gln
    130                 135                 140

Ala Tyr Phe Tyr Leu Glu Pro Phe Gln Pro Ser Tyr Gln Leu Asp Val
145                 150                 155                 160

Tyr Pro Tyr Ala Ala Trp Phe His Pro Ala Gln Ile Met Gln His Val
                165                 170                 175

Ala Tyr Ser Pro Phe His Asp Thr Ala Lys Leu Ile Ala Ser Glu Asn
            180                 185                 190

Ser Glu Lys Thr Asp Ile Ile Pro Glu Trp
        195                 200


<210> SEQ ID NO 107
<211> LENGTH: 199
<212> TYPE: PRT
<213> ORGANISM: Bos indicus
<220> FEATURE:
<221> NAME/KEY: misc_feature
<222> LOCATION: (84)..(84)
<223> OTHER INFORMATION: Xaa can be any naturally occurring amino acid

<400> SEQUENCE: 107

Arg Pro Lys His Pro Ile Lys His Gln Gly Leu Pro Gln Glu Val Leu
1               5                   10                  15

Asn Glu Asn Leu Leu Arg Phe Phe Val Ala Pro Phe Pro Glu Val Phe
            20                  25                  30
```

```
Gly Lys Glu Lys Val Asn Glu Leu Ser Lys Asp Ile Gly Ser Glu Ser
        35                  40                  45

Thr Glu Asp Gln Ala Met Glu Asp Ile Lys Gln Met Glu Ala Glu Ser
    50                  55                  60

Ile Ser Ser Ser Glu Glu Ile Val Pro Asn Ser Val Glu Gln Lys His
65                  70                  75                  80

Ile Gln Lys Xaa Asp Val Pro Ser Glu Arg Tyr Leu Gly Tyr Leu Glu
                85                  90                  95

Gln Leu Leu Arg Leu Lys Lys Tyr Lys Val Pro Gln Leu Glu Ile Val
            100                 105                 110

Pro Asn Ser Ala Glu Glu Arg Leu His Ser Met Lys Glu Gly Ile His
        115                 120                 125

Ala Gln Gln Lys Glu Pro Met Ile Gly Val Asn Gln Glu Leu Ala Tyr
    130                 135                 140

Phe Tyr Pro Glu Leu Phe Arg Gln Phe Tyr Gln Leu Asp Ala Tyr Pro
145                 150                 155                 160

Ser Gly Ala Trp Tyr Tyr Val Pro Leu Gly Thr Gln Tyr Thr Asp Ala
                165                 170                 175

Pro Ser Phe Ser Asp Ile Pro Asn Pro Ile Gly Ser Glu Asn Ser Gly
            180                 185                 190

Lys Thr Thr Met Pro Leu Trp
        195


<210> SEQ ID NO 108
<211> LENGTH: 215
<212> TYPE: PRT
<213> ORGANISM: Lama glama

<400> SEQUENCE: 108

Arg Pro Lys Tyr Pro Leu Arg Tyr Pro Glu Val Phe Gln Asn Glu Pro
1               5                   10                  15

Asp Ser Ile Gln Glu Val Leu Asn Lys Arg Lys Ile Leu Glu Leu Ala
            20                  25                  30

Val Val Ser Pro Ile Gln Phe Arg Gln Glu Asn Ile Asp Glu Leu Lys
        35                  40                  45

Asp Thr Arg Asn Glu Pro Thr Glu Asp His Ile Met Glu Asp Thr Glu
    50                  55                  60

Arg Thr Val Ser Gly Ser Ser Ser Ser Glu Glu Val Val Ser Ser Thr
65                  70                  75                  80

Thr Glu Gln Lys Asp Ile Leu Lys Glu Asp Met Pro Ser Gln Arg Ile
                85                  90                  95

Leu Glu Glu Leu His Arg Leu Asn Lys Tyr Lys Leu Leu Gln Leu Glu
            100                 105                 110

Ala Ile Arg Asp Gln Lys Leu Ile Pro Arg Val Lys Leu Ser Ser His
        115                 120                 125

Pro Tyr Leu Glu Gln Leu Tyr Arg Ile Asn Glu Asp Asn His Pro Gln
    130                 135                 140

Leu Gly Glu Pro Val Lys Val Val Thr Gln Glu Gln Ala Tyr Phe His
145                 150                 155                 160

Leu Glu Pro Phe Gln Gln Phe Phe Gln Leu Gly Ala Ser Pro Tyr Val
                165                 170                 175

Ala Trp Tyr Tyr Pro Pro Gln Val Met Gln Tyr Ile Ala His Pro Ser
            180                 185                 190
```

```
Ser His Asp Thr Pro Glu Gly Ile Ala Ser Glu Asp Gly Gly Lys Thr
        195                 200                 205

Asp Val Met Pro Gln Trp Trp
    210                 215


<210> SEQ ID NO 109
<211> LENGTH: 170
<212> TYPE: PRT
<213> ORGANISM: Homo sapiens

<400> SEQUENCE: 109

Arg Pro Lys Leu Pro Leu Arg Tyr Pro Glu Arg Leu Gln Asn Pro Ser
1               5                   10                  15

Glu Ser Ser Glu Pro Ile Pro Leu Glu Ser Arg Glu Glu Tyr Met Asn
            20                  25                  30

Gly Met Asn Arg Gln Arg Asn Ile Leu Arg Glu Lys Gln Thr Asp Glu
        35                  40                  45

Ile Lys Asp Thr Arg Asn Glu Ser Thr Gln Asn Cys Val Val Ala Glu
    50                  55                  60

Pro Glu Lys Met Glu Ser Ser Ile Ser Ser Ser Ser Glu Glu Met Ser
65                  70                  75                  80

Leu Ser Lys Cys Ala Glu Gln Phe Cys Arg Leu Asn Glu Tyr Asn Gln
                85                  90                  95

Leu Gln Leu Gln Ala Ala His Ala Gln Glu Gln Ile Arg Arg Met Asn
            100                 105                 110

Glu Asn Ser His Val Gln Val Pro Phe Gln Gln Leu Asn Gln Leu Ala
        115                 120                 125

Ala Tyr Pro Tyr Ala Val Trp Tyr Tyr Pro Gln Ile Met Gln Tyr Val
    130                 135                 140

Pro Phe Pro Pro Phe Ser Asp Ile Ser Asn Pro Thr Ala His Glu Asn
145                 150                 155                 160

Tyr Glu Lys Asn Asn Val Met Leu Gln Trp
                165                 170


<210> SEQ ID NO 110
<211> LENGTH: 208
<212> TYPE: PRT
<213> ORGANISM: Capra hircus

<400> SEQUENCE: 110

Lys His Lys Met Glu His Val Ser Ser Ser Glu Glu Pro Ile Asn Ile
1               5                   10                  15

Phe Gln Glu Ile Tyr Lys Gln Glu Lys Asn Met Ala Ile His Pro Arg
            20                  25                  30

Lys Glu Lys Leu Cys Thr Thr Ser Cys Glu Glu Val Val Arg Asn Ala
        35                  40                  45

Asn Glu Glu Glu Tyr Ser Ile Arg Ser Ser Ser Glu Glu Ser Ala Glu
    50                  55                  60

Val Ala Pro Glu Glu Ile Lys Ile Thr Val Asp Asp Lys His Tyr Gln
65                  70                  75                  80

Lys Ala Leu Asn Glu Ile Asn Gln Phe Tyr Gln Lys Phe Pro Gln Tyr
                85                  90                  95

Leu Gln Tyr Pro Tyr Gln Gly Pro Ile Val Leu Asn Pro Trp Asp Gln
            100                 105                 110

Val Lys Arg Asn Ala Gly Pro Phe Thr Pro Thr Val Asn Arg Glu Gln
        115                 120                 125
```

```
Leu Ser Thr Ser Glu Glu Asn Ser Lys Lys Thr Ile Asp Met Glu Ser
    130                 135                 140

Thr Glu Val Phe Thr Lys Lys Thr Lys Leu Thr Glu Glu Glu Lys Asn
145                 150                 155                 160

Arg Leu Asn Phe Leu Lys Lys Ile Ser Gln Tyr Tyr Gln Lys Phe Ala
                165                 170                 175

Trp Pro Gln Tyr Leu Lys Thr Val Asp Gln His Gln Lys Ala Met Lys
            180                 185                 190

Pro Trp Thr Gln Pro Lys Thr Asn Ala Ile Pro Tyr Val Arg Tyr Leu
        195                 200                 205


<210> SEQ ID NO 111
<211> LENGTH: 208
<212> TYPE: PRT
<213> ORGANISM: Ovis aries

<400> SEQUENCE: 111

Lys His Lys Met Glu His Val Ser Ser Ser Glu Glu Pro Ile Asn Ile
1               5                   10                  15

Ser Gln Glu Ile Tyr Lys Gln Glu Lys Asn Met Ala Ile His Pro Arg
            20                  25                  30

Lys Glu Lys Leu Cys Thr Thr Ser Cys Glu Glu Val Val Arg Asn Ala
        35                  40                  45

Asp Glu Glu Glu Tyr Ser Ile Arg Ser Ser Ser Glu Glu Ser Ala Glu
    50                  55                  60

Val Ala Pro Glu Glu Val Lys Ile Thr Val Asp Asp Lys His Tyr Gln
65                  70                  75                  80

Lys Ala Leu Asn Glu Ile Asn Gln Phe Tyr Gln Lys Phe Pro Gln Tyr
                85                  90                  95

Leu Gln Tyr Leu Tyr Gln Gly Pro Ile Val Leu Asn Pro Trp Asp Gln
            100                 105                 110

Val Lys Arg Asn Ala Gly Pro Phe Thr Pro Thr Val Asn Arg Glu Gln
        115                 120                 125

Leu Ser Thr Ser Glu Glu Asn Ser Lys Lys Thr Ile Asp Met Glu Ser
    130                 135                 140

Thr Glu Val Phe Thr Lys Lys Thr Lys Leu Thr Glu Glu Glu Lys Asn
145                 150                 155                 160

Arg Leu Asn Phe Leu Lys Lys Ile Ser Gln Tyr Tyr Gln Lys Phe Ala
                165                 170                 175

Trp Pro Gln Tyr Leu Lys Thr Val Asp Gln His Gln Lys Ala Met Lys
            180                 185                 190

Pro Trp Thr Gln Pro Lys Thr Asn Ala Ile Pro Tyr Val Arg Tyr Leu
        195                 200                 205


<210> SEQ ID NO 112
<211> LENGTH: 207
<212> TYPE: PRT
<213> ORGANISM: Bubalus bubalis

<400> SEQUENCE: 112

Lys His Thr Met Glu His Val Ser Ser Ser Glu Glu Ser Ile Ile Ser
1               5                   10                  15

Gln Glu Thr Tyr Lys Gln Glu Lys Asn Met Ala Ile His Pro Ser Lys
            20                  25                  30

Glu Asn Leu Cys Ser Thr Phe Cys Lys Glu Val Ile Arg Asn Ala Asn
        35                  40                  45
```

```
Glu Glu Glu Tyr Ser Ile Gly Ser Ser Ser Glu Glu Ser Ala Glu Val
    50                  55                  60

Ala Thr Glu Glu Val Lys Ile Thr Val Asp Asp Lys His Tyr Gln Lys
65                  70                  75                  80

Ala Leu Asn Glu Ile Asn Gln Phe Tyr Gln Lys Phe Pro Gln Tyr Leu
                85                  90                  95

Gln Tyr Leu Tyr Gln Gly Pro Ile Val Leu Asn Pro Trp Asp Gln Val
            100                 105                 110

Lys Arg Asn Ala Val Pro Ile Thr Pro Thr Leu Asn Arg Glu Gln Leu
        115                 120                 125

Ser Thr Ser Glu Glu Asn Ser Lys Lys Thr Val Asp Met Glu Ser Thr
    130                 135                 140

Glu Val Ile Thr Lys Lys Thr Lys Leu Thr Glu Glu Asp Lys Asn Arg
145                 150                 155                 160

Leu Asn Phe Leu Lys Lys Ile Ser Gln His Tyr Gln Lys Phe Thr Trp
                165                 170                 175

Pro Gln Tyr Leu Lys Thr Val Tyr Gln Tyr Gln Lys Ala Met Lys Pro
            180                 185                 190

Trp Thr Gln Pro Lys Thr Asn Val Ile Pro Tyr Val Arg Tyr Leu
        195                 200                 205


<210> SEQ ID NO 113
<211> LENGTH: 178
<212> TYPE: PRT
<213> ORGANISM: Camelus dromedaries

<400> SEQUENCE: 113

Lys His Glu Met Asp Gln Gly Ser Ser Ser Glu Glu Ser Ile Asn Val
1               5                   10                  15

Ser Gln Gln Lys Phe Lys Gln Val Lys Lys Val Ala Ile His Pro Ser
            20                  25                  30

Lys Glu Asp Ile Cys Ser Thr Phe Cys Glu Glu Ala Val Arg Asn Ile
        35                  40                  45

Lys Glu Val Glu Ser Ala Glu Val Pro Thr Glu Asn Lys Ile Ser Gln
    50                  55                  60

Phe Tyr Gln Lys Trp Lys Phe Leu Gln Tyr Leu Gln Ala Leu His Gln
65                  70                  75                  80

Gly Gln Ile Val Met Asn Pro Trp Asp Gln Gly Lys Thr Arg Ala Tyr
                85                  90                  95

Pro Phe Ile Pro Thr Val Asn Thr Glu Gln Leu Ser Ile Ser Glu Glu
            100                 105                 110

Ser Thr Glu Val Pro Thr Glu Glu Ser Thr Glu Val Phe Thr Lys Lys
        115                 120                 125

Thr Glu Leu Thr Glu Glu Glu Lys Asp His Gln Lys Phe Leu Asn Lys
    130                 135                 140

Ile Tyr Gln Tyr Tyr Gln Thr Phe Leu Trp Pro Glu Tyr Leu Lys Thr
145                 150                 155                 160

Val Tyr Gln Tyr Gln Lys Thr Met Thr Pro Trp Asn His Ile Lys Arg
                165                 170                 175

Tyr Phe


<210> SEQ ID NO 114
<211> LENGTH: 178
<212> TYPE: PRT
<213> ORGANISM: Camelus bactrianus
```

```
<400> SEQUENCE: 114

Lys His Glu Met Asp Gln Gly Ser Ser Ser Glu Glu Ser Ile Asn Val
1               5                   10                  15

Ser Gln Gln Lys Phe Lys Gln Val Lys Lys Val Ala Ile His Pro Ser
            20                  25                  30

Lys Glu Asp Ile Cys Ser Thr Phe Cys Glu Glu Ala Val Arg Asn Ile
        35                  40                  45

Lys Glu Val Glu Ser Ala Glu Val Pro Thr Glu Asn Lys Ile Ser Gln
    50                  55                  60

Phe Tyr Gln Lys Trp Lys Phe Leu Gln Tyr Leu Gln Ala Leu His Gln
65                  70                  75                  80

Gly Gln Ile Val Met Asn Pro Trp Asp Gln Gly Lys Thr Arg Ala Tyr
                85                  90                  95

Pro Phe Ile Pro Thr Val Asn Thr Glu Gln Leu Ser Ile Ser Glu Glu
            100                 105                 110

Ser Thr Glu Val Pro Thr Glu Glu Ser Thr Glu Val Phe Asn Lys Lys
        115                 120                 125

Thr Glu Leu Thr Glu Glu Glu Lys Asp His Gln Lys Phe Leu Asn Lys
    130                 135                 140

Ile Tyr Gln Tyr Tyr Gln Thr Phe Leu Trp Pro Glu Tyr Leu Lys Thr
145                 150                 155                 160

Val Tyr Gln Tyr Gln Lys Thr Met Thr Pro Trp Asn His Ile Lys Arg
                165                 170                 175

Tyr Phe


<210> SEQ ID NO 115
<211> LENGTH: 204
<212> TYPE: PRT
<213> ORGANISM: Bos mutus

<400> SEQUENCE: 115

Lys Asn Thr Met Glu His Val Ser Ser Ser Glu Glu Ser Ile Ile Ser
1               5                   10                  15

Gln Glu Thr Tyr Lys Gln Glu Lys Asn Met Ala Ile Asn Pro Ser Lys
            20                  25                  30

Gly Asn Leu Cys Ser Thr Phe Cys Lys Glu Val Val Arg Asn Ala Asn
        35                  40                  45

Glu Glu Glu Tyr Ser Ile Gly Ser Ser Ser Glu Glu Ser Ala Glu Val
    50                  55                  60

Ala Thr Glu Glu Val Lys Ile Thr Val Asp Asp Lys His Tyr Gln Lys
65                  70                  75                  80

Ala Leu Asn Glu Ile Asn Gln Phe Tyr Gln Lys Phe Pro Gln Tyr Leu
                85                  90                  95

Gln Tyr Leu Tyr Gln Gly Pro Ile Val Leu Asn Pro Trp Asp Gln Val
            100                 105                 110

Lys Arg Asn Ala Val Pro Ile Thr Pro Thr Leu Asn Arg Glu Gln Leu
        115                 120                 125

Ser Thr Ser Glu Glu Asn Ser Lys Lys Thr Val Asp Met Glu Ser Thr
    130                 135                 140

Glu Val Phe Thr Lys Lys Thr Lys Leu Thr Glu Glu Glu Lys Asn Arg
145                 150                 155                 160

Leu Asn Phe Leu Lys Lys Ile Ser Gln Arg Tyr Gln Lys Phe Ala Leu
                165                 170                 175
```

```
Pro Gln Tyr Leu Lys Thr Val Tyr Gln His Gln Lys Ala Met Lys Pro
            180                 185                 190

Trp Ile Gln Pro Lys Thr Lys Val Ile Pro Tyr Val
        195                 200


<210> SEQ ID NO 116
<211> LENGTH: 216
<212> TYPE: PRT
<213> ORGANISM: Equus caballus

<400> SEQUENCE: 116

Lys His Asn Met Glu His Arg Ser Ser Ser Glu Asp Ser Val Asn Ile
1               5                   10                  15

Ser Gln Glu Lys Phe Lys Gln Glu Lys Tyr Val Val Ile Pro Thr Ser
            20                  25                  30

Lys Glu Ser Ile Cys Ser Thr Ser Cys Glu Glu Ala Thr Arg Asn Ile
        35                  40                  45

Asn Glu Met Glu Ser Ala Lys Phe Pro Thr Glu Val Tyr Ser Ser Ser
    50                  55                  60

Ser Ser Ser Glu Glu Ser Ala Lys Phe Pro Thr Glu Arg Glu Glu Lys
65                  70                  75                  80

Glu Val Glu Glu Lys His His Leu Lys Gln Leu Asn Lys Ile Asn Gln
                85                  90                  95

Phe Tyr Glu Lys Leu Asn Phe Leu Gln Tyr Leu Gln Ala Leu Arg Gln
            100                 105                 110

Pro Arg Ile Val Leu Thr Pro Trp Asp Gln Thr Lys Thr Gly Asp Ser
        115                 120                 125

Pro Phe Ile Pro Ile Val Asn Thr Glu Gln Leu Phe Thr Ser Glu Glu
    130                 135                 140

Ile Pro Lys Lys Thr Val Asp Met Glu Ser Thr Glu Val Val Thr Glu
145                 150                 155                 160

Lys Thr Glu Leu Thr Glu Glu Glu Lys Asn Tyr Leu Lys Leu Leu Tyr
                165                 170                 175

Tyr Glu Lys Phe Thr Leu Pro Gln Tyr Phe Lys Ile Val Arg Gln His
            180                 185                 190

Gln Thr Thr Met Asp Pro Arg Ser His Arg Lys Thr Asn Ser Tyr Gln
        195                 200                 205

Ile Ile Pro Val Leu Arg Tyr Phe
    210                 215


<210> SEQ ID NO 117
<211> LENGTH: 221
<212> TYPE: PRT
<213> ORGANISM: Equus asinus

<400> SEQUENCE: 117

Lys His Asn Met Glu His Arg Ser Ser Ser Glu Asp Ser Val Asn Ile
1               5                   10                  15

Ser Gln Glu Lys Phe Lys Gln Glu Lys Tyr Val Val Ile Pro Thr Ser
            20                  25                  30

Lys Glu Ser Ile Cys Ser Thr Ser Cys Glu Glu Ala Thr Arg Asn Ile
        35                  40                  45

Asn Glu Met Glu Ser Ala Lys Phe Pro Thr Glu Val Tyr Ser Ser Ser
    50                  55                  60

Ser Ser Ser Glu Glu Ser Ala Lys Phe Pro Thr Glu Arg Glu Glu Lys
65                  70                  75                  80
```

```
Glu Val Glu Glu Lys His His Leu Lys Gln Leu Asn Lys Ile Asn Gln
                85                  90                  95

Phe Tyr Glu Lys Leu Asn Phe Leu Gln Tyr Leu Gln Ala Leu Arg Gln
            100                 105                 110

Pro Arg Ile Val Leu Thr Pro Trp Asp Gln Thr Lys Thr Gly Ala Ser
        115                 120                 125

Pro Phe Ile Pro Ile Val Asn Thr Glu Gln Leu Phe Thr Ser Glu Glu
    130                 135                 140

Ile Pro Lys Lys Thr Val Asp Met Glu Ser Thr Glu Val Val Thr Glu
145                 150                 155                 160

Lys Thr Glu Leu Thr Glu Glu Glu Lys Asn Tyr Leu Lys Leu Leu Asn
                165                 170                 175

Lys Ile Asn Gln Tyr Tyr Glu Lys Phe Thr Leu Pro Gln Tyr Phe Lys
            180                 185                 190

Ile Val His Gln His Gln Thr Thr Met Asp Pro Gln Ser His Ser Lys
        195                 200                 205

Thr Asn Ser Tyr Gln Ile Ile Pro Val Leu Arg Tyr Phe
    210                 215                 220
```

<210> SEQ ID NO 118
<211> LENGTH: 192
<212> TYPE: PRT
<213> ORGANISM: Vicugna pacos

<400> SEQUENCE: 118

```
Lys His Glu Met Asp Gln Gly Ser Ser Ser Glu Glu Ser Ile Asn Val
1               5                   10                  15

Ser Gln Gln Lys Leu Lys Gln Val Lys Lys Val Ala Ile His Pro Ser
            20                  25                  30

Lys Glu Asp Ile Cys Ser Thr Phe Cys Glu Glu Ala Val Arg Asn Ile
        35                  40                  45

Lys Glu Val Glu Ser Val Glu Val Pro Thr Glu Asn Lys Ile Ser Gln
    50                  55                  60

Phe Tyr Gln Lys Trp Lys Phe Leu Gln Tyr Leu Gln Ala Leu His Gln
65                  70                  75                  80

Gly Gln Ile Val Met Asn Pro Trp Asp Gln Gly Lys Thr Met Val Tyr
                85                  90                  95

Pro Phe Ile Pro Thr Val Asn Thr Glu Gln Leu Ser Ile Ser Glu Glu
            100                 105                 110

Ser Thr Glu Val Pro Thr Glu Glu Ser Thr Glu Val Phe Thr Lys Lys
        115                 120                 125

Thr Glu Leu Thr Glu Glu Glu Lys Asp His Gln Lys Phe Leu Asn Lys
    130                 135                 140

Ile Tyr Gln Tyr Tyr Gln Thr Phe Leu Trp Pro Glu Tyr Leu Lys Thr
145                 150                 155                 160

Val Tyr Gln Tyr Gln Lys Thr Met Thr Pro Trp Asn His Ile Lys Val
                165                 170                 175

Lys Ala Tyr Gln Ile Ile Pro Asn Leu Val Ser Ser Thr Phe Tyr Leu
            180                 185                 190
```

<210> SEQ ID NO 119
<211> LENGTH: 207
<212> TYPE: PRT
<213> ORGANISM: Bos indicus

<400> SEQUENCE: 119

```
Lys Asn Thr Met Glu His Val Ser Ser Ser Glu Glu Ser Ile Ile Ser
1               5                   10                  15

Gln Glu Thr Tyr Lys Gln Glu Lys Asn Met Ala Ile Asn Pro Ser Lys
            20                  25                  30

Glu Asn Leu Cys Ser Thr Phe Cys Lys Glu Val Val Arg Asn Ala Asn
        35                  40                  45

Glu Glu Glu Tyr Ser Ile Gly Ser Ser Ser Glu Glu Ser Ala Glu Val
    50                  55                  60

Ala Thr Glu Glu Val Lys Ile Thr Val Asp Asp Lys His Tyr Gln Lys
65                  70                  75                  80

Ala Leu Asn Glu Ile Asn Gln Phe Tyr Gln Lys Phe Pro Gln Tyr Leu
                85                  90                  95

Gln Tyr Leu Tyr Gln Gly Pro Ile Val Leu Asn Pro Trp Asp Gln Val
            100                 105                 110

Lys Arg Asn Ala Val Pro Ile Thr Pro Thr Leu Asn Arg Glu Gln Leu
        115                 120                 125

Ser Thr Ser Glu Glu Asn Ser Lys Lys Thr Val Asp Met Glu Ser Thr
    130                 135                 140

Glu Val Phe Thr Lys Lys Thr Lys Leu Thr Glu Glu Glu Lys Asn Arg
145                 150                 155                 160

Leu Asn Phe Leu Lys Lys Ile Ser Gln Arg Tyr Gln Lys Phe Ala Leu
                165                 170                 175

Pro Gln Tyr Leu Lys Thr Val Tyr Gln His Gln Lys Ala Met Lys Pro
            180                 185                 190

Trp Ile Gln Pro Lys Thr Lys Val Ile Pro Tyr Val Arg Tyr Leu
        195                 200                 205
```

<210> SEQ ID NO 120
<211> LENGTH: 187
<212> TYPE: PRT
<213> ORGANISM: Lama glama

<400> SEQUENCE: 120

```
Lys His Glu Met Asp Gln Gly Ser Ser Ser Glu Glu Ser Ile Asn Val
1               5                   10                  15

Ser Gln Gln Lys Leu Lys Gln Val Lys Lys Val Ala Ile His Pro Ser
            20                  25                  30

Lys Glu Asp Ile Cys Ser Thr Phe Cys Glu Glu Ala Val Arg Asn Ile
        35                  40                  45

Lys Glu Val Glu Ser Val Glu Val Pro Thr Glu Asn Lys Ile Ser Gln
    50                  55                  60

Phe Tyr Gln Lys Trp Lys Phe Leu Gln Tyr Leu Gln Ala Leu His Gln
65                  70                  75                  80

Gly Gln Ile Val Met Asn Pro Trp Asp Gln Gly Lys Thr Met Val Tyr
                85                  90                  95

Pro Phe Ile Pro Thr Val Asn Thr Glu Gln Leu Ser Ile Ser Glu Glu
            100                 105                 110

Ser Thr Glu Val Pro Thr Glu Glu Asn Ser Lys Lys Thr Val Asp Thr
        115                 120                 125

Glu Ser Thr Glu Val Phe Thr Lys Lys Thr Glu Leu Thr Glu Glu Glu
    130                 135                 140

Lys Asp His Gln Lys Phe Leu Asn Lys Ile Tyr Gln Tyr Tyr Gln Thr
145                 150                 155                 160
```

```
Phe Leu Trp Pro Glu Tyr Leu Lys Thr Val Tyr Gln Tyr Gln Lys Thr
                165                 170                 175

Met Thr Pro Trp Asn His Ile Lys Arg Tyr Phe
            180                 185


<210> SEQ ID NO 121
<211> LENGTH: 207
<212> TYPE: PRT
<213> ORGANISM: Capra hircus

<400> SEQUENCE: 121

Arg Glu Gln Glu Glu Leu Asn Val Val Gly Glu Thr Val Glu Ser Leu
1               5                   10                  15

Ser Ser Ser Glu Glu Ser Ile Thr His Ile Asn Lys Lys Ile Glu Lys
            20                  25                  30

Phe Gln Ser Glu Glu Gln Gln Gln Thr Glu Asp Glu Leu Gln Asp Lys
        35                  40                  45

Ile His Pro Phe Ala Gln Ala Gln Ser Leu Val Tyr Pro Phe Thr Gly
    50                  55                  60

Pro Ile Pro Asn Ser Leu Pro Gln Asn Ile Leu Pro Leu Thr Gln Thr
65                  70                  75                  80

Pro Val Val Val Pro Pro Phe Leu Gln Pro Glu Ile Met Gly Val Pro
                85                  90                  95

Lys Val Lys Glu Thr Met Val Pro Lys His Lys Glu Met Pro Phe Pro
            100                 105                 110

Lys Tyr Pro Val Glu Pro Phe Thr Glu Ser Gln Ser Leu Thr Leu Thr
        115                 120                 125

Asp Val Glu Lys Leu His Leu Pro Leu Pro Leu Val Gln Ser Trp Met
    130                 135                 140

His Gln Pro Pro Gln Pro Leu Ser Pro Thr Val Met Phe Pro Pro Gln
145                 150                 155                 160

Ser Val Leu Ser Leu Ser Gln Pro Lys Val Leu Pro Val Pro Gln Lys
                165                 170                 175

Ala Val Pro Gln Arg Asp Met Pro Ile Gln Ala Phe Leu Leu Tyr Gln
            180                 185                 190

Glu Pro Val Leu Gly Pro Val Arg Gly Pro Phe Pro Ile Leu Val
        195                 200                 205


<210> SEQ ID NO 122
<211> LENGTH: 207
<212> TYPE: PRT
<213> ORGANISM: Ovis aries

<400> SEQUENCE: 122

Arg Glu Gln Glu Glu Leu Asn Val Val Gly Glu Thr Val Glu Ser Leu
1               5                   10                  15

Ser Ser Ser Glu Glu Ser Ile Thr His Ile Asn Lys Lys Ile Glu Lys
            20                  25                  30

Phe Gln Ser Glu Glu Gln Gln Gln Thr Glu Asp Glu Leu Gln Asp Lys
        35                  40                  45

Ile His Pro Phe Ala Gln Ala Gln Ser Leu Val Tyr Pro Phe Thr Gly
    50                  55                  60

Pro Ile Pro Asn Ser Leu Pro Gln Asn Ile Leu Pro Leu Thr Gln Thr
65                  70                  75                  80

Pro Val Val Val Pro Pro Phe Leu Gln Pro Glu Ile Met Gly Val Pro
                85                  90                  95
```

```
Lys Val Lys Glu Thr Met Val Pro Lys His Lys Glu Met Pro Phe Pro
            100                 105                 110

Lys Tyr Pro Val Glu Pro Phe Thr Glu Ser Gln Ser Leu Thr Leu Thr
        115                 120                 125

Asp Val Glu Lys Leu His Leu Pro Leu Pro Leu Val Gln Ser Trp Met
    130                 135                 140

His Gln Pro Pro Gln Pro Leu Pro Pro Thr Val Met Phe Pro Pro Gln
145                 150                 155                 160

Ser Val Leu Ser Leu Ser Gln Pro Lys Val Leu Pro Val Pro Gln Lys
                165                 170                 175

Ala Val Pro Gln Arg Asp Met Pro Ile Gln Ala Phe Leu Leu Tyr Gln
            180                 185                 190

Glu Pro Val Leu Gly Pro Val Arg Gly Pro Phe Pro Ile Leu Val
        195                 200                 205


<210> SEQ ID NO 123
<211> LENGTH: 209
<212> TYPE: PRT
<213> ORGANISM: Bubalus bubalis

<400> SEQUENCE: 123

Arg Glu Leu Glu Glu Leu Asn Val Pro Gly Glu Ile Val Glu Ser Leu
1               5                   10                  15

Ser Ser Ser Glu Glu Ser Ile Thr His Ile Asn Lys Lys Ile Glu Lys
            20                  25                  30

Phe Gln Ser Glu Glu Gln Gln Gln Met Glu Asp Glu Leu Gln Asp Lys
        35                  40                  45

Ile His Pro Phe Ala Gln Thr Gln Ser Leu Val Tyr Pro Phe Pro Gly
    50                  55                  60

Pro Ile Pro Lys Ser Leu Pro Gln Asn Ile Pro Pro Leu Thr Gln Thr
65                  70                  75                  80

Pro Val Val Val Pro Pro Phe Leu Gln Pro Glu Ile Met Gly Val Ser
                85                  90                  95

Lys Val Lys Glu Ala Met Ala Pro Lys His Lys Glu Met Pro Phe Pro
            100                 105                 110

Lys Tyr Pro Val Glu Pro Phe Thr Glu Ser Gln Ser Leu Thr Leu Thr
        115                 120                 125

Asp Val Glu Asn Leu His Leu Pro Leu Pro Leu Leu Gln Ser Trp Met
    130                 135                 140

His Gln Pro Pro Gln Pro Leu Pro Pro Thr Val Met Phe Pro Pro Gln
145                 150                 155                 160

Ser Val Leu Ser Leu Ser Gln Ser Lys Val Leu Pro Val Pro Gln Lys
                165                 170                 175

Ala Val Pro Tyr Pro Gln Arg Asp Met Pro Ile Gln Ala Phe Leu Leu
            180                 185                 190

Tyr Gln Glu Pro Val Leu Gly Pro Val Arg Gly Pro Phe Pro Ile Ile
        195                 200                 205

Val


<210> SEQ ID NO 124
<211> LENGTH: 217
<212> TYPE: PRT
<213> ORGANISM: Camelus dromedaries
```

```
<400> SEQUENCE: 124

Arg Glu Lys Glu Glu Phe Lys Thr Ala Gly Glu Ala Leu Glu Ser Ile
1               5                   10                  15

Ser Ser Ser Glu Glu Ser Ile Thr His Ile Asn Lys Gln Lys Ile Glu
            20                  25                  30

Lys Phe Lys Ile Glu Glu Gln Gln Gln Thr Glu Asp Glu Gln Gln Asp
        35                  40                  45

Lys Ile Tyr Thr Phe Pro Gln Pro Gln Ser Leu Val Tyr Ser His Thr
    50                  55                  60

Glu Pro Ile Pro Tyr Pro Ile Leu Pro Gln Asn Phe Leu Pro Pro Leu
65                  70                  75                  80

Gln Pro Ala Val Met Val Pro Phe Leu Gln Pro Lys Val Met Asp Val
                85                  90                  95

Pro Lys Thr Lys Glu Thr Ile Ile Pro Lys Arg Lys Glu Met Pro Leu
            100                 105                 110

Leu Gln Ser Pro Val Val Pro Phe Thr Glu Ser Gln Ser Leu Thr Leu
        115                 120                 125

Thr Asp Leu Glu Asn Leu His Leu Pro Leu Pro Leu Leu Gln Ser Leu
    130                 135                 140

Met Tyr Gln Ile Pro Gln Pro Val Pro Gln Thr Pro Met Ile Pro Pro
145                 150                 155                 160

Gln Ser Leu Leu Ser Leu Ser Gln Phe Lys Val Leu Pro Val Pro Gln
                165                 170                 175

Gln Met Val Pro Tyr Pro Gln Arg Ala Met Pro Val Gln Ala Val Leu
            180                 185                 190

Pro Phe Gln Glu Pro Val Pro Asp Pro Val Arg Gly Leu His Pro Val
        195                 200                 205

Pro Gln Pro Leu Val Pro Val Ile Ala
    210                 215


<210> SEQ ID NO 125
<211> LENGTH: 217
<212> TYPE: PRT
<213> ORGANISM: Camelus bactrianus

<400> SEQUENCE: 125

Arg Glu Lys Glu Glu Phe Lys Thr Ala Gly Glu Ala Leu Glu Ser Ile
1               5                   10                  15

Ser Ser Ser Glu Glu Ser Ile Thr His Ile Asn Lys Gln Lys Ile Glu
            20                  25                  30

Lys Phe Lys Ile Glu Glu Gln Gln Gln Thr Glu Asp Glu Gln Gln Asp
        35                  40                  45

Lys Ile Tyr Thr Phe Pro Gln Pro Gln Ser Leu Val Tyr Ser His Thr
    50                  55                  60

Glu Pro Ile Pro Tyr Pro Ile Leu Pro Gln Asn Phe Leu Pro Pro Leu
65                  70                  75                  80

Gln Pro Ala Val Met Val Pro Phe Leu Gln Pro Lys Val Met Asp Val
                85                  90                  95

Pro Lys Thr Lys Glu Thr Ile Ile Pro Lys Arg Lys Glu Met Pro Leu
            100                 105                 110

Leu Gln Ser Pro Val Val Pro Phe Thr Glu Ser Gln Ser Leu Thr Leu
        115                 120                 125

Thr Asp Leu Glu Asn Leu His Leu Pro Leu Pro Leu Leu Gln Ser Leu
    130                 135                 140
```

Met Tyr Gln Ile Pro Gln Pro Val Pro Gln Thr Pro Met Ile Pro Pro
145 150 155 160

Gln Ser Leu Leu Ser Leu Ser Gln Phe Lys Val Leu Pro Val Pro Gln
165 170 175

Gln Met Val Pro Tyr Pro Gln Arg Ala Ile Pro Val Gln Ala Val Leu
180 185 190

Pro Phe Gln Glu Pro Val Pro Asp Pro Val Arg Gly Leu His Pro Val
195 200 205

Pro Gln Pro Leu Val Pro Val Ile Ala
210 215

<210> SEQ ID NO 126
<211> LENGTH: 209
<212> TYPE: PRT
<213> ORGANISM: Bos mutus

<400> SEQUENCE: 126

Arg Glu Leu Glu Glu Leu Asn Val Pro Gly Glu Ile Val Glu Ser Leu
1 5 10 15

Ser Ser Ser Glu Glu Ser Ile Thr Arg Ile Asn Lys Lys Ile Glu Lys
20 25 30

Phe Gln Ser Glu Glu Gln Gln Gln Thr Glu Asp Glu Leu Gln Asp Lys
35 40 45

Ile His Pro Phe Ala Gln Thr Gln Ser Leu Val Tyr Pro Phe Pro Gly
50 55 60

Pro Ile Pro Asn Ser Leu Pro Gln Asn Ile Pro Pro Leu Thr Gln Thr
65 70 75 80

Pro Val Val Val Pro Pro Phe Leu Gln Pro Glu Val Met Gly Val Ser
85 90 95

Lys Val Lys Glu Ala Met Ala Pro Lys His Lys Glu Met Pro Phe Pro
100 105 110

Lys Tyr Pro Val Glu Pro Phe Thr Glu Ser Gln Ser Leu Thr Leu Thr
115 120 125

Asp Val Glu Asn Leu His Leu Pro Leu Pro Leu Leu Gln Ser Trp Met
130 135 140

His Gln Pro His Gln Pro Leu Pro Pro Thr Val Met Phe Pro Pro Gln
145 150 155 160

Ser Val Leu Ser Leu Ser Gln Ser Lys Val Leu Pro Val Pro Gln Lys
165 170 175

Ala Val Pro Tyr Pro Gln Arg Asp Met Pro Ile Gln Ala Phe Leu Leu
180 185 190

Tyr Gln Glu Pro Val Leu Gly Pro Val Arg Gly Pro Phe Pro Ile Ile
195 200 205

Val

<210> SEQ ID NO 127
<211> LENGTH: 226
<212> TYPE: PRT
<213> ORGANISM: Equus caballus

<400> SEQUENCE: 127

Arg Glu Lys Glu Glu Leu Asn Val Ser Ser Glu Thr Val Glu Ser Leu
1 5 10 15

Ser Ser Asn Glu Pro Asp Ser Ser Ser Glu Glu Ser Ile Thr His Ile
20 25 30

```
Asn Lys Glu Lys Leu Gln Lys Phe Lys His Glu Gly Gln Gln Gln Arg
        35                  40                  45

Glu Val Glu Arg Gln Asp Lys Ile Ser Arg Phe Val Gln Pro Gln Pro
    50                  55                  60

Val Val Tyr Pro Tyr Ala Glu Pro Val Pro Tyr Ala Val Val Pro Gln
65                  70                  75                  80

Ser Ile Leu Pro Leu Ala Gln Pro Pro Ile Leu Pro Phe Leu Gln Pro
                85                  90                  95

Glu Ile Met Glu Val Ser Gln Ala Lys Glu Thr Ile Leu Pro Lys Arg
            100                 105                 110

Lys Val Met Pro Phe Leu Lys Ser Pro Ile Val Pro Phe Ser Glu Arg
        115                 120                 125

Gln Ile Leu Asn Pro Thr Asn Gly Glu Asn Leu Arg Leu Pro Val His
    130                 135                 140

Leu Ile Gln Pro Phe Met His Gln Val Pro Gln Ser Leu Leu Gln Thr
145                 150                 155                 160

Leu Met Leu Pro Ser Gln Pro Val Leu Ser Pro Pro Gln Ser Lys Val
                165                 170                 175

Ala Pro Phe Pro Gln Pro Val Val Pro Tyr Pro Gln Arg Asp Thr Pro
            180                 185                 190

Val Gln Ala Phe Leu Leu Tyr Gln Asp Pro Arg Leu Gly Pro Thr Gly
        195                 200                 205

Glu Leu Asp Pro Ala Thr Gln Pro Ile Val Ala Val His Asn Pro Val
    210                 215                 220

Ile Val
225


<210> SEQ ID NO 128
<211> LENGTH: 226
<212> TYPE: PRT
<213> ORGANISM: Equus asinus

<400> SEQUENCE: 128

Arg Glu Lys Glu Glu Leu Asn Val Ser Ser Glu Thr Val Glu Ser Leu
1               5                   10                  15

Ser Ser Asn Glu Pro Asp Ser Ser Ser Glu Glu Ser Ile Thr His Ile
            20                  25                  30

Asn Lys Glu Lys Ser Gln Lys Phe Lys His Glu Gly Gln Gln Gln Arg
        35                  40                  45

Glu Val Glu His Gln Asp Lys Ile Ser Arg Phe Val Gln Pro Gln Pro
    50                  55                  60

Val Val Tyr Pro Tyr Ala Glu Pro Val Pro Tyr Ala Val Val Pro Gln
65                  70                  75                  80

Asn Ile Leu Val Leu Ala Gln Pro Pro Ile Val Pro Phe Leu Gln Pro
                85                  90                  95

Glu Ile Met Glu Val Ser Gln Ala Lys Glu Thr Ile Leu Pro Lys Arg
            100                 105                 110

Lys Val Met Pro Phe Leu Lys Ser Pro Ile Val Pro Phe Ser Glu Arg
        115                 120                 125

Gln Ile Leu Asn Pro Thr Asn Gly Glu Asn Leu Arg Leu Pro Val His
    130                 135                 140

Leu Ile Gln Pro Phe Met His Gln Val Pro Gln Ser Leu Leu Gln Thr
145                 150                 155                 160

Leu Met Leu Pro Ser Gln Pro Val Leu Ser Pro Pro Gln Ser Lys Val
                165                 170                 175
```

```
Ala Pro Phe Pro Gln Pro Val Val Pro Tyr Pro Gln Arg Asp Thr Pro
            180                 185                 190

Val Gln Ala Phe Leu Leu Tyr Gln Asp Pro Gln Leu Gly Leu Thr Gly
        195                 200                 205

Glu Phe Asp Pro Ala Thr Gln Pro Ile Val Pro Val His Asn Pro Val
    210                 215                 220

Ile Val
225


<210> SEQ ID NO 129
<211> LENGTH: 141
<212> TYPE: PRT
<213> ORGANISM: Alces alces
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: misc_feature
<222> LOCATION: (65)..(65)
<223> OTHER INFORMATION: Xaa can be any naturally occurring amino acid

<400> SEQUENCE: 129

Ile His Pro Phe Ala Xaa Thr Gln Ser Leu Val Tyr Pro Phe Thr Gly
1               5                   10                  15

Xaa Ile Pro Tyr Ser Leu Pro Gln Asn Phe Leu Pro Leu Pro Gln Thr
            20                  25                  30

Pro Gly Met Val Pro Pro Phe Leu Gln Pro Glu Ile Met Gly Val Ser
        35                  40                  45

Glu Val Lys Glu Thr Met Val Pro Lys Asn Lys Glu Met Pro Phe Pro
    50                  55                  60

Xaa Tyr Pro Val Glu Pro Phe Ala Glu Gly Gln Ser Leu Thr Leu Thr
65                  70                  75                  80

Asp Val Glu Asn Leu His Leu Pro Leu Pro Leu Leu Gln Ser Trp Met
                85                  90                  95

His Gln Thr Pro Gln Pro Leu Pro Pro Thr Val Met Phe Pro Pro Gln
            100                 105                 110

Ser Val Leu Ser Leu Ser Gln Pro Lys Val Leu Ser Val Pro Gln Lys
        115                 120                 125

Ala Val Pro Tyr Pro Gln Arg Asp Met Pro Ile Gln Ala
    130                 135                 140


<210> SEQ ID NO 130
<211> LENGTH: 173
<212> TYPE: PRT
<213> ORGANISM: Vicugna pacos

<400> SEQUENCE: 130

Asp Glu Gln Gln Asp Lys Ile Tyr Thr Phe Pro Gln Pro Gln Ser Leu
1               5                   10                  15

Val Tyr Ser His Thr Glu Pro Ile Pro Tyr Pro Ile Leu Pro Gln Asn
            20                  25                  30

Phe Leu Pro Pro Leu Gln Pro Ala Val Met Val Pro Phe Leu Gln Pro
        35                  40                  45

Lys Val Met Asp Val Pro Lys Thr Lys Glu Ile Val Ile Pro Lys Arg
    50                  55                  60
```

```
Lys Glu Met Pro Leu Leu Gln Ser Pro Leu Val Pro Phe Thr Glu Ser
65                  70                  75                  80

Gln Ser Leu Thr Leu Thr Asp Leu Glu Asn Leu His Leu Pro Leu Pro
                85                  90                  95

Leu Leu Gln Ser Leu Met His Gln Ile Pro Gln Pro Val Pro Gln Thr
            100                 105                 110

Pro Met Ile Pro Pro Gln Ser Leu Leu Ser Leu Ser Gln Phe Lys Val
        115                 120                 125

Leu Pro Val Pro Gln Gln Met Val Pro Tyr Pro Gln Arg Ala Met Pro
    130                 135                 140

Val Gln Ala Leu Leu Pro Phe Gln Glu Pro Ile Pro Asp Pro Val Arg
145                 150                 155                 160

Gly Leu His Pro Val Pro Gln Pro Leu Val Pro Val Ile
                165                 170


<210> SEQ ID NO 131
<211> LENGTH: 209
<212> TYPE: PRT
<213> ORGANISM: Bos indicus

<400> SEQUENCE: 131

Arg Glu Leu Glu Glu Leu Asn Val Pro Gly Glu Ile Val Glu Ser Leu
1               5                   10                  15

Ser Ser Ser Glu Glu Ser Ile Thr Arg Ile Asn Lys Lys Ile Glu Lys
            20                  25                  30

Phe Gln Ser Glu Glu Gln Gln Gln Thr Glu Asp Glu Leu Gln Asp Lys
        35                  40                  45

Ile His Pro Phe Ala Gln Thr Gln Ser Leu Val Tyr Pro Phe Pro Gly
    50                  55                  60

Pro Ile Pro Asn Ser Leu Pro Gln Asn Ile Pro Pro Leu Thr Gln Thr
65                  70                  75                  80

Pro Val Val Val Pro Pro Phe Leu Gln Pro Glu Val Met Gly Val Ser
                85                  90                  95

Lys Val Lys Glu Ala Met Ala Pro Lys His Lys Glu Met Pro Phe Pro
            100                 105                 110

Lys Tyr Pro Val Glu Pro Phe Thr Glu Ser Gln Ser Leu Thr Leu Thr
        115                 120                 125

Asp Val Glu Asn Leu His Leu Pro Leu Pro Leu Leu Gln Ser Trp Met
    130                 135                 140

His Gln Pro His Gln Pro Leu Pro Pro Thr Val Met Phe Pro Pro Gln
145                 150                 155                 160

Ser Val Leu Ser Leu Ser Gln Ser Lys Val Leu Pro Val Pro Gln Lys
                165                 170                 175

Ala Val Pro Tyr Pro Gln Arg Asp Met Pro Ile Gln Ala Phe Leu Leu
            180                 185                 190

Tyr Gln Glu Pro Val Leu Gly Pro Val Arg Gly Pro Phe Pro Ile Ile
        195                 200                 205

Val


<210> SEQ ID NO 132
<211> LENGTH: 217
<212> TYPE: PRT
<213> ORGANISM: Lama glama
```

<400> SEQUENCE: 132

Arg Glu Lys Glu Glu Phe Lys Thr Ala Gly Glu Ala Val Glu Ser Ile
1               5                   10                  15

Ser Ser Ser Glu Glu Ser Ile Thr His Ile Asn Lys Gln Lys Ile Glu
            20                  25                  30

Lys Phe Lys Ile Glu Glu Gln Gln Gln Thr Glu Asp Glu Gln Gln Asp
        35                  40                  45

Lys Ile Tyr Thr Phe Pro Gln Pro Gln Ser Leu Val Tyr Ser His Thr
    50                  55                  60

Glu Pro Ile Pro Tyr Pro Ile Leu Pro Gln Asn Phe Leu Pro Pro Leu
65                  70                  75                  80

Gln Pro Ala Val Met Val Pro Phe Leu Gln Pro Lys Val Met Asp Val
                85                  90                  95

Pro Lys Thr Lys Glu Ile Val Ile Pro Lys Arg Lys Glu Met Pro Leu
            100                 105                 110

Leu Gln Ser Pro Leu Val Pro Phe Thr Glu Ser Gln Ser Leu Thr Leu
        115                 120                 125

Thr Asp Leu Glu Asn Leu His Leu Pro Leu Pro Leu Leu Gln Ser Leu
    130                 135                 140

Met His Gln Ile Pro Gln Pro Val Pro Gln Thr Pro Met Ile Pro Pro
145                 150                 155                 160

Gln Ser Leu Leu Ser Leu Ser Gln Phe Lys Val Leu Pro Val Pro Gln
                165                 170                 175

Gln Met Val Pro Tyr Pro Gln Arg Ala Met Pro Val Gln Ala Leu Leu
            180                 185                 190

Pro Phe Gln Glu Pro Ile Pro Asp Pro Val Arg Gly Leu His Pro Val
        195                 200                 205

Pro Gln Pro Leu Val Pro Val Ile Ala
    210                 215

<210> SEQ ID NO 133
<211> LENGTH: 211
<212> TYPE: PRT
<213> ORGANISM: Homo sapiens

<400> SEQUENCE: 133

Arg Glu Thr Ile Glu Ser Leu Ser Ser Ser Glu Glu Ser Ile Thr Glu
1               5                   10                  15

Tyr Lys Gln Lys Val Glu Lys Val Lys His Glu Asp Gln Gln Gln Gly
            20                  25                  30

Glu Asp Glu His Gln Asp Lys Ile Tyr Pro Ser Phe Gln Pro Gln Pro
        35                  40                  45

Leu Ile Tyr Pro Phe Val Glu Pro Ile Pro Tyr Gly Phe Leu Pro Gln
    50                  55                  60

Asn Ile Leu Pro Leu Ala Gln Pro Ala Val Val Leu Pro Val Pro Gln
65                  70                  75                  80

Pro Glu Ile Met Glu Val Pro Lys Ala Lys Asp Thr Val Tyr Thr Lys
                85                  90                  95

Gly Arg Val Met Pro Val Leu Lys Ser Pro Thr Ile Pro Phe Phe Asp
            100                 105                 110

Pro Gln Ile Pro Lys Leu Thr Asp Leu Glu Asn Leu His Leu Pro Leu
        115                 120                 125

Pro Leu Leu Gln Pro Leu Met Gln Gln Val Pro Gln Pro Ile Pro Gln
    130                 135                 140

```
Thr Leu Ala Leu Pro Pro Gln Pro Leu Trp Ser Val Pro Gln Pro Lys
145                 150                 155                 160

Val Leu Pro Ile Pro Gln Gln Val Val Pro Tyr Pro Gln Arg Ala Val
                165                 170                 175

Pro Val Gln Ala Leu Leu Leu Asn Gln Glu Leu Leu Leu Asn Pro Thr
            180                 185                 190

His Gln Ile Tyr Pro Val Thr Gln Pro Leu Ala Pro Val His Asn Pro
        195                 200                 205

Ile Ser Val
    210
```

<210> SEQ ID NO 134
<211> LENGTH: 1059
<212> TYPE: DNA
<213> ORGANISM: Artificial Sequence
<220> FEATURE:
<223> OTHER INFORMATION: Nucleic acid encoding fusion protein sig2:OKC1-T:FM:OLG1

<400> SEQUENCE: 134

```
atggccaagc tagttttttc cctttgtttt ctgcttttca gtggctgctg cttcgctcaa      60

gagcagaatc aagagcagcc aatccgttgt gagaaggacg agaggttctt ctcagacaag     120

atcgccaaat atatacccat acaatatgta ctctcacgct accctagcta cgggcttaac     180

tactatcagc aaaaacctgt agcactgata aataaccagt ttctccccta tccctattat     240

gctaaacctg ccgccgtgag gagtccagca caaatacttc agtggcaagt gctcagtaac     300

accgtgccag caaaaagctg ccaggctcag cccaccacaa tggcccgtca tccccatcct     360

caccttagct tcatggcaat cccaccaaag aagaatcaag acaagaccga aatacctacc     420

atcaacacaa ttgcatctgg agagcctacc agtacaccaa caactgaggc agtagagtct     480

actgttgcta cccttgagga cagccccgag gttatagagt ccccacctga gataaatacc     540

gtgcaggtga caagtaccgc cgtattcatg ttgatcgtaa cacagactat gaagggtctt     600

gatatacaga aggtggccgg gacttggtac agtttggcaa tggccgcatc cgacatctcc     660

ttgttggacg cacaatcagc cccattgcgt gtgtacgtag aagagcttaa accaactccc     720

gagggggatc tggaaattct gctccagaaa tgggagaacg gtgagtgcgc ccagaagaag     780

atcatcgcag agaagaccaa aattccagca gtattcaaaa tcgacgcatt gaacgaaaat     840

aaggtgctcg tactggacac tgattataag aagtatctcc ttttctgtat ggagaactca     900

gcagagcctg aacagagtct tgcctgccaa tgccttgttc gtaccccaga ggtagatgat     960

gaagctctgg aaaagttcga taaggccctt aaggctctgc ctatgcacat taggctttct    1020

ttcaatccaa ctcaacttga ggaacaatgt cacatttaa                           1059
```

<210> SEQ ID NO 135
<211> LENGTH: 352
<212> TYPE: PRT
<213> ORGANISM: Artificial Sequence
<220> FEATURE:
<223> OTHER INFORMATION: Fusion protein sig2:OKC1-T:FM:OLG1

<400> SEQUENCE: 135

```
Met Ala Lys Leu Val Phe Ser Leu Cys Phe Leu Leu Phe Ser Gly Cys
1               5                   10                  15

Cys Phe Ala Gln Glu Gln Asn Gln Glu Gln Pro Ile Arg Cys Glu Lys
            20                  25                  30
```

```
Asp Glu Arg Phe Phe Ser Asp Lys Ile Ala Lys Tyr Ile Pro Ile Gln
        35                  40                  45

Tyr Val Leu Ser Arg Tyr Pro Ser Tyr Gly Leu Asn Tyr Tyr Gln Gln
    50                  55                  60

Lys Pro Val Ala Leu Ile Asn Asn Gln Phe Leu Pro Tyr Pro Tyr Tyr
65                  70                  75                  80

Ala Lys Pro Ala Ala Val Arg Ser Pro Ala Gln Ile Leu Gln Trp Gln
                85                  90                  95

Val Leu Ser Asn Thr Val Pro Ala Lys Ser Cys Gln Ala Gln Pro Thr
            100                 105                 110

Thr Met Ala Arg His Pro His Pro His Leu Ser Phe Met Ala Ile Pro
        115                 120                 125

Pro Lys Lys Asn Gln Asp Lys Thr Glu Ile Pro Thr Ile Asn Thr Ile
    130                 135                 140

Ala Ser Gly Glu Pro Thr Ser Thr Pro Thr Thr Glu Ala Val Glu Ser
145                 150                 155                 160

Thr Val Ala Thr Leu Glu Asp Ser Pro Glu Val Ile Glu Ser Pro Pro
                165                 170                 175

Glu Ile Asn Thr Val Gln Val Thr Ser Thr Ala Val Phe Met Leu Ile
            180                 185                 190

Val Thr Gln Thr Met Lys Gly Leu Asp Ile Gln Lys Val Ala Gly Thr
        195                 200                 205

Trp Tyr Ser Leu Ala Met Ala Ala Ser Asp Ile Ser Leu Leu Asp Ala
    210                 215                 220

Gln Ser Ala Pro Leu Arg Val Tyr Val Glu Glu Leu Lys Pro Thr Pro
225                 230                 235                 240

Glu Gly Asp Leu Glu Ile Leu Leu Gln Lys Trp Glu Asn Gly Glu Cys
                245                 250                 255

Ala Gln Lys Lys Ile Ile Ala Glu Lys Thr Lys Ile Pro Ala Val Phe
            260                 265                 270

Lys Ile Asp Ala Leu Asn Glu Asn Lys Val Leu Val Leu Asp Thr Asp
        275                 280                 285

Tyr Lys Lys Tyr Leu Leu Phe Cys Met Glu Asn Ser Ala Glu Pro Glu
    290                 295                 300

Gln Ser Leu Ala Cys Gln Cys Leu Val Arg Thr Pro Glu Val Asp Asp
305                 310                 315                 320

Glu Ala Leu Glu Lys Phe Asp Lys Ala Leu Lys Ala Leu Pro Met His
                325                 330                 335

Ile Arg Leu Ser Phe Asn Pro Thr Gln Leu Glu Glu Gln Cys His Ile
            340                 345                 350
```

<210> SEQ ID NO 136
<211> LENGTH: 1071
<212> TYPE: DNA
<213> ORGANISM: Artificial Sequence
<220> FEATURE:
<223> OTHER INFORMATION: Nucleic acid encoding fusion protein sig2:OKC1-T:FM:OLG1:KDEL

<400> SEQUENCE: 136

```
atggccaagc tagttttttc cctttgtttt ctgcttttca gtggctgctg cttcgctcaa     60

gagcagaatc aagagcagcc aatccgttgt gagaaggacg agaggttctt ctcagacaag    120

atcgccaaat atatacccat acaatatgta ctctcacgct accctagcta cgggcttaac    180

tactatcagc aaaaacctgt agcactgata aataaccagt ttctccccta tccctattat    240
```

```
gctaaacctg ccgccgtgag gagtccagca caaatacttc agtggcaagt gctcagtaac    300

accgtgccag caaaaagctg ccaggctcag cccaccacaa tggcccgtca tccccatcct    360

caccttagct tcatggcaat cccaccaaag aagaatcaag acaagaccga aatacctacc    420

atcaacacaa ttgcatctgg agagcctacc agtacaccaa caactgaggc agtagagtct    480

actgttgcta cccttgagga cagccccgag gttatagagt ccccacctga gataaatacc    540

gtgcaggtga caagtaccgc cgtattcatg ttgatcgtaa cacagactat gaagggtctt    600

gatatacaga aggtggccgg gacttggtac agtttggcaa tggccgcatc cgacatctcc    660

ttgttggacg cacaatcagc ccattgcgt gtgtacgtag aagagcttaa accaactccc    720

gagggggatc tggaaattct gctccagaaa tgggagaacg gtgagtgcgc ccagaagaag    780

atcatcgcag agaagaccaa aattccagca gtattcaaaa tcgacgcatt gaacgaaaat    840

aaggtgctcg tactggacac tgattataag aagtatctcc ttttctgtat ggagaactca    900

gcagagcctg aacagagtct tgcctgccaa tgccttgttc gtaccccaga ggtagatgat    960

gaagctctgg aaaagttcga taaggccctt aaggctctgc ctatgcacat taggctttct   1020

ttcaatccaa ctcaacttga ggaacaatgt cacattaagg atgagcttta a            1071
```

<210> SEQ ID NO 137
<211> LENGTH: 356
<212> TYPE: PRT
<213> ORGANISM: Artificial Sequence
<220> FEATURE:
<223> OTHER INFORMATION: Fusion protein sig2:OKC1-T:FM:OLG1:KDEL

<400> SEQUENCE: 137

```
Met Ala Lys Leu Val Phe Ser Leu Cys Phe Leu Leu Phe Ser Gly Cys
1               5                   10                  15

Cys Phe Ala Gln Glu Gln Asn Gln Glu Gln Pro Ile Arg Cys Glu Lys
            20                  25                  30

Asp Glu Arg Phe Phe Ser Asp Lys Ile Ala Lys Tyr Ile Pro Ile Gln
        35                  40                  45

Tyr Val Leu Ser Arg Tyr Pro Ser Tyr Gly Leu Asn Tyr Tyr Gln Gln
    50                  55                  60

Lys Pro Val Ala Leu Ile Asn Asn Gln Phe Leu Pro Tyr Pro Tyr Tyr
65                  70                  75                  80

Ala Lys Pro Ala Ala Val Arg Ser Pro Ala Gln Ile Leu Gln Trp Gln
                85                  90                  95

Val Leu Ser Asn Thr Val Pro Ala Lys Ser Cys Gln Ala Gln Pro Thr
            100                 105                 110

Thr Met Ala Arg His Pro His Pro His Leu Ser Phe Met Ala Ile Pro
        115                 120                 125

Pro Lys Lys Asn Gln Asp Lys Thr Glu Ile Pro Thr Ile Asn Thr Ile
    130                 135                 140

Ala Ser Gly Glu Pro Thr Ser Thr Pro Thr Thr Glu Ala Val Glu Ser
145                 150                 155                 160

Thr Val Ala Thr Leu Glu Asp Ser Pro Glu Val Ile Glu Ser Pro Pro
                165                 170                 175

Glu Ile Asn Thr Val Gln Val Thr Ser Thr Ala Val Phe Met Leu Ile
            180                 185                 190

Val Thr Gln Thr Met Lys Gly Leu Asp Ile Gln Lys Val Ala Gly Thr
        195                 200                 205

Trp Tyr Ser Leu Ala Met Ala Ala Ser Asp Ile Ser Leu Leu Asp Ala
    210                 215                 220
```

-continued

```
Gln Ser Ala Pro Leu Arg Val Tyr Val Glu Glu Leu Lys Pro Thr Pro
225                 230                 235                 240

Glu Gly Asp Leu Glu Ile Leu Leu Gln Lys Trp Glu Asn Gly Glu Cys
                245                 250                 255

Ala Gln Lys Lys Ile Ile Ala Glu Lys Thr Lys Ile Pro Ala Val Phe
            260                 265                 270

Lys Ile Asp Ala Leu Asn Glu Asn Lys Val Leu Val Leu Asp Thr Asp
        275                 280                 285

Tyr Lys Lys Tyr Leu Leu Phe Cys Met Glu Asn Ser Ala Glu Pro Glu
    290                 295                 300

Gln Ser Leu Ala Cys Gln Cys Leu Val Arg Thr Pro Glu Val Asp Asp
305                 310                 315                 320

Glu Ala Leu Glu Lys Phe Asp Lys Ala Leu Lys Ala Leu Pro Met His
                325                 330                 335

Ile Arg Leu Ser Phe Asn Pro Thr Gln Leu Glu Glu Gln Cys His Ile
            340                 345                 350

Lys Asp Glu Leu
        355
```

RECOMBINANT FUSION PROTEINS FOR PRODUCING MILK PROTEINS IN PLANTS

CROSS REFERENCE TO RELATED APPLICATIONS

This application is a continuation of U.S. application Ser. No. 17/374,125, filed Jul. 13, 2021 now issued as U.S. Pat. No. 11,401,526 on Aug. 2, 2022, which is a division of U.S. application Ser. No. 17/157,105, filed Jan. 25, 2021 now issued as U.S. Pat. No. 11,072,797 on Jul. 27, 2021, which is a continuation of U.S. application Ser. No. 17/039,759, filed Sep. 30, 2020 now issued as U.S. Pat. No. 10,947,552 on Mar. 16, 2021, the disclosures of each of which are hereby incorporated by reference in their entireties.

DESCRIPTION OF THE TEXT FILE SUBMITTED ELECTRONICALLY

The contents of the text file submitted electronically herewith are incorporated herein by reference in their entirety: A computer readable format copy of the Sequence Listing filename: ALRO_007_16US_SeqList_ST25.txt, date recorded: Jun. 23, 2022, file size: 159,528 bytes.

FIELD OF THE DISCLOSURE

The present disclosure generally relates to recombinant milk proteins, and methods of production, extraction, and purification of the milk proteins from transgenic plants. The disclosure also relates to food compositions comprising recombinant milk proteins.

BACKGROUND

Globally, more than 7.5 billion people around the world consume milk and milk products. Demand for cow milk and dairy products is expected to keep increasing due to increased reliance on these products in developing countries as well as growth in the human population, which is expected to exceed 9 billion people by 2050.

Relying on animal agriculture to meet the growing demand for food is not a sustainable solution. According to the Food & Agriculture Organization of the United Nations, animal agriculture is responsible for 18% of all greenhouse gases, more than the entire transportation sector combined. Dairy cows alone account for 3% of this total.

In addition to impacting the environment, animal agriculture poses a serious risk to human health. A startling 80% of antibiotics used in the United States go towards treating animals, resulting in the development of antibiotic resistant microorganisms also known as superbugs. For years, food companies and farmers have administered antibiotics not only to sick animals, but also to healthy animals, to prevent illness. In September 2016, the United Nations announced the use of antibiotics in the food system as a crisis on par with Ebola and HIV.

It is estimated that cow milk accounts for 83% of global milk production. Accordingly, there is an urgent need for to provide bovine milk and/or essential high-quality proteins from bovine milk in a more sustainable and humane manner, instead of solely relying on animal farming. Also, there is a need for selectively producing the specific milk proteins that confer nutritional and clinical benefits, and/or do not provoke allergic responses.

BRIEF SUMMARY

Provided herein are compositions and methods for producing milk proteins in transgenic plants. In some embodiments, a milk protein is stably expressed in a transgenic plant by fusing it to a stable protein, such as a stable mammalian, avian, plant or fungal protein. The compositions and methods provided herein allow for safe, sustainable and humane production of milk proteins for commercial use, such as use in food compositions.

In some embodiments, the disclosure provides a stably transformed plant comprising in its genome: a recombinant DNA construct encoding a fusion protein, the fusion protein comprising: (i) an unstructured milk protein, and (ii) a structured animal protein; wherein the fusion protein is stably expressed in the plant in an amount of 1% or higher per total protein weight of soluble protein extractable from the plant.

In some embodiments, the disclosure provides a stably transformed plant, comprising in its genome: a recombinant DNA construct encoding a fusion protein, the fusion protein comprising: κ-casein; and β-lactoglobulin; wherein the fusion protein is stably expressed in the plant in an amount of 1% or higher per total protein weight of soluble protein extractable from the plant.

In some embodiments, the disclosure provides a recombinant fusion protein comprising: (i) an unstructured milk protein, and (ii) a structured animal protein.

In some embodiments, the disclosure provides a plant-expressed recombinant fusion protein, comprising: κ-casein and β-lactoglobulin.

Also provided are nucleic acids encoding the recombinant fusion proteins described herein.

Also provided are vectors comprising a nucleic acid encoding one or more recombinant fusion proteins described herein, wherein the recombinant fusion protein comprises: (i) an unstructured milk protein, and (ii) a structured animal protein.

Also provided are plants comprising the recombinant fusion proteins and/or the nucleic acids described herein.

The instant disclosure also provides a method for stably expressing a recombinant fusion protein in a plant, the method comprising: a) transforming a plant with a plant transformation vector comprising an expression cassette comprising: a sequence encoding a fusion protein, wherein the fusion protein comprises an unstructured milk protein, and a structured animal protein; and b) growing the transformed plant under conditions wherein the recombinant fusion protein is expressed in an amount of 1% or higher per total protein weight of soluble protein extractable from the plant.

Also provided herein are methods for making food compositions, the methods comprising: expressing the recombinant fusion protein in a plant; extracting the recombinant fusion protein from the plant; optionally, separating the milk protein from the structured animal protein or the structured plant protein; and creating a food composition using the milk protein or the fusion protein.

Also provided herein are food compositions comprising one or more recombinant fusion proteins as described herein.

Also provided are food compositions produced using any one of the methods disclosed herein.

These and other embodiments are described in detail below.

BRIEF DESCRIPTION OF THE DRAWINGS

The accompanying figures, which are incorporated herein and form a part of the specification, illustrate some, but not the only or exclusive, example embodiments and/or features.

It is intended that the embodiments and figures disclosed herein are to be considered illustrative rather than limiting.

FIGS. 1A, 1B, 1C, 1D, 1E, 1F, 1G, 1H, 1I, 1J, 1K, 1L, 1M, 1N, 1O, and 1P show expression cassettes having different combinations of fusions between structured and intrinsically unstructured proteins (not to scale). Coding regions and regulatory sequences are indicated as blocks (not to scale). As used in the figures, "L" refers to linker; "Sig" refers to a signal sequence that directs foreign proteins to protein storage vacuoles, "5' UTR" refers to the 5' untranslated region, and "KDEL" refers to an endoplasmic reticulum retention signal.

FIG. 9A shows detection of the fusion protein using a primary antibody raised against κ-casein (kCN). The kCN commercial protein is detected at an apparent MW of ~26 kDa (theoretical: 19 kDa—arrow). The fusion protein is detected at an apparent MW of ~40 kDa (theoretical: 38 kDa—arrowhead). FIG. 9B shows detection of the fusion protein using a primary antibody raised against β-lactoglobulin (LG). The LG commercial protein is detected at an apparent MW of ~18 kDa (theoretical: 18 kDa—arrow). The fusion protein is detected at an apparent MW of ~40 kDa (theoretical: 38 kDa—arrowhead). FIGS. 9C and 9D show protein gels as control for equal lane loading (image is taken at the end of the SDS run).

In FIG. 10A, a κ-casein protein is fused to a β-lactoglobulin protein. The κ-casein comprises a natural chymosin cleavage site (arrow 1). Cleavage of the fusion protein with rennet (or chymosin) yields two fragments: a para-kappa casein fragment, and a fragment comprising a κ-casein macropeptide fused to β-lactoglobulin. In some embodiments, a second protease cleavage site may be added at the C-terminus of the k-casein protein (i.e., at arrow 2), in order to further allow separation of the κ-casein macropeptide and the β-lactoglobulin. The second protease cleavage site may be a rennet cleavage site (e.g., a chymosin cleavage site), or it may be a cleavage site for a different protease. In FIG. 10B, a para-κ-casein protein is fused directly to β-lactoglobulin. A protease cleavage site (e.g., a rennet cleavage site) is added between the para-κ-casein and the β-lactoglobulin to allow for separation thereof. By fusing the para-κ-casein directly to the β-lactoglobulin, no κ-casein macropeptide is produced.

DETAILED DESCRIPTION

Figure 2:
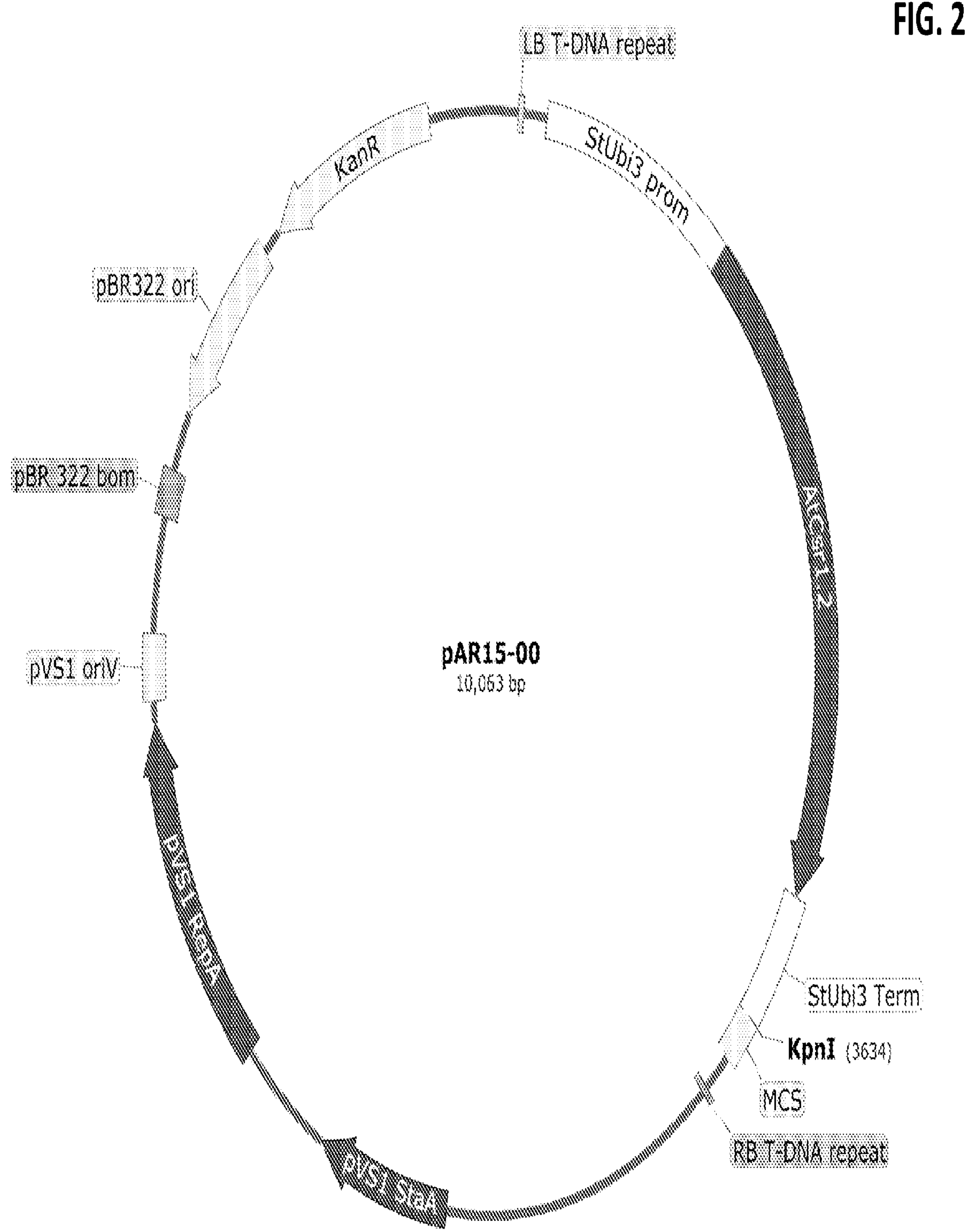
FIG. 2 shows the modified pAR15-00 cloning vector containing a selectable marker cassette conferring herbicide resistance. Coding regions and regulatory sequences are indicated as blocks (not to scale).

The following description includes information that may be useful in understanding the present disclosure. It is not an admission that any of the information provided herein is prior art or relevant to the presently claimed disclosures, or that any publication specifically or implicitly referenced is prior art.

Definitions

While the following terms are believed to be well understood by one of ordinary skill in the art, the following definitions are set forth to facilitate explanation of the presently disclosed subject matter.

All technical and scientific terms used herein, unless otherwise defined below, are intended to have the same meaning as commonly understood by one of ordinary skill in the art. References to techniques employed herein are intended to refer to the techniques as commonly understood in the art, including variations on those techniques and/or substitutions of equivalent techniques that would be apparent to one of skill in the art.

As used herein, the singular forms "a," "an," and "the: include plural referents unless the content clearly dictates otherwise.

The term "about" or "approximately" when immediately preceding a numerical value means a range (e.g., plus or minus 10% of that value). For example, "about 50" can mean 45 to 55, "about 25,000" can mean 22,500 to 27,500, etc., unless the context of the disclosure indicates otherwise, or is inconsistent with such an interpretation. For example, in a list of numerical values such as "about 49, about 50, about 55, . . . ", "about 50" means a range extending to less than half the interval(s) between the preceding and subsequent values, e.g., more than 49.5 to less than 52.5. Furthermore, the phrases "less than about" a value or "greater than about" a value should be understood in view of the definition of the term "about" provided herein. Similarly, the term "about" when preceding a series of numerical values or a range of values (e.g., "about 10, 20, 30" or "about 10-30") refers, respectively to all values in the series, or the endpoints of the range.

As used herein, "mammalian milk" can refer to milk derived from any mammal, such as bovine, human, goat, sheep, camel, buffalo, water buffalo, dromedary, llama and any combination thereof. In some embodiments, a mammalian milk is a bovine milk.

As used herein, "structured" refers to those proteins having a well-defined secondary and tertiary structure, and "unstructured" refers to proteins that do not have well defined secondary and/or tertiary structures. An unstructured protein may also be described as lacking a fixed or ordered three-dimensional structure. "Disordered" and "intrinsically disordered" are synonymous with unstructured.

As used herein, "rennet" refers to a set of enzymes typically produced in the stomachs of ruminant mammals. Chymosin, its key component, is a protease enzyme that cleaves κ-casein (to produce para-κ-casein). In addition to chymosin, rennet contains other enzymes, such as pepsin and lipase. Rennet is used to separate milk into solid curds (for cheesemaking) and liquid whey. Rennet or rennet substitutes are used in the production of most cheeses.

As used herein "whey" refers to the liquid remaining after milk has been curdled and strained, for example during cheesemaking. Whey comprises a collection of globular proteins, typically a mixture of β-lactoglobulin, α-lactalbumin, bovine serum albumin, and immunoglobulins.

The term "plant" includes reference to whole plants, plant organs, plant tissues, and plant cells and progeny of same, but is not limited to angiosperms and gymnosperms such as *Arabidopsis*, potato, tomato, tobacco, alfalfa, lettuce, carrot, strawberry, sugarbeet, cassava, sweet potato, soybean, lima bean, pea, chick pea, maize (corn), turf grass, wheat, rice, barley, sorghum, oat, oak, *eucalyptus*, walnut, palm and duckweed as well as fern and moss. Thus, a plant may be a monocot, a dicot, a vascular plant reproduced from spores such as fern or a nonvascular plant such as moss, liverwort, hornwort and algae. The word "plant," as used herein, also encompasses plant cells, seeds, plant progeny, propagule whether generated sexually or asexually, and descendants of any of these, such as cuttings or seed. Plant cells include suspension cultures, callus, embryos, meristematic regions, callus tissue, leaves, roots, shoots, gametophytes, sporophytes, pollen, seeds and microspores. Plants may be at various stages of maturity and may be grown in liquid or solid culture, or in soil or suitable media in pots, greenhouses or fields. Expression of an introduced leader, trailer or gene sequences in plants may be transient or permanent.

The term "vascular plant" refers to a large group of plants that are defined as those land plants that have lignified tissues (the xylem) for conducting water and minerals throughout the plant and a specialized non-lignified tissue (the phloem) to conduct products of photosynthesis. Vascular plants include the clubmosses, horsetails, ferns, gymnosperms (including conifers) and angiosperms (flowering plants). Scientific names for the group include Tracheophyta and Tracheobionta. Vascular plants are distinguished by two primary characteristics. First, vascular plants have vascular tissues which distribute resources through the plant. This feature allows vascular plants to evolve to a larger size than non-vascular plants, which lack these specialized conducting tissues and are therefore restricted to relatively small sizes. Second, in vascular plants, the principal generation phase is the sporophyte, which is usually diploid with two sets of chromosomes per cell. Only the germ cells and gametophytes are haploid. By contrast, the principal generation phase in non-vascular plants is the gametophyte, which is haploid with one set of chromosomes per cell. In these plants, only the spore stalk and capsule are diploid.

The term "non-vascular plant" refers to a plant without a vascular system consisting of xylem and phloem. Many non-vascular plants have simpler tissues that are specialized for internal transport of water. For example, mosses and leafy liverworts have structures that look like leaves, but are not true leaves because they are single sheets of cells with no stomata, no internal air spaces and have no xylem or phloem. Non-vascular plants include two distantly related groups. The first group are the bryophytes, which is further categorized as three separate land plant Divisions, namely Bryophyta (mosses), Marchantiophyta (liverworts), and Anthocerotophyta (hornworts). In all bryophytes, the primary plants are the haploid gametophytes, with the only diploid portion being the attached sporophyte, consisting of a stalk and sporangium. Because these plants lack lignified water-conducting tissues, they can't become as tall as most vascular plants. The second group is the algae, especially the green algae, which consists of several unrelated groups. Only those groups of algae included in the Viridiplantae are still considered relatives of land plants.

The term "plant part" refers to any part of a plant including but not limited to the embryo, shoot, root, stem, seed, stipule, leaf, petal, flower bud, flower, ovule, bract, trichome, branch, petiole, internode, bark, pubescence, tiller, rhizome, frond, blade, ovule, pollen, stamen, and the like. The two main parts of plants grown in some sort of media, such as soil or vermiculite, are often referred to as the "above-ground" part, also often referred to as the "shoots", and the "below-ground" part, also often referred to as the "roots".

The term "plant tissue" refers to any part of a plant, such as a plant organ. Examples of plant organs include, but are not limited to the leaf, stem, root, tuber, seed, branch, pubescence, nodule, leaf axil, flower, pollen, stamen, pistil, petal, peduncle, stalk, stigma, style, bract, fruit, trunk, carpel, sepal, anther, ovule, pedicel, needle, cone, rhizome, stolon, shoot, pericarp, endosperm, placenta, berry, stamen, and leaf sheath.

The term "seed" is meant to encompass the whole seed and/or all seed components, including, for example, the coleoptile and leaves, radicle and coleorhiza, scutellum, starchy endosperm, aleurone layer, pericarp and/or testa, either during seed maturation and seed germination.

The term "transgenic plant" means a plant that has been transformed with one or more exogenous nucleic acids. "Transformation" refers to a process by which a nucleic acid is stably integrated into the genome of a plant cell. "Stably integrated" refers to the permanent, or non-transient retention and/or expression of a polynucleotide in and by a cell genome. Thus, a stably integrated polynucleotide is one that is a fixture within a transformed cell genome and can be replicated and propagated through successive progeny of the cell or resultant transformed plant. Transformation may occur under natural or artificial conditions using various methods well known in the art. Transformation may rely on any known method for the insertion of nucleic acid sequences into a prokaryotic or eukaryotic host cell, including *Agrobacterium*-mediated transformation protocols, viral infection, whiskers, electroporation, heat shock, lipofection, polyethylene glycol treatment, micro-injection, and particle bombardment.

As used herein, the terms "stably expressed" or "stable expression" refer to expression and accumulation of a protein in a plant cell over time. In some embodiments, a protein may accumulate because it is not degraded by endogenous plant proteases. In some embodiments, a protein is considered to be stably expressed in a plant if it is present in the plant in an amount of 1% or higher per total protein weight of soluble protein extractable from the plant.

As used herein, the term "fusion protein" refers to a protein comprising at least two constituent proteins (or fragments or variants thereof) that are encoded by separate genes, and that have been joined so that they are transcribed and translated as a single polypeptide. In some embodiments, a fusion protein may be separated into its constituent proteins, for example by cleavage with a protease.

The term "recombinant" refers to nucleic acids or proteins formed by laboratory methods of genetic recombination (e.g., molecular cloning) to bring together genetic material from multiple sources, creating sequences that would not otherwise be found in the genome. A recombinant fusion protein is a protein created by combining sequences encoding two or more constituent proteins, such that they are expressed as a single polypeptide. Recombinant fusion proteins may be expressed in vivo in various types of host cells, including plant cells, bacterial cells, fungal cells, mammalian cells, etc. Recombinant fusion proteins may also be generated in vitro.

The term "promoter" or a "transcription regulatory region" refers to nucleic acid sequences that influence and/or promote initiation of transcription. Promoters are typically considered to include regulatory regions, such as enhancer or inducer elements. The promoter will generally be appropriate to the host cell in which the target gene is being expressed. The promoter, together with other transcriptional and translational regulatory nucleic acid sequences (also termed "control sequences"), is necessary to express any given gene. In general, the transcriptional and translational regulatory sequences include, but are not limited to, promoter sequences, ribosomal binding sites, transcriptional start and stop sequences, translational start and stop sequences, and enhancer or activator sequences.

The term signal peptide—also known as "signal sequence", "targeting signal", "localization signal", "localization sequence", "transit peptide", "leader sequence", or "leader peptide", is used herein to refer to an N-terminal peptide which directs a newly synthesized protein to a specific cellular location or pathway. Signal peptides are often cleaved from a protein during translation or transport, and are therefore not typically present in a mature protein.

The term "proteolysis" or "proteolytic" or "proteolyze" means the breakdown of proteins into smaller polypeptides or amino acids. Uncatalyzed hydrolysis of peptide bonds is extremely slow. Proteolysis is typically catalyzed by cellular enzymes called proteases, but may also occur by intramolecular digestion. Low pH or high temperatures can also cause proteolysis non-enzymatically. Limited proteolysis of a polypeptide during or after translation in protein synthesis often occurs for many proteins. This may involve removal of the N-terminal methionine, signal peptide, and/or the conversion of an inactive or non-functional protein to an active one.

The term "2A peptide", used herein, refers to nucleic acid sequence encoding a 2A peptide or the 2A peptide itself. The average length of 2A peptides is 18-22 amino acids. The designation "2A" refers to a specific region of picornavirus polyproteins and arose from a systematic nomenclature adopted by researchers. In foot-and-mouth disease virus (FMDV), a member of Picornaviridae family, a 2A sequence appears to have the unique capability to mediate cleavage at its own C-terminus by an apparently enzyme-independent, novel type of reaction. This sequence can also mediate cleavage in a heterologous protein context in a range of eukaryotic expression systems. The 2A sequence is inserted between two genes of interest, maintaining a single open reading frame. Efficient cleavage of the polyprotein can lead to co-ordinate expression of active two proteins of interest. Self-processing polyproteins using the FMDV 2A sequence could therefore provide a system for ensuring coordinated, stable expression of multiple introduced proteins in cells including plant cells.

The term "purifying" is used interchangeably with the term "isolating" and generally refers to the separation of a particular component from other components of the environment in which it was found or produced. For example, purifying a recombinant protein from plant cells in which it was produced typically means subjecting transgenic protein containing plant material to biochemical purification and/or column chromatography.

When referring to expression of a protein in a specific amount per the total protein weight of the soluble protein extractable from the plant ("TSP"), it is meant an amount of a protein of interest relative to the total amount of protein that may reasonably be extracted from a plant using standard methods. Methods for extracting total protein from a plant are known in the art. For example, total protein may be extracted from seeds by bead beating seeds at about 15000 rpm for about 1 min. The resulting powder may then be resuspended in an appropriate buffer (e.g., 50 mM Carbonate-Bicarbonate pH 10.8, 1 mM DTT, 1× Protease Inhibitor Cocktail). After the resuspended powder is incubated at about 4° C. for about 15 minutes, the supernatant may be collected after centrifuging (e.g., at 4000 g, 20 min, 4° C.). Total protein may be measured using standard assays, such as a Bradford assay. The amount of protein of interest may be measured using methods known in the art, such as an ELISA or a Western Blot.

When referring to a nucleic acid sequence or protein sequence, the term "identity" is used to denote similarity between two sequences. Sequence similarity or identity may be determined using standard techniques known in the art, including, but not limited to, the local sequence identity algorithm of Smith & Waterman, Adv. Appl. Math. 2, 482 (1981), by the sequence identity alignment algorithm of Needleman & Wunsch, J Mol. Biol. 48,443 (1970), by the search for similarity method of Pearson & Lipman, Proc. Natl. Acad. Sci. USA 85, 2444 (1988), by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., Nucl. Acid Res. 12, 387-395 (1984), or by inspection. Another suitable algorithm is the BLAST algorithm, described in Altschul et al., J Mol. Biol. 215, 403-410, (1990) and Karlin et al., Proc. Natl. Acad. Sci. USA 90, 5873-5787 (1993). A particularly useful BLAST program is the WU-BLAST-2 program which was obtained from Altschul et al., Methods in Enzymology, 266, 460-480 (1996); blast.wustl/edu/blast/README. WU-BLAST-2 uses several search parameters, which are optionally set to the default values. The parameters are dynamic values and are established by the program itself depending upon the composition of the particular sequence and composition of the particular database against which the sequence of interest is being searched; however, the values may be adjusted to increase sensitivity. Further, an additional useful algorithm is gapped BLAST as reported by Altschul et al, (1997) Nucleic Acids Res. 25, 3389-3402. As used herein, the terms “dicot” or “dicotyledon” or “dicotyledonous” refer to a flowering plant whose embryos have two seed leaves or cotyledons. Examples of dicots include, but are not limited to, *Arabidopsis*, tobacco, tomato, potato, sweet potato, cassava, alfalfa, lima bean, pea, chick pea, soybean, carrot, strawberry, lettuce, oak, maple, walnut, rose, mint, squash, daisy, *Quinoa*, buckwheat, mung bean, cow pea, lentil, lupin, peanut, fava bean, French beans (i.e., common beans), mustard, or cactus.

The terms “monocot” or “monocotyledon” or “monocotyledonous” refer to a flowering plant whose embryos have one cotyledon or seed leaf. Examples of monocots include, but are not limited to turf grass, maize (corn), rice, oat, wheat, barley, sorghum, orchid, iris, lily, onion, palm, and duckweed.

As used herein, a “low lactose product” is any food composition considered by the FDA to be “lactose reduced”, “low lactose”, or “lactose free”.

Unstructured Milk Proteins

The fusion proteins described herein may comprise one or more unstructured milk proteins. As used herein the term “milk protein” refers to any protein, or fragment or variant thereof, that is typically found in one or more mammalian milks. Examples of mammalian milk include, but are not limited to, milk produced by a cow, human, goat, sheep, camel, horse, donkey, dog, cat, elephant, monkey, mouse, rat, hamster, guinea pig, whale, dolphin, seal, sheep, buffalo, water buffalo, dromedary, llama, yak, zebu, reindeer, mole, otter, weasel, wolf, raccoon, walrus, polar bear, rabbit, or giraffe.

An “unstructured milk protein” is a milk protein that lacks a defined secondary structure, a defined tertiary structure, or a defined secondary and tertiary structure. Whether a milk protein is unstructured may be determined using a variety of biophysical and biochemical methods known in the art, such as small angle X-ray scattering, Raman optical activity, circular dichroism, nuclear magnetic resonance (NMR) and protease sensitivity. In some embodiments, a milk protein is considered to be unstructured if it is unable to be crystallized using standard techniques.

Illustrative unstructured milk proteins that may be used in the fusion proteins of the disclosure includes members of the casein family of proteins, such as α-S1 casein, α-S2 casein, β-casein, and κ-casein. The caseins are phosphoproteins, and make up approximately 80% of the protein content in bovine milk and about 20-45% of the protein in human milk. Caseins form a multi-molecular, granular structure called a casein micelle in which some enzymes, water, and salts, such as calcium and phosphorous, are present. The micellar structure of casein in milk is significant in terms of a mode of digestion of milk in the stomach and intestine and a basis for separating some proteins and other components from cow milk. In practice, casein proteins in bovine milk can be separated from whey proteins by acid precipitation of caseins, by breaking the micellar structure by partial hydrolysis of the protein molecules with proteolytic enzymes, or microfiltration to separate the smaller soluble whey proteins from the larger casein micelle. Caseins are relatively hydrophobic, making them poorly soluble in water.

In some embodiments, the casein proteins described herein (e.g., α-S1 casein, α-S2 casein, β-casein, and/or κ-casein) are isolated or derived from cow (*Bos taurus*), goat (*Capra hircus*), sheep (*Ovis aries*), water buffalo (*Bubalus bubalis*), dromedary camel (*Camelus dromedaries*), bactrian camel (*Camelus bactrianus*), wild yak (*Bos mutus*), horse (*Equus caballus*), donkey (*Equus asinus*), reindeer (*Rangifer tarandus*), eurasian elk (*Alces alces*), alpaca (*Vicugna pacos*), zebu (*Bos indicus*), llama (*Lama glama*), or human (*Homo sapiens*). In some embodiments, a casein protein (e.g., α-S1 casein, α-S2 casein, β-casein, or κ-casein) has at least 80%, at least 85%, at least 90%, at least 95%, at least 96%, at least 97%, at least 98%, or at least 99% identity with a casein protein from one or more of cow (*Bos taurus*), goat (*Capra hircus*), sheep (*Ovis aries*), water buffalo (*Bubalus bubalis*), dromedary camel (*Camelus dromedaries*), bactrian camel (*Camelus bactrianus*), wild yak (*Bos mutus*), horse (*Equus caballus*), donkey (*Equus asinus*), reindeer (*Rangifer tarandus*), eurasian elk (*Alces alces*), alpaca (*Vicugna pacos*), zebu (*Bos indicus*), llama (*Lama glama*), or human (*Homo sapiens*).

As used herein, the term “α-S1 casein” refers to not only the α-S1 casein protein, but also fragments or variants thereof. α-S1 casein is found in the milk of numerous different mammalian species, including cow, goat, and sheep. The sequence, structure and physical/chemical properties of α-S1 casein derived from various species is highly variable. An exemplary sequence for bovine α-S1 casein can be found at Uniprot Accession No. P02662, and an exemplary sequence for goat α-S1 casein can be found at GenBank Accession No. X59836.1.

As used herein, the term “α-S2 casein” refers to not only the α-S2 casein protein, but also fragments or variants thereof α-S2 is known as epsilon-casein in mouse, gamma-casein in rat, and casein-A in guinea pig. The sequence, structure and physical/chemical properties of α-S2 casein derived from various species is highly variable. An exemplary sequence for bovine α-S2 casein can be found at Uniprot Accession No. P02663, and an exemplary sequence for goat α-S2 casein can be found at Uniprot Accession No. P33049.

As used herein, the term “β-casein” refers to not only the β-casein protein, but also fragments or variants thereof. For example, A1 and A2 β-casein are genetic variants of the β-casein milk protein that differ by one amino acid (at amino acid 67, A2 β-casein has a proline, whereas A1 has a histidine). Other genetic variants of β-casein include the A3, B, C, D, E, F, H1, H2, I and G genetic variants. The sequence, structure and physical/chemical properties of β-casein derived from various species is highly variable.

Exemplary sequences for bovine β-casein can be found at Uniprot Accession No. P02666 and GenBank Accession No. M15132.1.

As used herein, the term "κ-casein" refers to not only the κ-casein protein, but also fragments or variants thereof. κ-casein is cleaved by rennet, which releases a macropeptide from the C-terminal region. The remaining product with the N-terminus and two-thirds of the original peptide chain is referred to as para-κ-casein. The sequence, structure and physical/chemical properties of κ-casein derived from various species is highly variable. Exemplary sequences for bovine κ-casein can be found at Uniprot Accession No. P02668 and GenBank Accession No. CAA25231.

In some embodiments, the unstructured milk protein is a casein protein, for example, α-S1 casein, α-S2 casein, β-casein, and or κ-casein. In some embodiments, the unstructured milk protein is κ-casein and comprises the sequence of SEQ ID NO: 4, or a sequence at least 90%, at least 95%, at least 96%, at least 97%, at least 98%, or at least 99% identical thereto. In some embodiments, the unstructured milk protein is para-κ-casein and comprises the sequence of SEQ ID NO: 2, or a sequence at least 90%, at least 95%, at least 96%, at least 97%, at least 98%, or at least 99% identical thereto. In some embodiments, the unstructured milk protein is β-casein and comprises the sequence of SEQ ID NO: 6, or a sequence at least 90%, at least 95%, at least 96%, at least 97%, at least 98%, or at least 99% identical thereto. In some embodiments, the unstructured milk protein is α-S1 casein and comprises the sequence SEQ ID NO: 8, or a sequence at least 90%, at least 95%, at least 96%, at least 97%, at least 98%, or at least 99% identical thereto. In some embodiments, unstructured milk protein is α-S2 casein and comprises the sequence SEQ ID NO: 84, or a sequence at least 90%, at least 95%, at least 96%, at least 97%, at least 98%, or at least 99% identical thereto.

In some embodiments, the unstructured milk protein comprises a sequence that is at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identical to SEQ ID NO: 4. In some embodiments, the unstructured milk protein comprises a sequence that is at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identical to SEQ ID NO: 2. In some embodiments, the unstructured milk protein comprises a sequence that is at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identical to SEQ ID NO: 6. In some embodiments, the unstructured milk protein comprises a sequence that is at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identical to SEQ ID NO: 8. In some embodiments, the unstructured milk protein comprises a sequence that is at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identical to SEQ ID NO: 84.

In some embodiments, α-S1 casein is encoded by the sequence of SEQ ID NO: 7, or a sequence at least 90%, at least 95%, at least 96%, at least 97%, at least 98%, or at least 99% identical thereto. In some embodiments, α-S2 casein is encoded by the sequence of SEQ ID NO: 83, or a sequence at least 90%, at least 95%, at least 96%, at least 97%, at least 98%, or at least 99% identical thereto. In some embodiments, β-casein is encoded by the sequence of SEQ ID NO: 5, or a sequence at least 90%, at least 95%, at least 96%, at least 97%, at least 98%, or at least 99% identical thereto. In some embodiments, κ-casein is encoded by the sequence of SEQ ID NO: 3, or a sequence at least 90%, at least 95%, at least 96%, at least 97%, at least 98%, or at least 99% identical thereto. In some embodiments, para-κ-casein is encoded by the sequence of SEQ ID NO: 1, or a sequence at least 90%, at least 95%, at least 96%, at least 97%, at least 98%, or at least 99% identical thereto.

In some embodiments, the unstructured milk protein is encoded by a sequence that is at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identical to SEQ ID NO: 7. In some embodiments, the unstructured milk protein is encoded by a sequence that is at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identical to SEQ ID NO: 83. In some embodiments, the unstructured milk protein is encoded by a sequence that is at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identical to SEQ ID NO: 3. In some embodiments, the unstructured milk protein is encoded by a sequence that is at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identical to SEQ ID NO: 1. In some embodiments, the unstructured milk protein is encoded by a sequence that is at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identical to SEQ ID NO: 5.

In some embodiments, the unstructured milk protein is a casein protein, and comprises a sequence that is at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identical to any one of SEQ ID NO: 85-133. In some embodiments, the unstructured milk protein is a casein protein and comprises the sequence of any one of SEQ ID NO: 85-133.

In some embodiments, the unstructured milk protein comprises a sequence that is at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identical to any one of SEQ ID NO: 85-98. In some embodiments, the unstructured milk protein comprises the sequence of any one of SEQ ID NO: 85-98.

In some embodiments, the unstructured milk protein comprises a sequence that is at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identical to any one of SEQ ID NO: 99-109. In some embodiments, the unstructured milk protein comprises the sequence of any one of SEQ ID NO: 99-109.

In some embodiments, the unstructured milk protein comprises a sequence that is at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identical to any one of SEQ ID NO: 110-120. In some embodiments, the unstructured milk protein comprises the sequence of any one of SEQ ID NO: 110-120.

In some embodiments, the unstructured milk protein comprises a sequence that is at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identical to any one of SEQ ID NO: 121-133. In some embodiments, the unstructured milk protein comprises the sequence of any one of SEQ ID NO: 121-133.

Structured Proteins

The fusion proteins described herein may comprise one or more structured proteins, including any fragment or variant thereof. The proteins may be, for example, structured animal proteins, or structured plant proteins. In some embodiments, the structured animal proteins are mammalian proteins. In some embodiments, the structured animal proteins are avian proteins. In some embodiments, the structured proteins are structured milk proteins.

Whether a milk protein is structured may be determined using a variety of biophysical and biochemical methods known in the art, such as small angle X-ray scattering, Raman optical activity, circular dichroism, and protease sensitivity. In some embodiments, a milk protein is considered to be structured if it has been crystallized or if it may be crystallized using standard techniques.

In some embodiments, the structured protein is not a protein that is typically used as a marker. As used herein, the term "marker" refers to a protein that produces a visual or other signal and is used to detect successful delivery of a vector (e.g., a DNA sequence) into a cell. Proteins typically used as a marker may include, for example, fluorescent proteins (e.g., green fluorescent protein (GFP)) and bacterial or other enzymes (e.g., β-glucuronidase (GUS), β-galactosidase, luciferase, chloramphenicol acetyltransferase). In some embodiments, the structured protein is a non-marker protein.

A non-limiting list of illustrative structured proteins that may be used in the fusion proteins described herein is provided in Table 1. In some embodiments, a fragment or variant of any one of the proteins listed in Table 1 may be used. In some embodiments, the structured protein may be an animal protein. For example, in some embodiments, the structured protein may be a mammalian protein. In some embodiments, the structured protein may be a plant protein. For example, the plant protein may be a protein that is not typically expressed in a seed. In some embodiments, the plant protein may be a storage protein, e.g., a protein that acts as a storage reserve for nitrogen, carbon, and/or sulfur. In some embodiments, the plant protein may inhibit one or more proteases. In some embodiments, the structured protein may be a fungal protein.

TABLE 1

Structured proteins

| Categories | Protein or Protein family | Native Species | Exemplary Uniprot Accession No. |
|---|---|---|---|
| Mammalian | Alpha-lactalbumin | Bovine (*Bos taurus*) | P00711 |
| | Beta-lactoglobulin | Bovine (*Bos taurus*) | P02754 |
| | Albumin | Bovine (*Bos taurus*) | P02769 |
| | Lysozyme | Bovine (*Bos taurus*) | Q6B411 |
| | Collagen family | Human (*Homo sapiens*) | Q02388, P02452, P08123, P02458 |
| | Hemoglobin | Bovine (*Bos taurus*) | P02070 |
| Avian proteins | Ovalbumin | Chicken (*Gallus gallus*) | P01012 |
| | Ovotransferrin | Chicken (*Gallus gallus*) | P02789 |
| | Ovoglobulin | Chicken (*Gallus gallus*) | I0J170 |
| | Lysozyme | Chicken (*Gallus gallus*) | P00698 |
| Plant Proteins | Oleosins | Soybean (*Glycine max*) | P29530, P29531 |
| | Leghemoglobin | Soybean (*Glycine max*) | Q41219 |
| | Extensin-like protein family | Soybean (*Glycine soja*) | A0A445JU93 |
| | Prolamine | Rice (*Oryza sativa*) | Q0DJ45 |
| | Glutenin | Wheat (*Sorghum bicolor*] | P10388 |
| | Gamma-kafirin preprotein | Wheat (*Sorghum bicolor*] | Q41506 |
| | Alpha globulin | Rice (*Oryza sativa*) | P29835 |
| | Basic 7S globulin precursor | Soybean (*Glycine max*) | P13917 |
| | 2S albumin | Soybean (*Glycine max*) | P19594 |
| | Beta-conglycinins | Soybean (*Glycine max*) | P0DO16, P0DO15, P0DO15 |
| | Glycinins | Soybean (*Glycine max*) | P04347, P04776, P04405 |
| | Canein | Sugar cane (*Saccharum officinarum*) | ABP64791.1 |

TABLE 1-continued

| Structured proteins | | | |
|---|---|---|---|
| Categories | Protein or Protein family | Native Species | Exemplary Uniprot Accession No. |
| | Zein | Corn (Zea Mays) | ABP64791.1 |
| | Patatin | Tomato (*Solanum lycopersicum*) | P07745 |
| | Kunitz-Trypsin inhibitor | Soybean (*Glycine max*) | Q39898 |
| | Bowman-Birk inhibitor | Soybean (*Glycine max*) | I1MQD2 |
| | Cystatine | Tomato (*Solanum lycopersicum*) | Q9SE07 |
| Fungal proteins | Hydrophobin I | Fungus (*Trichoderma reesei*) | P52754 |
| | Hydrophobin II | Fungus (*Trichoderma reesei*) | P79073 |

In some embodiments, the structured protein is an animal protein. In some embodiments, the structured protein is a mammalian protein. For example, the structured protein may be a mammalian protein selected from: β-lactoglobulin, α-lactalbumin, albumin, lysozyme, lactoferrin, lactoperoxidase, hemoglobin, collagen, and an immunoglobulin (e.g., IgA, IgG, IgM, IgE). In some embodiments, the structured mammalian protein is β-lactoglobulin and comprises the sequence of SEQ ID NO: 10, or a sequence at least 90%, at least 95%, at least 96%, at least 97%, at least 98%, or at least 99% identical thereto. In some embodiments, the structured mammalian protein is β-lactoglobulin and is encoded by the sequence of any one of SEQ ID NO: 9, 11, 12, or 13, or a sequence at least 90%, at least 95%, at least 96%, at least 97%, at least 98%, or at least 99% identical to any one of SEQ ID NO: 9, 11, 12, or 13. In some embodiments, the structured protein is an avian protein. For example, the structured protein may be an avian protein selected from: ovalbumin, ovotransferrin, lysozyme and ovoglobulin.

In some embodiments, the structured protein is a plant protein. For example, the structured protein may be a plant protein selected from: hydrophobin I, hydrophobin II, oleosins, leghemoglobin, extension-like protein family, prolamine, glutenin, gamma-kafirin preprotein, α-globulin, basic 7S globulin precursor, 2S albumin, β-conglycinins, glycinins, canein, zein, patatin, kunitz-trypsin inhibitor, bowman-birk inhibitor, and cystatine.

Fusion Proteins

Fusion Proteins Comprising an Unstructured Milk Protein and a Structured Animal (e.g., Mammalian) Protein In some embodiments, the fusion proteins described herein comprise (i) an unstructured milk protein, and (ii) a structured animal protein. In some embodiments, the fusion proteins described herein comprise (i) an unstructured milk protein, and (ii) a structured mammalian protein. In some embodiments, the fusion proteins described herein comprise (i) an unstructured milk protein, and (ii) a structured avian protein. In some embodiments, the fusion proteins described herein comprise (i) an unstructured milk protein, and (ii) a structured fungal protein.

In some embodiments, the fusion proteins comprise an unstructured milk protein, such as a casein protein. In some embodiments, the fusion proteins comprise an unstructured milk protein selected from α-S1 casein, α-S2 casein, β-casein, and κ-casein. In some embodiments, the fusion proteins comprise an unstructured milk protein isolated or derived from cow (*Bos taurus*), goat (*Capra hircus*), sheep (*Ovis aries*), water buffalo (*Bubalus bubalis*), dromedary camel (*Camelus dromedaries*), bactrian camel (*Camelus bactrianus*), wild yak (*Bos mutus*), horse (*Equus caballus*), donkey (*Equus asinus*), reindeer (*Rangifer tarandus*), eurasian elk (*Alces alces*), alpaca (*Vicugna pacos*), zebu (*Bos indicus*), llama (*Lama glama*), or human (*Homo sapiens*). In some embodiments, the fusion proteins comprise a casein protein (e.g., α-S1 casein, α-S2 casein, β-casein, or κ-casein) from cow (*Bos taurus*), goat (*Capra hircus*), sheep (*Ovis aries*), water buffalo (*Bubalus bubalis*), dromedary camel (*Camelus dromedaries*), bactrian camel (*Camelus bactrianus*), wild yak (*Bos mutus*), horse (*Equus caballus*), donkey (*Equus asinus*), reindeer (*Rangifer tarandus*), eurasian elk (*Alces alces*), alpaca (*Vicugna pacos*), zebu (*Bos indicus*), llama (*Lama glama*), or human (*Homo sapiens*).

In some embodiments, the unstructured milk protein is α-S1 casein. In some embodiments, the unstructured milk protein is α-S1 casein and comprises the sequence SEQ ID NO: 8, or a sequence at least 90%, at least 95%, at least 96%, at least 97%, at least 98%, or at least 99% identical thereto. In some embodiments, the unstructured milk protein is α-S1 casein and comprises the sequence of any one of SEQ ID NO: 99-109, or a sequence at least 90%, at least 95%, at least 96%, at least 97%, at least 98%, or at least 99% identical thereto In some embodiments, the unstructured milk protein is α-S2 casein. In some embodiments, the unstructured milk protein is α-S2 casein and comprises the sequence SEQ ID NO: 84, or a sequence at least 90%, at least 95%, at least 96%, at least 97%, at least 98%, or at least 99% identical thereto. In some embodiments, the unstructured milk protein is α-S2 casein and comprises the sequence of any one of SEQ ID NO: 110-120, or a sequence at least 90%, at least 95%, at least 96%, at least 97%, at least 98%, or at least 99% identical thereto.

In some embodiments, the unstructured milk protein is β-casein. In some embodiments, the unstructured milk protein is β-casein and comprises the sequence of SEQ ID NO: 6, or a sequence at least 90%, at least 95%, at least 96%, at least 97%, at least 98%, or at least 99% identical thereto. In some embodiments, the unstructured milk protein is β-casein and comprises the sequence of any one of SEQ ID NO: 121-133, or a sequence at least 90%, at least 95%, at least 96%, at least 97%, at least 98%, or at least 99% identical thereto.

In some embodiments, the unstructured milk protein is κ-casein. In some embodiments, the unstructured milk protein is κ-casein and comprises the sequence of SEQ ID NO: 4, or a sequence at least 90%, at least 95%, at least 96%, at least 97%, at least 98%, or at least 99% identical thereto. In some embodiments, the unstructured milk protein is κ-casein and comprises the sequence of any one of SEQ ID NO:

85-98, or a sequence at least 90%, at least 95%, at least 96%, at least 97%, at least 98%, or at least 99% identical thereto.

In some embodiments, the unstructured milk protein is para-κ-casein. In some embodiments, the unstructured milk protein is para-κ-casein and comprises the sequence of SEQ ID NO: 2, or a sequence at least 90%, at least 95%, at least 96%, at least 97%, at least 98%, or at least 99% identical thereto.

In some embodiments, the structured mammalian protein is β-lactoglobulin, α-lactalbumin, albumin, lysozyme, lactoferrin, lactoperoxidase, hemoglobin, collagen, or an immunoglobulin (e.g., IgA, IgG, IgM, or IgE). In some embodiments, the structured avian protein is ovalbumin, ovotransferrin, lysozyme or ovoglobulin.

In some embodiments, the structured mammalian protein is β-lactoglobulin. In some embodiments, the structured mammalian protein is β-lactoglobulin and comprises the sequence of SEQ ID NO: 10, or a sequence at least 90%, at least 95%, at least 96%, at least 97%, at least 98%, or at least 99% identical thereto.

In some embodiments, a fusion protein comprises a casein protein (e.g., κ-casein, para-κ-casein, β-casein, or α-S1 casein) and β-lactoglobulin. In some embodiments, a fusion protein comprises κ-casein and β-lactoglobulin (see, e.g., FIG. 3, FIG. 8, FIG. 10A-10B). In some embodiments, a fusion protein comprises para-κ-casein and β-lactoglobulin (see, e.g., FIG. 6, FIG. 7, FIG. 10A-10B). In some embodiments, a fusion protein comprises β-casein and (3-lactoglobulin. In some embodiments, a fusion protein comprises α-S1 casein and β-lactoglobulin.

In some embodiments, a plant-expressed recombinant fusion protein comprises κ-casein, or fragment thereof; and β-lactoglobulin, or fragment thereof. In some embodiments, the fusion protein comprises, in order from N-terminus to C-terminus, the κ-casein and the β-lactoglobulin.

Fusion Protein Comprising an Unstructured Milk Protein and a Structured Plant Protein In some embodiments, the fusion proteins described herein comprise (i) an unstructured milk protein, and (ii) a structured plant protein. In some embodiments, the unstructured milk protein is a casein protein, such as α-S1 casein, α-S2 casein, β-casein, or κ-casein. In some embodiments, the plant protein is selected from the group consisting of: hydrophobin I, hydrophobin II, oleosins, leghemoglobin, extension-like protein family, prolamine, glutenin, gamma-kafirin preprotein, α-globulin, basic 7S globulin precursor, 2S albumin, β-conglycinins, glycinins, canein, zein, patatin, kunitz-trypsin inhibitor, bowman-birk inhibitor, and cystatine.

Fusion Protein Structure

The fusion proteins described herein may have various different structures, in order to increase expression and/or accumulation in a plant or other host organism or cell. In some embodiments, a fusion protein comprises, in order from N-terminus to C-terminus, an unstructured milk protein and a structured animal (e.g., mammalian or avian) protein. In some embodiments, a fusion protein comprises, in order from N-terminus to C-terminus, a structured animal (e.g., mammalian or avian) protein and a milk protein. For example, in some embodiments, a fusion protein comprises, in order from N-terminus to C-terminus κ-casein and β-lactoglobulin. In some embodiments, a fusion protein comprises, in order from N-terminus to C-terminus β-lactoglobulin and κ-casein. In some embodiments, a fusion protein comprises, in order from N-terminus to C-terminus, para-κ-casein and β-lactoglobulin. In some embodiments, a fusion protein comprises, in order from N-terminus to C-terminus, β-lactoglobulin and para-κ-casein. In some embodiments, a fusion protein comprises, in order from N-terminus to C-terminus, β-casein and β-lactoglobulin. In some embodiments, a fusion protein comprises, in order from N-terminus to C-terminus, β-lactoglobulin and β-casein. In some embodiments, a fusion protein comprises, in order from N-terminus to C-terminus, α-S1 casein and β-lactoglobulin. In some embodiments, a fusion protein comprises, in order from N-terminus to C-terminus, β-lactoglobulin and α-S1 casein.

In some embodiments, a fusion protein comprises, in order from N-terminus to C-terminus, an unstructured milk protein and a structured plant protein. In some embodiments, a fusion protein comprises, in order from N-terminus to C-terminus, a structured plant protein and a milk protein. In some embodiments, a fusion protein comprises, in order from N-terminus to C-terminus, a casein protein and a structured plant protein. In some embodiments, a fusion protein comprises, in order from N-terminus to C-terminus, a structured plant protein and a casein protein.

In some embodiments, a fusion protein comprises a protease cleavage site. For example, in some embodiments, the fusion protein comprises an endoprotease, endopeptidase, and/or endoproteinase cleavage site. In some embodiments, the fusion protein comprises a rennet cleavage site. In some embodiments, the fusion protein comprises a chymosin cleavage site. In some embodiments, the fusion protein comprises a trypsin cleavage site.

The protease cleavage site may be located between the unstructured milk protein and the structured animal (e.g., mammalian or avian) protein, or between the unstructured milk protein and the structured plant protein, such that cleavage of the protein at the protease cleavage site will separate the unstructured milk protein from the structured animal (e.g., mammalian or avian) or plant protein.

In some embodiments, the protease cleavage site may be contained within the sequence of either the milk protein or the structured animal (e.g., mammalian or animal) or plant protein. In some embodiments, the protease cleavage site may be added separately, for example, between the two proteins.

In some embodiments, a fusion protein comprises a linker between the unstructured milk protein and the structured animal (e.g., mammalian or avian) protein, or between the unstructured milk protein and the structured plant protein. In some embodiments, the linker may comprise a peptide sequence recognizable by an endoprotease. In some embodiments, the linker may comprise a protease cleavage site. In some embodiments, the linker may comprise a self-cleaving peptide, such as a 2A peptide.

In some embodiments, a fusion protein may comprise a signal peptide. The signal peptide may be cleaved from the fusion protein, for example, during processing or transport of the protein within the cell. In some embodiments, the signal peptide is located at the N-terminus of the fusion protein. In some embodiments, the signal peptide is located at the C-terminus of the fusion protein.

In some embodiments, the signal peptide is selected from the group consisting of GmSCB1, StPat21, 2Sss, Sig2, Sig12, Sig8, Sig10, Sig11, and Coixss. In some embodiments, the signal peptide is Sig10 and comprises SEQ ID NO: 15, or a sequence at least 90%, at least 95%, at least 96%, at least 97%, at least 98%, or at least 99% identical thereto. In some embodiments, the signal peptide is Sig2 and comprises SEQ ID NO: 17, or a sequence at least 90%, at least 95%, at least 96%, at least 97%, at least 98%, or at least 99% identical thereto.

In some embodiments, the fusion protein comprises the sequence of SEQ ID NO: 71. In some embodiments, the fusion protein comprises the sequence of SEQ ID NO: 73. In some embodiments, the fusion protein comprises the sequence of SEQ ID NO: 75. In some embodiments, the fusion protein comprises the sequence of SEQ ID NO: 77. In some embodiments, the fusion protein comprises the sequence of SEQ ID NO: 79. In some embodiments, the fusion protein comprises the sequence of SEQ ID NO: 81. In some embodiments, the fusion protein comprises the sequence of SEQ ID NO: 135. In some embodiments, the fusion protein comprises the sequence of SEQ ID NO: 137.

In some embodiments, the fusion protein comprises the sequence of SEQ ID NO: 71, with 1, 2, 3, 4, 5, 6, 7, 8, 9, 10, or more amino acid substitutions. In some embodiments, the fusion protein comprises the sequence of SEQ ID NO: 73, with 1, 2, 3, 4, 5, 6, 7, 8, 9, 10, or more amino acid substitutions. In some embodiments, the fusion protein comprises the sequence of SEQ ID NO: 75, with 1, 2, 3, 4, 5, 6, 7, 8, 9, 10, or more amino acid substitutions. In some embodiments, the fusion protein comprises the sequence of SEQ ID NO: 77, with 1, 2, 3, 4, 5, 6, 7, 8, 9, 10, or more amino acid substitutions. In some embodiments, the fusion protein comprises the sequence of SEQ ID NO: 79, with 1, 2, 3, 4, 5, 6, 7, 8, 9, 10, or more amino acid substitutions. In some embodiments, the fusion protein comprises the sequence of SEQ ID NO: 81, with 1, 2, 3, 4, 5, 6, 7, 8, 9, 10, or more amino acid substitutions. In some embodiments, the fusion protein comprises the sequence of SEQ ID NO: 135, with 1, 2, 3, 4, 5, 6, 7, 8, 9, 10, or more amino acid substitutions. In some embodiments, the fusion protein comprises the sequence of SEQ ID NO: 137, with 1, 2, 3, 4, 5, 6, 7, 8, 9, 10, or more amino acid substitutions.

In some embodiments, the fusion protein comprises the sequence of SEQ ID NO: 71, or a sequence at least 90%, at least 95%, at least 96%, at least 97%, at least 98%, or at least 99% identical thereto. In some embodiments, the fusion protein comprises the sequence of SEQ ID NO: 73, or a sequence at least 90%, at least 95%, at least 96%, at least 97%, at least 98%, or at least 99% identical thereto. In some embodiments, the fusion protein comprises the sequence of SEQ ID NO: 75, or a sequence at least 90%, at least 95%, at least 96%, at least 97%, at least 98%, or at least 99% identical thereto. In some embodiments, the fusion protein comprises the sequence of SEQ ID NO: 77, or a sequence at least 90%, at least 95%, at least 96%, at least 97%, at least 98%, or at least 99% identical thereto. In some embodiments, the fusion protein comprises the sequence of SEQ ID NO: 79, or a sequence at least 90%, at least 95%, at least 96%, at least 97%, at least 98%, or at least 99% identical thereto. In some embodiments, the fusion protein comprises the sequence of SEQ ID NO: 81, or a sequence at least 90%, at least 95%, at least 96%, at least 97%, at least 98%, or at least 99% identical thereto. In some embodiments, the fusion protein comprises the sequence of SEQ ID NO: 135, or a sequence at least 90%, at least 95%, at least 96%, at least 97%, at least 98%, or at least 99% identical thereto. In some embodiments, the fusion protein comprises the sequence of SEQ ID NO: 137, or a sequence at least 90%, at least 95%, at least 96%, at least 97%, at least 98%, or at least 99% identical thereto.

In some embodiments, the fusion proteins have a molecular weight in the range of about 1 kDa to about 500 kDa, about 1 kDa to about 250 kDa, about 1 to about 100 kDa, about 10 to about 50 kDa, about 1 to about 10 kDa, about 10 to about 200 kDa, about 30 to about 150 kDa, about 30 kDa to about 50 kDa, or about 20 to about 80 kDa.

Nucleic Acids Encoding Fusion Proteins and Vectors Comprising the Same

Also provided herein are nucleic acids encoding the fusion proteins of the disclosure, for example fusion proteins comprising an unstructured milk protein and a structured animal (e.g., mammalian or avian) or plant protein. In some embodiments, the nucleic acids are DNAs. In some embodiments, the nucleic acids are RNAs.

In some embodiments, a nucleic acid comprises a sequence encoding a fusion protein. In some embodiments, a nucleic acid comprises a sequence encoding a fusion protein, which is operably linked to a promoter. In some embodiments, a nucleic acid comprises, in order from 5' to 3', a promoter, a 5' untranslated region (UTR), a sequence encoding a fusion protein, and a terminator.

The promoter may be a plant promoter. A "plant promoter" is a promoter capable of initiating transcription in plant cells. Examples of promoters under developmental control include promoters that preferentially initiate transcription in certain organs, such as leaves, roots, flowers, seeds and tissues such as fibers, xylem vessels, tracheids, or sclerenchyma. Such promoters are referred to as "tissue-preferred." Promoters which initiate transcription only in certain tissue are referred to as "tissue-specific." A "cell-type" specific promoter primarily drives expression in certain cell types in one or more organs, for example, vascular cells in leaves, roots, flowers, or seeds. An "inducible" promoter is a promoter which is under environmental control. Examples of environmental conditions that may affect transcription by inducible promoters include anaerobic conditions or the presence of light. Tissue-specific, tissue-preferred, cell-type specific, and inducible promoters constitute the class of "non-constitutive" promoters. A "constitutive" promoter is a promoter which is active under most environmental conditions.

In some embodiments, the promoter is a plant promoter derived from, for example soybean, lima bean, *Arabidopsis*, tobacco, rice, maize, barley, sorghum, wheat, pea, and/or oat. In some embodiments, the promoter is a constitutive or an inducible promoter. Exemplary constitutive promoters include, but are not limited to, the promoters from plant viruses such as the 35S promoter from CaMV and the promoters from such genes as rice actin; ubiquitin; pEMU; MAS and maize H3 histone. In some embodiments, the constitutive promoter is the ALS promoter, Xbal/Ncol fragment 5' to the *Brassica napus* ALS3 structural gene (or a nucleotide sequence similarity to said Xbal/Ncol fragment).

In some embodiments, the promoter is a plant tissue-specific or tissue-preferential promoter. In some embodiments, the promoter is isolated or derived from a soybean gene. Illustrative soybean tissue-specific promoters include AR-Pro1, AR-Pro2, AR-Pro3, AR-Pro4, AR-Pro5, AR-Pro6, AR-Pro7, AR-Pro8, and AR-Pro9.

In some embodiments, the plant is a seed-specific promoter. In some embodiments, the seed-specific promoter is selected from the group consisting of PvPhas, BnNap, AtOle1, GmSeed2, GmSeed3, GmSeed5, GmSeed6, GmSeed7, GmSeed8, GmSeed10, GmSeed11, GmSeed12, pBCON, GmCEP1-L, GmTHIC, GmBg7S1, GmGRD, GmOLEA, GmOLER, Gm2S-1, and GmBBld-II. In some embodiments, the seed-specific promoter is PvPhas and comprises the sequence of SEQ ID NO: 18, or a sequence at least 90%, at least 95%, at least 96%, at least 97%, at least 98%, or at least 99% identical thereto. In some embodiments, the seed-specific promoter is GmSeed2 and comprises the sequence of SEQ ID NO: 19, or a sequence at least 90%, at least 95%, at least 96%, at least 97%, at least 98%, or at least 99% identical thereto. In some embodiments, the promoter is a Cauliflower Mosaic Virus (CaMV) 35S promoter.

In some embodiments, the promoter is a soybean polyubiquitin (Gmubi) promoter, a soybean heat shock protein 90-like (GmHSP90L) promoter, a soybean Ethylene Response Factor (GmERF) promoter. In some embodiments, the promoter is a constitutive soybean promoter derived from GmScreamM1, GmScreamM4, GmScreamM8 genes or GmubiXL genes.

In some embodiments, the 5' UTR is selected from the group consisting of Arc5'UTR and glnB1UTR. In some embodiments, the 5' untranslated region is Arc5'UTR and comprises the sequence of SEQ ID NO: 20, or a sequence at least 90%, at least 95%, at least 96%, at least 97%, at least 98%, or at least 99% identical thereto.

In some embodiments, the terminator sequence is isolated or derived from a gene encoding Nopaline synthase, Arc5-1, an Extensin, Rb7 matrix attachment region, a Heat shock protein, Ubiquitin 10, Ubiquitin 3, and M6 matrix attachment region. In some embodiments, the terminator sequence is isolated or derived from a Nopaline synthase gene and comprises the sequence of SEQ ID NO: 22, or a sequence at least 90%, at least 95%, at least 96%, at least 97%, at least 98%, or at least 99% identical thereto.

In some embodiments, the nucleic acid comprises a 3' UTR. For example, the 3' untranslated region may be Arc5-1 and comprise SEQ ID NO: 21, or a sequence at least 90%, at least 95%, at least 96%, at least 97%, at least 98%, or at least 99% identical thereto.

In some embodiments the nucleic acid comprises a gene encoding a selectable marker. One illustrative selectable marker gene for plant transformation is the neomycin phosphotransferase II (nptll) gene, isolated from transposon Tn5, which, when placed under the control of plant regulatory signals, confers resistance to kanamycin. Another exemplary marker gene is the hygromycin phosphotransferase gene which confers resistance to the antibiotic hygromycin. In some embodiments, the selectable marker is of bacterial origin and confers resistance to antibiotics such as gentamycin acetyl transferase, streptomycin phosphotransferase, and aminoglycoside-3'-adenyl transferase, the bleomycin resistance determinant. In some embodiments, the selectable marker genes confer resistance to herbicides such as glyphosate, glufosinate or bromoxynil. In some embodiments, the selectable marker is mouse dihydrofolate reductase, plant 5-enolpyruvylshikimate-3-phosphate synthase and plant acetolactate synthase. In some embodiments, the selectable marker is acetolactate synthase (e.g., AtCsr1.2).

In some embodiments, a nucleic acid comprises an endoplasmic reticulum retention signal. For example, in some embodiments, a nucleic acid comprises a KDEL sequence (SEQ ID NO: 23). In some embodiments, the nucleic acid may comprise an endoplasmic reticulum retention signal selected from any one of SEQ ID NO: 23-70.

Shown in Table 2 are exemplary promoters, 5' UTRs, signal peptides, and terminators that may be used in the nucleic acids of the disclosure.

TABLE 2

Promoters, 5' UTRs, signal peptides and terminators

| Type | Name | Description | Native Species | Illustrative Accession No. (Glyma, GenBank) |
|---|---|---|---|---|
| Promoter | PvPhas | Phaseolin-1 (aka β-phaseolin) | Common bean (*Phaseolus vulgaris*) | J01263.1 |
| | BnNap | Napin-1 | Rapeseed (*Brassica napus*) | J02798.1 |
| | AtOle1 | Oleosin-1 (Ole1) | *Arabidopsis* (*Arabidopsis thaliana*) | X62353.1, AT4G25140 |
| | GmSeed2 | Gy1 (Glycinin 1) | Soybean (*Glycine max*) | Glyma.03G163500 |
| | GmSeed3 | cysteine protease | Soybean (*Glycine max*) | Glyma.08G116300 |
| | GmSeed5 | Gy5 (Glycinin 5) | Soybean (*Glycine max*) | Glyma.13G123500 |
| | GmSeed6 | Gy4 (Glycinin 4) | Soybean (*Glycine max*) | Glyma.10G037100 |
| | GmSeed7 | Kunitz trypsin protease inhibitor | Soybean (*Glycine max*) | Glyma.01G095000 |
| | GmSeed8 | Kunitz trypsin protease inhibitor | Soybean (*Glycine max*) | Glyma.08G341500 |
| | GmSeed10 | Legume Lectin Domain | Soybean (*Glycine max*) | Glyma.02G012600 |
| | GmSeed11 | β-conglycinin a subunit | Soybean (*Glycine max*) | Glyma.20G148400 |
| | GmSeed12 | β-conglycinin a' subunit | Soybean (*Glycine max*) | Glyma.10G246300 |
| | pBCON | β-conglycinin β subunit | Soybean (*Glycine max*) | Glyma.20G148200 |
| | GmCEP1-L | KDEL-tailed cysteine endopeptidase CEP1-like | Soybean (*Glycine max*) | Glyma06g42780 |
| | GmTHIC | phosphomethylpyrimidine synthase | Soybean (*Glycine max*) | Glyma11g26470 |
| | GmBg7S1 | Basic 7S globulin precursor | Soybean (*Glycine max*) | Glyma03g39940 |
| | GmGRD | glucose and ribitol dehydrogenase-like | Soybean (*Glycine max*) | Glyma07g38790 |
| | GmOLEA | Oleosin isoform A | Soybean (*Glycine max*) | Glyma.19g063400 |
| | GmOLEB | Oleosin isoform B | Soybean (*Glycine max*) | Glyma.16g071800 |
| | Gm2S-1 | 2S albumin | Soybean (*Glycine max*) | Glyma13g36400 |
| | GmBBId-II | Bowman-Birk protease inhibitor | Soybean (*Glycine max*) | Glyma16g33400 |
| 5'UTR | Arc5'UTR | arc5-1 gene | *Phaseolus vulgaris* | J01263.1 |
| | glnB1UTR | 65 bp of native glutamine synthase | Soybean (*Glycine max*) | AF301590.1 |
| Signal peptide | GmSCB1 | Seed coat BURP domain protein | Soybean (*Glycine max*) | Glyma07g28940.1 |
| | StPat21 | Patatin | Tomato (*Solanum lycopersicum*) | CAA27588 |

TABLE 2-continued

Promoters, 5' UTRs, signal peptides and terminators

| Type | Name | Description | Native Species | Illustrative Accession No. (Glyma, GenBank) |
|---|---|---|---|---|
| | 2Sss | 2S albumin | Soybean (*Glycine max*) | Glyma13g36400 |
| | Sig2 | Glycinin G1 N-terminal peptide | Soybean (*Glycine max*) | Glyma.03G163500 |
| | Sig12 | Beta-conglycinin alpha prime subunit N-terminal peptide | Soybean (*Glycine max*) | Glyma.10G246300 |
| | Sig8 | Kunitz trypsin inhibitor N-terminal peptide | Soybean (*Glycine max*) | Glyma.08G341500 |
| | Sig10 | Lectin N-terminal peptide from *Glycine max* | Soybean (*Glycine max*) | Glyma.02G012600 |
| | Sig11 | Beta-conglycinin alpha subunit N-terminal peptide | Soybean (*Glycine max*) | Glyma.20G148400 |
| | Coixss | Alpha-coixin N-terminal peptide from *Coix lacryma*-job | *Coix lacryma*-job | |
| | KDEL | C-terminal amino acids of sulfhydryl endopeptidase | *Phaseolus vulgaris* | |
| Terminator | NOS | Nopaline synthase gene termination sequence | *Agrobacterium tumefaciens* | |
| | ARC | arc5-1 gene termination sequence | *Phaseolus vulgaris* | J01263.1 |
| | EU | Extensin termination sequence | *Nicotiana tabacum* | |
| | Rb7 | Rb7 matrix attachment region termination sequence | *Nicotiana tabacum* | |
| | HSP or AtHSP | Heat shock termination sequence | *Arabidopsis thaliana* | |
| | AtUbi10 | Ubiquitin 10 termination sequence | *Arabidopsis thaliana* | |
| | Stubi3 | Ubiquitin 3 termination | *Solanum* tuberosum | |
| | TM6 | M6 matrix attachment region termination sequence | *Nicotiana tabacum* | |

Illustrative nucleic acids of the disclosure are provided in FIG. 1A-1P. In some embodiments a nucleic acid comprises, from 5' to 3', a promoter, a 5'UTR, a sequence encoding an unstructured milk protein, a sequence encoding a structured mammalian protein, an endoplasmic reticulum retention signal, and a terminator (See, e.g., FIG. 1A). In some embodiments a nucleic acid comprises, from 5' to 3', a promoter, a 5'UTR, a sequence encoding an unstructured milk protein, a sequence encoding a linker, a sequence encoding a structured mammalian protein, an endoplasmic reticulum retention signal, and a terminator (See, e.g., FIG. 1B). In some embodiments a nucleic acid comprises, from 5' to 3', a promoter, a 5'UTR, a sequence encoding an unstructured milk protein, a sequence encoding a linker, a sequence encoding a structured mammalian protein, and a terminator (See, e.g., FIG. 1C). In some embodiments a nucleic acid comprises, from 5' to 3', a promoter, a 5'UTR, a sequence encoding an unstructured milk protein, a sequence encoding a structured mammalian protein, and a terminator (See, e.g., FIG. 1D). In some embodiments a nucleic acid comprises, from 5' to 3', a promoter, a 5'UTR, a sequence encoding a structured mammalian protein, a sequence encoding an unstructured milk protein, an endoplasmic reticulum retention signal, and a terminator (See, e.g., FIG. 1E). In some embodiments a nucleic acid comprises, from 5' to 3', a promoter, a 5'UTR, a sequence encoding a structured mammalian protein, a sequence encoding a linker, a sequence encoding an unstructured milk protein, an endoplasmic reticulum retention signal, and a terminator (See, e.g., FIG. 1F). In some embodiments a nucleic acid comprises, from 5' to 3', a promoter, a 5'UTR, a sequence encoding a structured mammalian protein, a sequence encoding a linker, a sequence encoding an unstructured milk protein, and a terminator (See, e.g., FIG. 1G). In some embodiments a nucleic acid comprises, from 5' to 3', a promoter, a 5'UTR, a sequence encoding a structured mammalian protein, a sequence encoding an unstructured milk protein, and a terminator (See, e.g., FIG. 1H). In some embodiments a nucleic acid comprises, from 5' to 3', a promoter, a 5'UTR, a sequence encoding a signal peptide, a sequence encoding an unstructured milk protein, a sequence encoding a structured mammalian protein, an endoplasmic reticulum retention signal, and a terminator (See, e.g., FIG. 1I). In some embodiments a nucleic acid comprises, from 5' to 3', a promoter, a 5'UTR, a sequence encoding a signal peptide, a sequence encoding an unstructured milk protein, a sequence encoding a linker, a sequence encoding a structured mammalian protein, an endoplasmic reticulum retention signal, and a terminator (See, e.g., FIG. 1J). In some embodiments a nucleic acid comprises, from 5' to 3', a promoter, a 5'UTR, a sequence encoding a signal peptide, a sequence encoding an unstructured milk protein, a sequence encoding a linker, a sequence encoding a structured mammalian protein, and a terminator (See, e.g., FIG. 1K). In some embodiments a nucleic acid comprises, from 5' to 3', a promoter, a 5'UTR, a sequence encoding a signal peptide, a sequence encoding an unstructured milk protein, a sequence encoding a structured mammalian protein, and a terminator (See, e.g., FIG. 1L). In some embodiments a nucleic acid comprises, from 5' to 3', a promoter, a 5'UTR, a sequence encoding a signal peptide, a sequence encoding a structured mammalian protein, a sequence encoding an unstructured milk protein, an endoplasmic reticulum retention signal, and a terminator (See, e.g., FIG. 1M). In some embodiments a nucleic acid comprises, from 5' to 3', a promoter, a 5'UTR, a sequence encoding a signal peptide, a sequence encoding a structured mammalian protein, a sequence encoding a linker, a sequence encoding an unstructured milk protein, an endoplasmic reticulum retention signal, and a terminator (See, e.g., FIG. 1N). In some embodiments a nucleic acid comprises, from 5' to 3', a promoter, a 5'UTR, a sequence encoding a signal peptide, a sequence encoding a structured mammalian protein, a sequence encoding a linker, a sequence encoding an unstructured milk protein, and a terminator (See, e.g., FIG. 1O). In some embodiments a nucleic acid comprises, from 5' to 3', a promoter, a 5'UTR, a sequence encoding a signal peptide, a sequence encoding a structured mammalian protein, a sequence encoding an unstructured milk protein, and a terminator (See, e.g., FIG. 1P).

Figure 3:
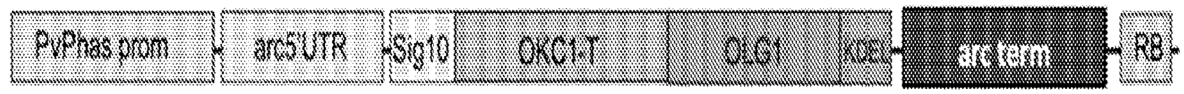
FIG. 3 shows an example expression cassette comprising a OKC1-T:OLG1 (Optimized Kappa Casein version 1:beta-lactoglobulin version 1, SEQ ID NOs: 71-72) fusion driven by PvPhas promoter fused with arc5'UTR:sig10, followed by the ER retention signal (KDEL) and the 3'UTR of the arc5-1 gene, "arc-terminator". "arc5'UTR" refers to the 5' untranslated region of the arc5-1 gene. "Sig10" refers to the lectin 1 gene signal peptide. "RB" refers to ribosomal binding site. Coding regions and regulatory sequences are indicated as blocks (not to scale).

In some embodiments, the nucleic acid comprises an expression cassette comprising a OKC1-T:OLG1 (Optimized Kappa Casein version 1:beta-lactoglobulin version 1) fusion driven by PvPhas promoter fused with arc5'UTR:sig10, followed by the ER retention signal (KDEL) and the 3'UTR of the arc5-1 gene, "arc-terminator" (See, e.g., FIG. 3). In some embodiments, the nucleic acid comprises SEQ ID NO: 72.

Figure 4:
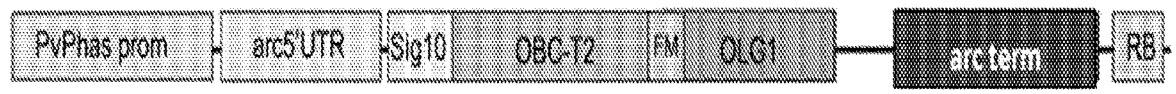
FIG. 4 shows an example expression cassette comprising a OBC-T2:FM:OLG1 (Optimized Beta Casein Truncated version 2:Chymosin cleavage site:beta-lactoglobulin version 1, SEQ ID NOs: 73-74) fusion driven by PvPhas promoter fused with arc5'UTR:sig10, followed by the 3'UTR of the arc5-1 gene, "arc-terminator". "arc5'UTR" refers to the 5' untranslated region of the arc5-1 gene. "Sig10" refers to the lectin 1 gene signal peptide. "RB" refers to ribosomal binding site. Coding regions and regulatory sequences are indicated as blocks (not to scale). The Beta Casein is "truncated" in that the bovine secretion signal is removed, and replaced with a plant targeting signal.

In some embodiments, the nucleic acid comprises an expression cassette comprising a OBC-T2:FM:OLG1 (Optimized Beta Casein Truncated version 2:Chymosin cleavage site:beta-lactoglobulin version 1) fusion driven by PvPhas promoter fused with arc5'UTR:sig10, followed by the 3'UTR of the arc5-1 gene, "arc-terminator" (See, e.g., FIG. 4). In some embodiments, the nucleic acid comprises SEQ ID NO: 74. The Beta Casein is "truncated" in that the bovine secretion signal is removed, and replaced with a plant targeting signal.

Figure 5:
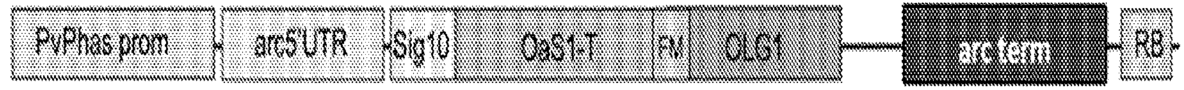
FIG. 5 shows an example expression cassette comprising a OaS1-T:FM:OLG1 (Optimized Alpha S1 Casein Truncated version 1:Chymosin cleavage site:beta-lactoglobulin version 1, SEQ ID NOs: 75-76) fusion driven by PvPhas promoter fused with arc5'UTR:sig10, followed by the 3'UTR of the arc5-1 gene, "arc-terminator". "arc5'UTR" refers to the 5' untranslated region of the arc5-1 gene. "Sig10" refers to the lectin 1 gene signal peptide. "RB" refers to ribosomal binding site. Coding regions and regulatory sequences are indicated as blocks (not to scale). The Alpha S1 Casein is "truncated" in that the bovine secretion signal is removed, and replaced with a plant targeting signal.

In some embodiments, the nucleic acid comprises an expression cassette comprising a OaS1-T:FM:OLG1 (Optimized Alpha S1 Casein Truncated version 1:Chymosin cleavage site:beta-lactoglobulin version 1) fusion driven by PvPhas promoter fused with arc5'UTR:sig10, followed by the 3'UTR of the arc5-1 gene, "arc-terminator" (See, e.g., FIG. 5). In some embodiments, the nucleic acid comprises SEQ ID NO: 76. The Alpha S1 is "truncated" in that the bovine secretion signal is removed, and replaced with a plant targeting signal.

Figure 6:
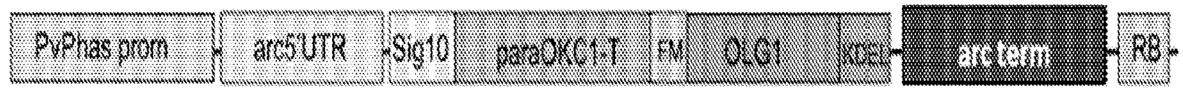
FIG. 6 shows an example expression cassette comprising a para-OKC1-T:FM:OLG1:KDEL (Optimized paraKappa Casein version 1:Chymosin cleavage site:beta-lactoglobulin version 1, SEQ ID NOs: 77-78) fusion driven by PvPhas promoter fused with arc5'UTR:sig 10, followed by the ER retention signal (KDEL) and the 3'UTR of the arc5-1 gene, "arc-terminator". "arc5'UTR" refers to the 5' untranslated region of the arc5-1 gene. "Sig10" refers to the lectin 1 gene signal peptide. "RB" refers to ribosomal binding site. Coding regions and regulatory sequences are indicated as blocks (not to scale).

In some embodiments, the nucleic acid comprises an expression cassette comprising a para-OKC1-T:FM:OLG1:KDEL (Optimized paraKappa Casein version 1:Chymosin cleavage site:beta-lactoglobulin version 1) fusion driven by PvPhas promoter fused with arc5'UTR:sig 10, followed by the ER retention signal (KDEL) and the 3'UTR of the arc5-1 gene, "arc-terminator" (See, e.g., FIG. 6). In some embodiments, the nucleic acid comprises SEQ ID NO: 78.

Figure 7:
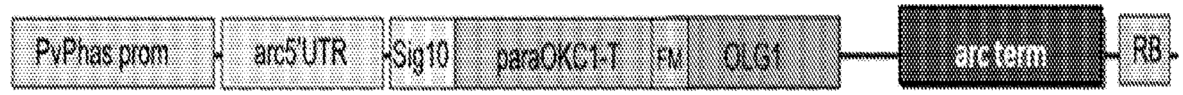
FIG. 7 shows an example expression cassette comprising a para-OKC1-T:FM:OLG1 (Optimized paraKappa Casein version 1:Chymosin cleavage site:beta-lactoglobulin version 1, SEQ ID NOs: 79-80) fusion driven by PvPhas promoter fused with arc5'UTR:sig 10, followed by the 3'UTR of the arc5-1 gene, "arc-terminator." "arc5'UTR" refers to the 5' untranslated region of the arc5-1 gene. "Sig10" refers to the lectin 1 gene signal peptide. "RB" refers to ribosomal binding site. Coding regions and regulatory sequences are indicated as blocks (not to scale).

In some embodiments, the nucleic acid comprises an expression cassette comprising a para-OKC1-T:FM:OLG1 (Optimized paraKappa Casein version 1:Chymosin cleavage site:beta-lactoglobulin version 1) fusion driven by PvPhas promoter fused with arc5'UTR:sig 10, followed by the 3'UTR of the arc5-1 gene, "arc-terminator" (See, e.g., FIG. 7). In some embodiments, the nucleic acid comprises SEQ ID NO: 80.

Figure 8:
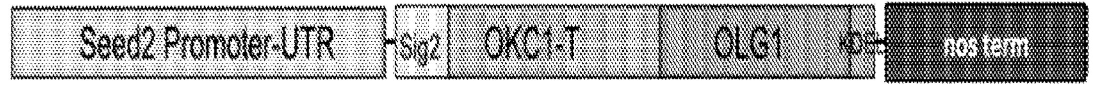
FIG. 8 shows an example expression cassette comprising a OKC1-T:OLG1 (Optimized Kappa Casein version 1:beta-lactoglobulin version 1, SEQ ID NOs: 81-82) fusion that is driven by the promoter and signal peptide of glycinin 1 (GmSeed2:sig2) followed by the ER retention signal (KDEL) and the nopaline synthase gene termination sequence, (nos term). Coding regions and regulatory sequences are indicated as blocks (not to scale).

In some embodiments, the nucleic acid comprises an expression cassette comprising a OKC1-T-OLG1 (Optimized Kappa Casein version 1:beta-lactoglobulin version 1) fusion that is driven by the promoter and signal peptide of glycinin 1 (GmSeed2:sig2) followed by the ER retention signal (KDEL) and the nopaline synthase gene termination sequence (nos term) (See, e.g., FIG. 8). In some embodiments, the nucleic acid comprises SEQ ID NO: 82.

In some embodiments, a nucleic acid encoding a fusion protein comprises the sequence of any one of SEQ ID NO: 72, 74, 76, 78, 80, 82, 134, or 136.

In some embodiments, the nucleic acids are codon optimized for expression in a host cell. Codon optimization is a process used to improve gene expression and increase the translational efficiency of a gene of interest by accommodating codon bias of the host organism (i.e., the organism in which the gene is expressed). Codon-optimized mRNA sequences that are produced using different programs or approaches can vary because different codon optimization strategies differ in how they quantify codon usage and implement codon changes. Some approaches use the most optimal (frequently used) codon for all instances of an amino acid, or a variation of this approach. Other approaches adjust codon usage so that it is proportional to the natural distribution of the host organism. These approaches include codon harmonization, which endeavors to identify and maintain regions of slow translation thought to be important for protein folding. Alternative approaches involve using codons thought to correspond to abundant tRNAs, using codons according to their cognate tRNA concentrations, selectively replacing rare codons, or avoiding occurrences of codon-pairs that are known to translate slowly. In addition to approaches that vary in the extent to which codon usage is considered as a parameter, there are hypothesis-free approaches that do not consider this parameter. Algorithms for performing codon optimization are known to those of skill in the art and are widely available on the Internet.

In some embodiments the nucleic acids are codon optimized for expression in a plant species. The plant species may be, for example, a monocot or a dicot. In some embodiments, the plant species is a dicot species selected from soybean, lima bean, *Arabidopsis*, tobacco, rice, maize, barley, sorghum, wheat and/or oat. In some embodiments, the plant species is soybean.

The nucleic acids of the disclosure may be contained within a vector. The vector may be, for example, a viral vector or a non-viral vector. In some embodiments, the non-viral vector is a plasmid, such as an *Agrobacterium* Ti plasmid. In some embodiments, the non-viral vector is a lipid nanoparticle.

In some embodiments, a vector comprises a nucleic acid encoding a recombinant fusion protein, wherein the recombinant fusion protein comprises: (i) an unstructured milk protein, and (ii) a structured animal (e.g., mammalian or avian) protein. In some embodiments, the vector is an *Agrobacterium* Ti plasmid.

In some embodiments, a method for expressing a fusion protein in a plant comprises contacting the plant with a vector of the disclosure. In some embodiments, the method comprises maintaining the plant or part thereof under conditions in which the fusion protein is expressed.

Plants Expressing Fusion Proteins

Also provided herein are transgenic plants expressing one or more fusion proteins of the disclosure. In some embodiments, the transgenic plants stably express the fusion protein. In some embodiments, the transgenic plants stably express the fusion protein in the plant in an amount of at least 1% per the total protein weight of the soluble protein extractable from the plant. For example, the transgenic plants may stably express the fusion protein in an amount of at least 1%, at least 1.5%, at least 2%, at least 2.5%, at least 3%, at least 3.5%, at least 4%, at least 4.5%, at least 5%, at least 5.5%, at least 6%, at least 6.5%, at least 7%, at least 7.5%, at least 8%, at least 8.5%, at least 9%, at least 9.5%, at least 10%, at least 10.5%, at least 11%, at least 11.5%, at least 12%, at least 12.5%, at least 13%, at least 13.5%, at least 14%, at least 14.5%, at least 15%, at least 15.5%, at least 16%, at least 16.5%, at least 17%, at least 17.5%, at least 18%, at least 18.5%, at least 19%, at least 19.5%, at least 20%, or more of total protein weight of soluble protein extractable from the plant.

In some embodiments, the transgenic plants stably express the fusion protein in an amount of less than about 1% of the total protein weight of soluble protein extractable from the plant. In some embodiments, the transgenic plants stably express the fusion protein in the range of about 1% to about 2%, about 3% to about 4%, about 4% to about 5%, about 5% to about 6%, about 6% to about 7%, about 7% to about 8%, about 8% to about 9%, about 9% to about 10%, about 10% to about 11%, about 11% to about 12%, about 12% to about 13%, about 13% to about 14%, about 14% to about 15%, about 15% to about 16%, about 16% to about 17%, about 17%, to about 18%, about 18% to about 19%, about 19% to about 20%, or more than about 20% of the total protein weight of soluble protein extractable from the plant.

In some embodiments, the transgenic plant stably express the fusion protein in an amount in the range of about 0.5% to about 3%, about 1% to about 4%, about 1% to about 5%, about 2% to about 5%, about 1% to about 10%, about 2% to about 10%, about 3% to about 10%, about 5 to about 12%, about 4% to about 10%, or about 5% to about 10%, about 4% to about 8%, about 5% to about 15%, about 5% to about 18%, about 10% to about 20%, or about 1% to about 20% of the total protein weight of soluble protein extractable from the plant.

In some embodiments, the fusion protein is expressed at a level at least 2-fold higher than an unstructured milk protein expressed individually in a plant. For example, in some embodiments, the fusion protein is expressed at a level at least 2-fold, at least 2.5-fold, at least 3-fold, at least 3.5-fold, at least 4-fold, at least 4.5-fold, at least 5-fold, at least 5.5-fold, at least 6-fold, at least 7-fold, at least 7.5-fold, at least 8-fold, at least 8.5-fold, at least 9-fold, at least 9.5-fold, at least 10-fold, at least 25-fold, at least 50-fold, or at least 100-fold higher than an unstructured milk protein expressed individually in a plant.

In some embodiments, the fusion protein accumulates in the plant at least 2-fold higher than an unstructured milk protein expressed without the structured animal (e.g., mammalian or avian) protein. For example, in some embodiments, the fusion protein accumulates in the plant at least 2-fold, at least 2.5-fold, at least 3-fold, at least 3.5-fold, at least 4-fold, at least 4.5-fold, at least 5-fold, at least 5.5-fold, at least 6-fold, at least 7-fold, at least 7.5-fold, at least 8-fold, at least 8.5-fold, at least 9-fold, at least 9.5-fold, at least 10-fold, at least 25-fold, at least 50-fold, or at least 100-fold higher than an unstructured milk protein expressed without the structured animal protein.

In some embodiments, a stably transformed plant comprises in its genome: a recombinant DNA construct encoding a fusion protein, wherein the fusion protein comprises (i) an unstructured milk protein, and (ii) a structured animal (e.g., mammalian or avian) protein. In some embodiments, the fusion protein is stably expressed in the plant in an amount of 1% or higher per the total protein weight of the soluble protein extractable from the plant. In some embodiments, the fusion protein is stably expressed in the plant in an amount of 2% or higher per the total protein weight of the soluble protein extractable from the plant. In some embodiments, the fusion protein is stably expressed in the plant in an amount of 3% or higher per the total protein weight of the soluble protein extractable from the plant. In some embodiments, the fusion protein is stably expressed in the plant in an amount of 4% or higher per the total protein weight of the soluble protein extractable from the plant. In some embodiments, the fusion protein is stably expressed in the plant in an amount of 5% or higher per the total protein weight of the soluble protein extractable from the plant. In some embodiments, the fusion protein is stably expressed in the plant in an amount of 6% or higher per the total protein weight of the soluble protein extractable from the plant. In some embodiments, the fusion protein is stably expressed in the plant in an amount of 7% or higher per the total protein weight of the soluble protein extractable from the plant. In some embodiments, the fusion protein is stably expressed in the plant in an amount of 8% or higher per the total protein weight of the soluble protein extractable from the plant. In some embodiments, the fusion protein is stably expressed in the plant in an amount of 9% or higher per the total protein weight of the soluble protein extractable from the plant. In some embodiments, the fusion protein is stably expressed in the plant in an amount of 10% or higher per the total protein weight of the soluble protein extractable from the plant. In some embodiments, the fusion protein is stably expressed in the plant in an amount of 11% or higher per the total protein weight of the soluble protein extractable from the plant. In some embodiments, the fusion protein is stably expressed in the plant in an amount of 12% or higher per the total protein weight of the soluble protein extractable from the plant. In some embodiments, the fusion protein is stably expressed in the plant in an amount of 13% or higher per the total protein weight of the soluble protein extractable from the plant. In some embodiments, the fusion protein is stably expressed in the plant in an amount of 14% or higher per the total protein weight of the soluble protein extractable from the plant. In some embodiments, the fusion protein is stably expressed in the plant in an amount of 15% or higher per the total protein weight of the soluble protein extractable from the plant. In some embodiments, the fusion protein is stably expressed in the plant in an amount of 16% or higher per the total protein weight of the soluble protein extractable from the plant. In some embodiments, the fusion protein is stably expressed in the plant in an amount of 17% or higher per the total protein weight of the soluble protein extractable from the plant. In some embodiments, the fusion protein is stably expressed in the plant in an amount of 18% or higher per the total protein weight of the soluble protein extractable from the plant. In some embodiments, the fusion protein is stably expressed in the plant in an amount of 19% or higher per the total protein weight of the soluble protein extractable from the plant. In some embodiments, the fusion protein is stably expressed in the plant in an amount of 20% or higher per the total protein weight of the soluble protein extractable from the plant.

In some embodiments, a stably transformed plant comprises in its genome: a recombinant DNA construct encoding a fusion protein, wherein the fusion protein comprises from N-terminus to C-terminus, the unstructured milk protein and the animal (e.g., mammalian or avian) protein. In some embodiments, the fusion protein comprises, from N-terminus to C-terminus, the structured animal (e.g., mammalian or avian) protein and the milk protein.

In some embodiments, a stably transformed plant comprises in its genome: a recombinant DNA construct encoding a fusion protein, wherein the fusion protein comprises an unstructured milk protein such as a casein protein. In In some embodiments, a stably transformed plant comprises in its genome: a recombinant DNA construct encoding a fusion protein, wherein the fusion protein comprises an unstructured milk protein selected from α-S1 casein, α-S2 casein, β-casein, and κ-casein. In some embodiments, the unstructured milk protein is α-S1 casein. In some embodiments, the unstructured milk protein is α-S1 casein and comprises the sequence SEQ ID NO: 8, or a sequence at least 90% identical thereto. In some embodiments, the unstructured milk protein is α-S2 casein. In some embodiments, the unstructured milk protein is α-S2 casein and comprises the sequence SEQ ID NO: 84, or a sequence at least 90% identical thereto. In some embodiments, the unstructured milk protein is β-casein. In some embodiments, the unstructured milk protein is β-casein and comprises the sequence of SEQ ID NO: 6, or a sequence at least 90% identical thereto. In some embodiments, the unstructured milk protein is κ-casein. In some embodiments, the unstructured milk protein is κ-casein and comprises the sequence of SEQ ID NO: 4, or a sequence at least 90% identical thereto. In some embodiments, the unstructured milk protein is para-κ-casein. In some embodiments, the unstructured milk protein is para-κ-casein and comprises the sequence of SEQ ID NO: 2, or a sequence at least 90% identical thereto.

In some embodiments, a stably transformed plant comprises in its genome: a recombinant DNA construct encoding a fusion protein, wherein the fusion protein comprises a structured mammalian protein selected from β-lactoglobulin, α-lactalbumin, albumin, lysozyme, lactoferrin, lactoperoxidase, hemoglobin, collagen, and an immunoglobulin (e.g., IgA, IgG, IgM, or IgE). In some embodiments, the structured mammalian protein is β-lactoglobulin. In some embodiments, the structured mammalian protein is β-lactoglobulin and comprises the sequence of SEQ ID NO: 10, or a sequence at least 90% identical thereto. In some embodiments, a stably transformed plant comprises in its genome: a recombinant DNA construct encoding a fusion protein, wherein the fusion protein comprises a structured avian protein selected from lysozyme, ovalbumin, ovotransferrin, and ovoglobulin.

In some embodiments, a stably transformed plant comprises in its genome: a recombinant DNA construct encoding a fusion protein, wherein the fusion protein comprises a casein protein and β-lactoglobulin. In some embodiments, a stably transformed plant comprises in its genome: a recombinant DNA construct encoding a fusion protein, wherein the fusion protein comprises κ-casein and β-lactoglobulin. In some embodiments, the fusion protein comprises para-κ-casein and β-lactoglobulin. In some embodiments, the fusion protein comprises β-casein and 3-lactoglobulin. In some embodiments, the fusion protein comprises α-S1 casein and β-lactoglobulin.

In some embodiments, a stably transformed plant comprises in its genome: a recombinant DNA construct encoding a fusion protein; wherein the fusion protein comprises (1) κ-casein, and (ii) β-lactoglobulin. In some embodiments; and wherein the fusion protein is stably expressed in the plant in an amount of 1% or higher per the total protein weight of the soluble protein extractable from the plant.

In some embodiments, the stably transformed plant is a monocot. For example, in some embodiments, the plant may be a monocot selected from turf grass, maize (corn), rice, oat, wheat, barley, sorghum, orchid, iris, lily, onion, palm, and duckweed.

In some embodiments, the stably transformed plant is a dicot. For example, in some embodiments, the plant may be a dicot selected from *Arabidopsis*, tobacco, tomato, potato, sweet potato, cassava, alfalfa, lima bean, pea, chick pea, soybean, carrot, strawberry, lettuce, oak, maple, walnut, rose, mint, squash, daisy, *Quinoa*, buckwheat, mung bean, cow pea, lentil, lupin, peanut, fava bean, French beans (i.e., common beans), mustard, or cactus. In some embodiments, the plant is a soybean (*Glycine max*).

In some embodiments, the plant is a non-vascular plant selected from moss, liverwort, hornwort or algae. In some embodiments, the plant is a vascular plant reproducing from spores (e.g., a fern).

In some embodiments, the recombinant DNA construct is codon-optimized for expression in the plant. For example, in some embodiments, the recombinant DNA construct is codon-optimized for expression in a soybean plant.

The transgenic plants described herein may be generated by various methods known in the art. For example, a nucleic acid encoding a fusion protein may be contacted with a plant, or a part thereof, and the plant may then be maintained under conditions wherein the fusion protein is expressed. In some embodiments, the nucleic acid is introduced into the plant, or part thereof, using one or more methods for plant transformation known in the art, such as *Agrobacterium*-mediated transformation, particle bombardment-medicated transformation, electroporation, and microinjection.

In some embodiments, a method for stably expressing a recombinant fusion protein in a plant comprises (i) transforming a plant with a plant transformation vector comprising an expression cassette comprising: a sequence encoding a fusion protein, wherein the fusion protein comprises an unstructured milk protein, and a structured animal (e.g., mammalian or avian) protein; and (ii) growing the transformed plant under conditions wherein the recombinant fusion protein is expressed. In some embodiments, the recombinant fusion protein is expressed in an amount of 1% or higher per the total protein weight of the soluble protein extractable from the plant. In some embodiments, the unstructured milk protein is κ-casein. In some embodiments, the structured mammalian protein is β-lactoglobulin. In some embodiments, the unstructured milk protein is κ-casein and the structured mammalian protein is β-lactoglobulin.

Food Compositions Comprising a Fusion Protein

Figure 11:
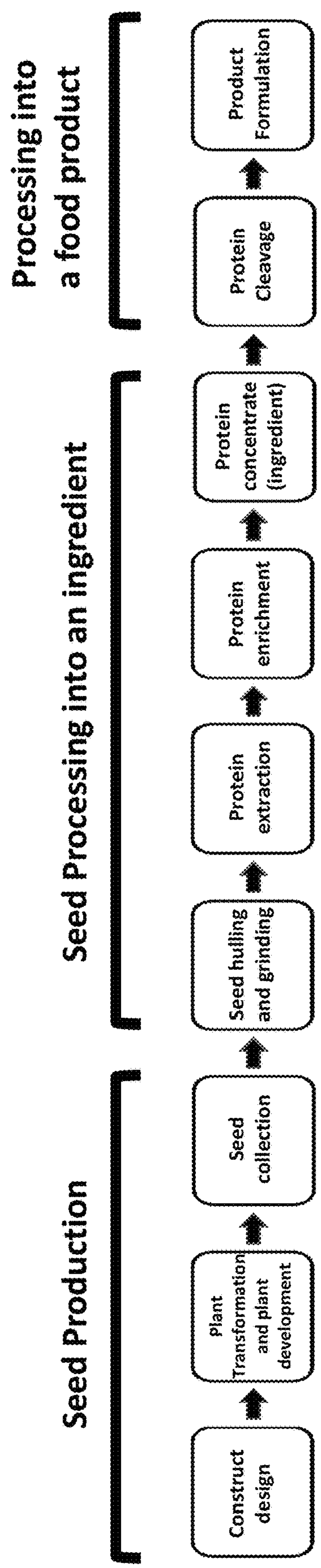
FIG. 11 is a flow-chart showing an illustrative process for producing a food composition comprising an unstructured milk protein, as described herein.

The fusion proteins and transgenic plants described herein may be used to prepare food compositions. The fusion protein may be used directly to prepare the food composition (i.e., in the form of a fusion protein), or the fusion protein may first be separated into its constituent proteins. For example, in some embodiments, a food composition may comprise either (i) a fusion protein, (ii) an unstructured milk protein, (iii) a structured mammalian, avian, or plant protein, or (iv) an unstructured milk protein and a structured mammalian, avian, or plant protein. An illustrative method for preparing a food composition of the disclosure is provided in FIG. 11.

In some embodiments, the fusion proteins and transgenic plants described herein may be used to prepare a food composition selected from cheese and processed cheese products, yogurt and fermented dairy products, directly acidified counterparts of fermented dairy products, cottage cheese dressing, frozen dairy products, frozen desserts, desserts, baked goods, toppings, icings, fillings, low-fat spreads, dairy-based dry mixes, soups, sauces, salad dressing, geriatric nutrition, creams and creamers, analog dairy products, follow-up formula, baby formula, infant formula, milk, dairy beverages, acid dairy drinks, smoothies, milk tea, butter, margarine, butter alternatives, growing up milks, low-lactose products and beverages, medical and clinical nutrition products, protein/nutrition bar applications, sports beverages, confections, meat products, analog meat products, meal replacement beverages, and weight management food and beverages.

In some embodiments the fusion proteins and transgenic plants described herein may be used to prepare a dairy product. In some embodiments, the dairy product is a fermented dairy product. An illustrative list of fermented dairy products includes cultured buttermilk, sour cream, yogurt, skyr, leben, lassi, or kefir. In some embodiments the fusion proteins and transgenic plants described herein may be used to prepare cheese products.

In some embodiments the fusion proteins and transgenic plants described herein may be used to prepare a powder containing a milk protein. In some embodiments, the fusion proteins and transgenic plants described herein may be used to prepare a low-lactose product.

In some embodiments, a method for making a food composition comprises, expressing a recombinant fusion protein of the disclosure in a plant, extracting the recombinant fusion protein from the plant, optionally separating the milk protein from the structured mammalian or plant protein, and creating a food composition using the fusion protein and/or the milk protein.

The recombinant fusion proteins may be extracted from a plant using standard methods known in the art. For example, the fusion proteins may be extracted using solvent or aqueous extraction. In some embodiments, the fusion proteins may be extracted using phenol extraction. Once extracted, the fusion proteins may be maintained in a buffered environment (e.g., Tris, MOPS, HEPES), in order to avoid sudden changes in the pH. The fusion proteins may also be maintained at a particular temperature, such as 4° C. In some embodiments, one or more additives may be used to aid the extraction process (e.g., salts, protease/peptidase inhibitors, osmolytes, reducing agents, etc.)

In some embodiments, a method for making a food composition comprises, expressing a recombinant fusion protein of the disclosure in a plant, extracting one or both of the unstructured milk protein and the structured mammalian or plant protein from the plant, and creating a food composition using the milk protein.

In some embodiments, the milk protein and the structured mammalian or plant protein are separated from one another in the plant cell, prior to extraction. In some embodiments, the milk protein is separated from the structured mammalian or plant protein after extraction, for example by contacting the fusion protein with an enzyme that cleaves the fusion protein. The enzyme may be, for example, chymosin. In some embodiments, the fusion protein is cleaved using rennet.

All references, articles, publications, patents, patent publications, and patent applications cited herein are incorporated by reference in their entireties for all purposes. However, mention of any reference, article, publication, patent, patent publication, and patent application cited herein is not, and should not be taken as an acknowledgment or any form of suggestion that they constitute valid prior art or form part of the common general knowledge in any country in the world, or that they disclose essential matter.

EXAMPLES

The following experiments demonstrate different recombinant fusion constructs of milk proteins and structured proteins, as well as methods of testing and producing the recombinant proteins, and food compositions produced from the extracted protein. While the examples below describe expression in soybean, it will be understood by those skilled in the art that the constructs and methods disclosed herein may be tailored for expression in any organism.

Example 1: Construction of Expression Vectors for Plant Transformation for Stable Expression of Recombinant Fusion Proteins Binary Vector Design While a number of vectors may be utilized for expression of the fusion proteins disclosed herein, the example constructs described below were built in the binary pCAMBIA3300 (Creative Biogene, VET1372) vector, which was customized for soybean transformation and selection. In order to modify the vector, pCAMBIA3300 was digested with HindIII and AseI allowing the release of the vector backbone (LB T-DNA repeat_KanR_pBR322 ori_pBR322 bom_pVS1 oriV_pVs1 repA_pVS1 StaA_RB T-DNA repeat). The 6598 bp vector backbone was gel extracted and a synthesized multiple cloning site (MCS) was ligated via In-Fusion cloning (In-Fusion® HD Cloning System CE, available on the world wide web at clontech.com) to allow modular vector modifications. A cassette containing the *Arabidopsis thaliana* Csr1.2 gene for acetolactate synthase was added to the vector backbone to be used as a marker for herbicide selection of transgenic plants. In order to build this cassette, the regulatory sequences from *Solanum tuberosum* ubiquitin/ribosomal fusion protein promoter (StUbi3 prom; −1 to −922 bp) and terminator (StUbi3 term; 414 bp) (GenBank accession no. L22576.1) were fused to the mutant (S653N) acetolactate synthase gene (Csr1.2; GenBank accession no. X51514.1) (Sathasivan et al, 1990; Ding et al, 2006) to generate imazapyr-resistant traits in soybean plants. The selectable marker cassette was introduced into the digested (EcoRI) modified vector backbone via In-Fusion cloning to form vector pAR15-00 (FIG. 2).

Recombinant DNA constructs were designed to express milk proteins (intrinsically unstructured and structured) in transgenic plants. The coding regions of the expression cassettes outlined below contain a fusion of codon-optimized nucleic acid sequences encoding bovine milk proteins, or a functional fragment thereof. To enhance protein expression in soybean, the nucleic acid sequences encoding β-lactoglobulin (GenBank accession no. X14712.1) κ-casein (GenBank accession no. CAA25231), β-casein (GenBank accession no. M15132.1), and αS1-casein (GenBank accession no. X59836.1) were codon optimized using *Glycine max* codon bias and synthesized (available on the world wide web at idtdna.com/CodonOpt). The signal sequences were removed (i.e., making the constructs "truncated") and the new versions of the genes were renamed as OLG1 (β-lactoglobulin version 1, SEQ ID NO: 9), OLG2 (β-lactoglobulin version 2, SEQ ID NO: 11), OLG3 (β-lactoglobulin version 3, SEQ ID NO: 12), OLG4 (β-lactoglobulin version 4, SEQ ID NO: 13), OKC1-T (Optimized κ-casein Truncated version 1, SEQ ID NO: 3), paraOKC1-T (only the para-κ portion of OKC1-T, SEQ ID NO: 1), OBC-T2 (Optimized β-casein Truncated version 2, SEQ ID NO: 5), and OaS1-T (Optimized αS1-casein Truncated version 1, SEQ ID NO: 7). As will be understood by those skilled in the art, any codon optimized nucleic acid sequences can present from 60% to 100% identity to the native version of the nucleic acid sequence.

All the expression cassettes described below and shown in FIG. 3-8 contained codon-optimized nucleic acid sequences encoding bovine milk proteins, or a functional fragment thereof, a seed specific promoter, a 5'UTR, a signal sequence (Sig) that directs foreign proteins to the protein storage vacuoles, and a termination sequence. In some versions of the constructs a linker (FM) such as chymosin cleavage site, was placed between the two proteins and/or a C-terminal KDEL sequence for ER retention was included. Expression cassettes were inserted in the pAR15-00 vector described above utilizing a KpnI restriction site with the MCS (FIG. 2). Coding regions and regulatory sequences are indicated as blocks (not to scale) in FIG. 3-8.

κ-Casein-β-Lactoglobulin Fusion with KDEL

Shown in FIG. 3 is an example expression cassette comprising κ-casein (OKC1-T, SEQ ID NO: 3) and β-lactoglobulin (OLG1, SEQ ID NO: 9). The regulatory sequences that were used in order to produce the heterologous milk proteins in soybean seeds include the promoter of the beta-phaseolin storage protein gene (PvPhas prom; −1 to −1543; GenBank accession no. J01263.1, SEQ ID NO: 18); the 5'UTR of the arc5-1 gene (arc5'UTR; −1 to −13; GenBank accession no. Z50202, SEQ ID NO: 20) (De Jaeger et al, 2002); the signal peptide of Lectin 1 gene 1 (sig10; +1 to +93; GenBank accession no. Glyma.02G012600, SEQ ID NO: 14) (Darnowski et al, 20020); and, the 3'UTR of the arc5-1 gene, (arc term 1197 bp; GenBank accession no. Z50202.1, SEQ ID NO: 21)(De Jaeger et al, 2002). A C-terminal KDEL (SEQ ID NO: 23) was also included for ER retention.

β-Casein-β-Lactoglobulin Fusion with Linker

Shown in FIG. 4 is an example expression cassette comprising β-casein (OBC-T2, SEQ ID NO: 5) and β-lactoglobulin (OLG1, SEQ ID NO: 9). The regulatory sequences that were used in order to produce the heterologous milk proteins in soybean seeds include the promoter of the beta-phaseolin storage protein gene (PvPhas prom; −1 to −1543; GenBank accession no. J01263.1, SEQ ID NO: 18); the 5'UTR of the arc5-1 gene (arc5'UTR; −1 to −13; GenBank accession no. Z50202, SEQ ID NO: 20) (De Jaeger et al, 2002); the signal peptide of Lectin 1 gene 1 (sig10; +1 to +93; accession no. Glyma.02G012600, SEQ ID NO: 14) (Darnowski et al, 2002); and, the 3'UTR of the arc5-1 gene, (arc term 1197 bp; accession no. Z50202.1, SEQ ID NO: 21) (De Jaeger, et al 2002). A linker (FM) comprising a chymosin cleavage site was inserted between the two proteins.

αS1-Casein-β-Lactoglobulin Fusion with Linker

Shown in FIG. 5 is an example expression cassette comprising αS1-casein (OaS1-T, SEQ ID NO: 7) and β-lactoglobulin (OLG1, SEQ ID NO: 9). The regulatory sequences that were used in order to produce the heterologous milk proteins in soybean seeds include the promoter of the beta-phaseolin storage protein gene (PvPhas prom; −1 to −1543; GenBank accession no. J01263.1, SEQ ID NO: 18); the 5'UTR of the arc5-1 gene (arc5'UTR; −1 to −13; GenBank accession no. Z50202, SEQ ID NO: 20) (De Jaeger et al, 2002); the signal peptide of Lectin 1 gene 1 (sig10; +1 to +93; accession no. Glyma.02G012600, SEQ ID NO: 14) (Darnowski et al, 2002); and, the 3'UTR of the arc5-1 gene, (arc term 1197 bp; GenBank accession no. Z50202.1, SEQ ID NO: 21)(De Jaeger et al, 2002). A linker (FM) comprising a chymosin cleavage site was inserted between the two proteins.

Para-κ-Casein-β-Lactoglobulin Fusion with Linker and KDEL

Shown in FIG. 6 is an example expression cassette comprising para-κ-casein (paraOKC1-T, SEQ ID NO: 1) and β-lactoglobulin (OLG1, SEQ ID NO: 9). The regulatory sequences that were used in order to produce the heterologous milk proteins in soybean seeds include the promoter of the beta-phaseolin storage protein gene (PvPhas prom; −1 to −1543; GenBank accession no. J01263.1, SEQ ID NO: 18); the 5'UTR of the arc5-1 gene (arc5'UTR; −1 to −13; GenBank accession no. Z50202, SEQ ID NO: 20) (De Jaeger et al, 2002); the signal peptide of Lectin 1 gene 1 (sig10; +1 to +93; GenBank accession no. Glyma.02G012600, SEQ ID NO: 14) (Darnowski et al, 2002); and, the 3'UTR of the arc5-1 gene, (arc term 1197 bp; GenBank accession no. Z50202.1, SEQ ID NO: 21) (De Jaeger et al 2002). A linker (FM) comprising a chymosin cleavage site was inserted between the two proteins and a C-terminal KDEL (SEQ ID NO: 23) was also included for ER retention.

Para-κ-Casein-β-Lactoglobulin Fusion with Linker

Shown in FIG. 7 is an example expression cassette comprising para-κ-casein (paraOKC1-T, SEQ ID NO: 1) and β-lactoglobulin (OLG1, SEQ ID NO: 9). The regulatory sequences that were used in order to produce the heterologous milk proteins in soybean seeds include the promoter of the beta-phaseolin storage protein gene (PvPhas prom; −1 to −1543; GenBank accession no. J01263.1, SEQ ID NO: 18); the 5'UTR of the arc5-1 gene (arc5'UTR; −1 to −13; GenBank accession no. Z50202, SEQ ID NO: 20) (De Jaeger et al, 2002); the signal peptide of Lectin 1 gene 1 (sig10; +1 to +93; GenBank accession no. Glyma.02G012600, SEQ ID NO: 14) (Darnowski et al, 2002); and, the 3'UTR of the arc5-1 gene, (arc term 1197 bp; GenBank accession no. Z50202.1, SEQ ID NO: 21) (De Jaeger et al, 2002). A linker (FM) comprising a chymosin cleavage site was inserted between the two proteins.

Fusion Protein with Seed2 Promoter, Sig2 and Nopaline Synthase Terminator

Shown in FIG. 8 is an example expression cassette comprising κ-casein (OKC1-T, SEQ ID NO: 3) and β-lactoglobulin (OLG1, SEQ ID NO: 9). The regulatory sequences that were used in order to produce the heterologous milk proteins in soybean seeds include the promoter and signal peptide of glycinin 1 (GmSeed2 (SEQ ID NO: 19):sig2 (SEQ ID NO: 16)) followed by the ER retention signal (KDEL) and the Nopaline synthase termination sequence (nos term, SEQ ID NO: 22).

Example 2: Identification of Transgenic Events, Recombinant Protein Extraction and Detection To quantify recombinant protein expression levels, DNA constructs such as those shown in FIG. 3-8 were transformed into soybean using transformation protocols well known in the art, for example, by bombardment or *agrobacterium*. Total soybean genomic DNA was isolated from the first trifoliate leaves of transgenic events using the PureGene tissue DNA isolation kit (product #158667: QIAGEN, Valencia, Calif., USA). Trifoliates were frozen in liquid nitrogen and pulverized. Cells were lysed using the PureGene Cell Lysis Buffer, proteins were precipitated using the PureGene Protein Precipitation Buffer, and DNA was precipitated from the resulting supernatant using ethanol. The DNA pellets were washed with 70% ethanol and resuspended in water.

Genomic DNA was quantified by the Quant-iT PicoGreen (product #P7589: ThermoFisher Scientific, Waltham, Mass., USA) assay as described by manufacturer, and 150 ng of DNA was digested overnight with EcoRI, HindIII, NcoI, and/or KpnI, 30 ng of which was used for a BioRad ddPCR reaction, including labelled FAM or HEX probes for the transgene and Lectin1 endogenous gene respectively. Transgene copy number (CNV) was calculated by comparing the measured transgene concentration to the reference gene concentration. A CNV of greater than or equal to one was deemed acceptable.

Preparation of Total Soluble Protein Samples

Total soluble soybean protein fractions were prepared from the seeds of transgenic events by bead beating seeds (seeds collected about 90 days after germination) at 15000 rpm for 1 min. The resulting powder was resuspended in 50 mM Carbonate-Bicarbonate pH 10.8, 1 mM DTT, 1× HALT Protease Inhibitor Cocktail (Product #78438 ThermoFisher Scientific). The resuspended powder was incubated at 4° C. for 15 minutes and then the supernatant collected after centrifuging twice at 4000g, 20 min, 4° C. Protein concentration was measured using a modified Bradford assay (Thermo Scientific Pierce 660 nm assay; Product #22660 ThermoFisher Scientific) using a bovine serum albumin (BSA) standard curve.

Recombinant Protein Quantification Via Western Blot Densitometry

SDS-PAGE was performed according to manufacturer's instructions (Product #5678105BioRad, Hercules, Calif., USA) under denaturing and reducing conditions. 5 ug of total protein extracts were loaded per lane. For immunoblotting proteins separated by SDS-PAGE were transferred to a PVDF membrane using Trans-Blot® Turbo™ Midi PVDF Transfer Packs (Product #1704157 BioRad) according to manufacturer's guidelines. Membranes were blocked with 3% BSA in phosphate buffered saline with 0.5% Tween-20, reacted with antigen specific antibody and subsequently reacted with fluorescent goat anti rabbit IgG (Product #60871 BioRad, CA). Membranes were scanned according to manufacturer's instructions using the ChemiDoc MP Imaging System (BioRad, CA) and analyzed using Image-Lab Version 6.0.1 Standard Edition (BioRad Laboratories, Inc.). Recombinant protein from the seeds of transgenic events was quantified by densitometry from commercial reference protein spike-in standards.

Figures 9A, 9C:
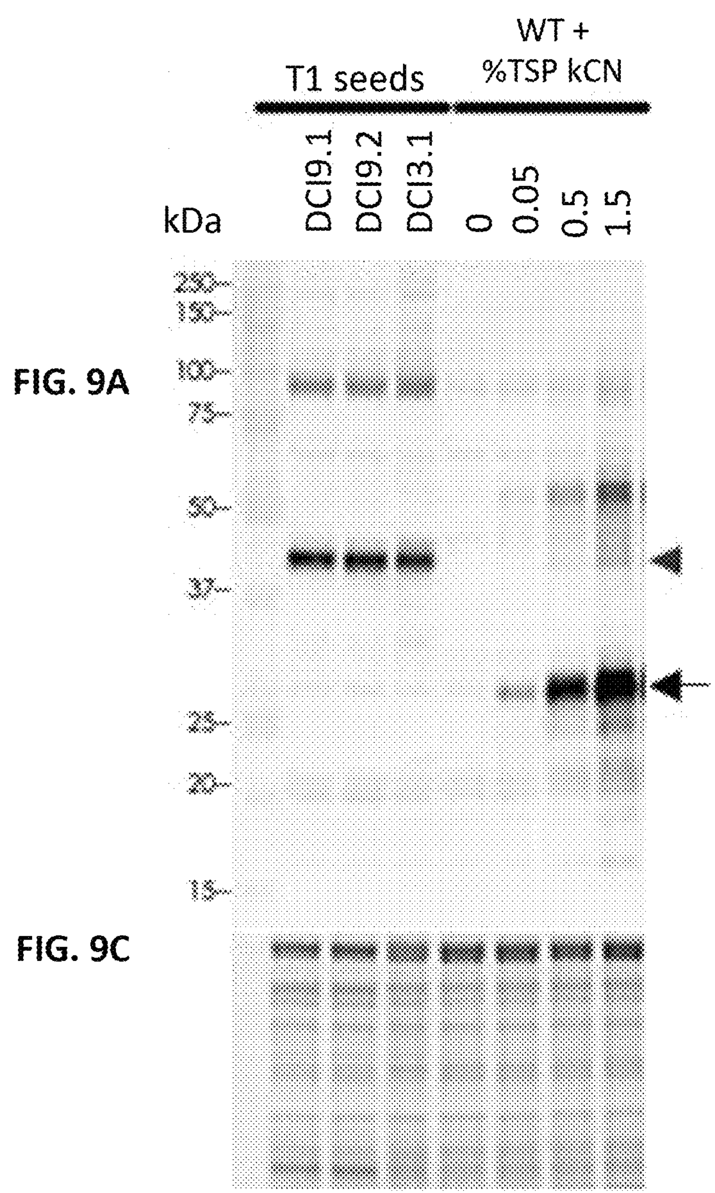
FIGS. 9A, 9B, 9C, and 9D show protein detection by western blotting.

Shown in FIGS. 9A, 9B, 9C, and 9D are Western Blots of protein extracted from transgenic soybeans expressing the κ-casein-β-lactoglobulin expression cassette shown in FIG. 3. FIG. 9A shows the fusion protein detected using a primary antibody raised against κ-casein. The first lane is a molecular weight marker. Lanes two (DCI 9.1) and three (DCI 9.2) represent individual seeds from a single transgenic line. Lane four (DCI 3.1) represents a seed from a separate transgenic line. Lane five is protein extracted from wild-type soybean plants, and lanes six-eight are protein extracted from wild-type soybean plants spiked with 0.05% commercial κ-casein (lane 6), 0.5% commercial κ-casein (lane 7), and 1.5% commercial κ-casein (lane 8). The κ-casein commercial protein is detected at an apparent molecular weight (MW) of ~26 kDa (theoretical: 19 kDa—arrow). The fusion protein is detected at an apparent MW of ~40 kDa (theoretical: 38 kDa—arrowhead).

Figures 9B, 9D:
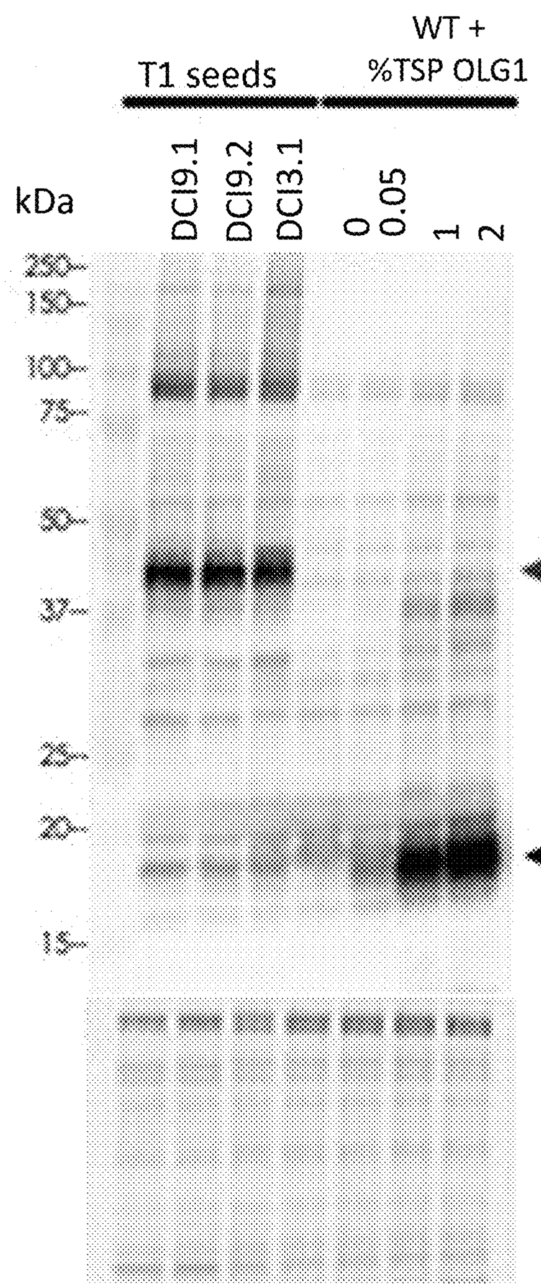
Figure 10A:
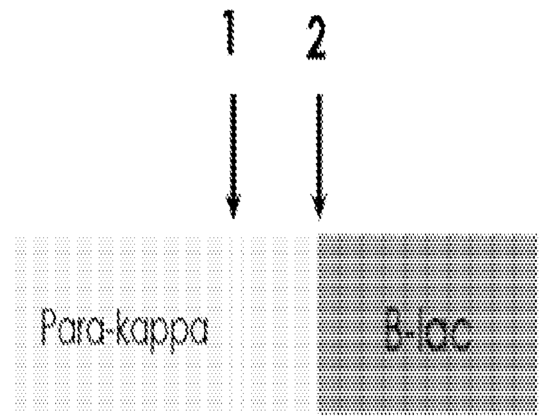
FIGS. 10A and 10B show two illustrative fusion proteins.
Figure 10B:
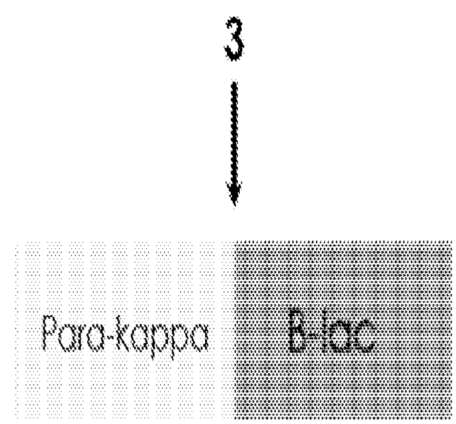

FIG. 9B shows the fusion protein detected using a primary antibody raised against β-lactoglobulin. The first lane is a molecular weight marker. Lanes two (DCI 9.1) and three (DCI 9.2) represent individual seeds from a single transgenic line. Lane four (DCI 3.1) represents a seed from a separate transgenic line. Lane five is protein extracted from wild-type soybean plants, and lanes six-eight are protein extracted from wild-type soybean plants spiked with 0.05% commercial β-lactoglobulin (lane 6), 1% commercial β-lactoglobulin (lane 7), and 2% commercial β-lactoglobulin (lane 8). The β-lactoglobulin commercial protein is detected at an apparent MW of ~18 kDa (theoretical: 18 kDa—arrow). The fusion protein is detected at an apparent MW of ~40 kDa (theoretical: 38 kDa—arrowhead). FIGS. 9C and 9D show the protein gels as control for equal lane loading (image is taken at the end of the SDS run) for FIGS. 9A and 9B, respectively.

Other combinations of structured and unstructured proteins were tested and evaluated for the percentage of recombinant protein. Cassettes having the same promoter (Seed2-sig), signal peptide (EUT:Rb7T), and in some instances a different terminator, were built with either α-S1-casein, β-casein, κ-casein, or the fusion of β-lactoglobulin with κ-casein (kCN-LG) (See FIGS. 3 and 8). As shown below in Table 3, none of the cassettes encoding α-S1-casein, β-casein, or κ-casein were able to produce expression of the protein at a level that exceeded 1% total soluble protein. However, when κ-casein was fused with β-lactoglobulin, κ-casein was expressed at a level that was greater than 1% total soluble protein.

TABLE 3

Expression levels of unstructured proteins

| | | Total events[1] analyzed | Number of events[1] accumulating the recombinant protein at the concentration: 0-1% TSP | Above 1% TSP |
|---|---|---|---|---|
| Unstructured | κ-Casein | 89 | 89 | 0 |
| | B-Casein | 12 | 12 | 0 |
| | αS1-Casein | 6 | 6 | 0 |
| Fusion | kCN-LG | 23 | 12 | 11 |

[1]As used in Table 3, the each "event" refers to an independent transgenic line.

As will be readily understood by those of skill in the art, T-DNA insertion into the plant genome is a random process and each T-DNA lands at an unpredictable genomic position. Hence, each of the 23 events generated in Table 3 for the fusion protein have different genomic insertion loci. The genomic context greatly influences the expression levels of a gene, and each loci will be either favorable or unfavorable for the expression of the recombinant genes. The variability observed at the protein level is a reflection of that random insertion process, and explains why 12 out of 23 events present expression levels below 1%.

Example 3: Food Compositions

The transgenic plants expressing the recombinant fusion proteins described herein can produce milk proteins for the purpose of food industrial, non-food industrial, pharmaceutical, and commercial uses described in this disclosure. An illustrative method for making a food composition is provided in FIG. 11.

A fusion protein comprising an unstructured milk protein (para-κ-casein) and a structured mammalian protein (β-lactoglobulin) is expressed in a transgenic soybean plant. The fusion protein comprises a chymosin cleavage site between the para-κ-casein and the β-lactoglobulin.

The fusion protein is extracted from the plant. The fusion protein is then treated with chymosin, to separate the para-κ-casein from the β-lactoglobulin. The para-κ-casein is isolated and/or purified and used to make a food composition (e.g., cheese).

Numbered Embodiments

Notwithstanding the appended claims, the following numbered embodiments also form part of the instant disclosure.

1. A stably transformed plant comprising in its genome: a recombinant DNA construct encoding a fusion protein, the fusion protein comprising: (i) an unstructured milk protein, and (ii) a structured animal protein; wherein the fusion protein is stably expressed in the plant in an amount of 1% or higher per total protein weight of soluble protein extractable from the plant.

2. The stably transformed plant of embodiment 1, wherein the fusion protein comprises, from N-terminus to C-terminus, the unstructured milk protein and the animal protein.

3. The stably transformed plant of any one of embodiments 1-2, wherein the unstructured milk protein is α-S1 casein, α-S2 casein, β-casein, or κ-casein.

4. The stably transformed plant of embodiment 1, wherein the unstructured milk protein is κ-casein and comprises the sequence of SEQ ID NO: 4, or a sequence at least 90% identical thereto.

5. The stably transformed plant of embodiment 1, wherein the unstructured milk protein is para-κ-casein and comprises the sequence of SEQ ID NO: 2, or a sequence at least 90% identical thereto.

6. The stably transformed plant of embodiment 1, wherein the unstructured milk protein is β-casein and comprises the sequence of SEQ ID NO: 6, or a sequence at least 90% identical thereto.

7. The stably transformed plant of embodiment 1, wherein the unstructured milk protein is α-S1 casein and comprises the sequence SEQ ID NO: 8, or a sequence at least 90% identical thereto.

8. The stably transformed plant of embodiment 1, wherein the unstructured milk protein is α-S2 casein and comprises the sequence SEQ ID NO: 84, or a sequence at least 90% identical thereto.

9. The stably transformed plant of any one of embodiments 1-8, wherein the structured animal protein is a structured mammalian protein.

10. The stably transformed plant of embodiment 9, wherein the structured mammalian protein is β-lactoglobulin, α-lactalbumin, albumin, lysozyme, lactoferrin, lactoperoxidase, hemoglobin, collagen, or an immunoglobulin.

11. The stably transformed plant of embodiment 9, wherein the structured mammalian protein is β-lactoglobulin and comprises the sequence of SEQ ID NO: 10, or a sequence at least 90% identical thereto.

12. The stably transformed plant of any one of embodiments 1-8, wherein the structured animal protein is a structured avian protein.

13. The stably transformed plant embodiment 12, wherein the structured avian protein is ovalbumin, ovotransferrin, lysozyme or ovoglobulin.

14. The stably transformed plant of embodiment 9, wherein the milk protein is κ-casein and the structured mammalian protein is β-lactoglobulin.

15. The stably transformed plant of embodiment 9, wherein the milk protein is para-κ-casein and the structured mammalian protein is β-lactoglobulin.

16. The stably transformed plant of embodiment 9, wherein the milk protein is β-casein and the structured mammalian protein is β-lactoglobulin.

17. The stably transformed plant of embodiment 9, wherein the milk protein is α-S1 casein or α-S2 casein and the structured mammalian protein is β-lactoglobulin.

18. The stably transformed plant of any one of embodiments 1-17, wherein the plant is a dicot.

19. The stably transformed plant of embodiment 18, wherein the dicot is *Arabidopsis*, tobacco, tomato, potato, sweet potato, cassava, alfalfa, lima bean, pea, chick pea, soybean, carrot, strawberry, lettuce, oak, maple, walnut, rose, mint, squash, daisy, *Quinoa*, buckwheat, mung bean, cow pea, lentil, lupin, peanut, fava bean, French beans (i.e., common beans), mustard, or cactus.

20. The stably transformed plant of any one of embodiments 1-19, wherein the plant is soybean.

21. The stably transformed plant of any one of embodiments 1-20, wherein the recombinant DNA construct is codon-optimized for expression in the plant.

22. The stably transformed plant of any one of embodiments 1-21, wherein the fusion protein comprises a protease cleavage site.

23. The stably transformed plant of embodiment 22, wherein the protease cleavage site is a chymosin cleavage site.

24. The stably transformed plant of any one of embodiments 1-23, wherein the fusion protein is expressed at a level at least 2-fold higher than an unstructured milk protein expressed individually in a plant.

25. The stably transformed plant of any one of embodiments 1-24, wherein the fusion protein accumulates in the plant at least 2-fold higher than an unstructured milk protein expressed without the structured animal protein.

26. A recombinant fusion protein comprising: (i) an unstructured milk protein, and (ii) a structured animal protein.

27. The recombinant fusion protein of embodiment 26, wherein the fusion protein is expressed in a plant.

28. The recombinant fusion protein of embodiment 26 or 27, wherein the unstructured milk protein is α-S1 casein, α-S2 casein, β-casein, or κ-casein.

29. The recombinant fusion protein of embodiment 28, wherein the milk protein is κ-casein and comprises the sequence of SEQ ID NO: 4, or a sequence at least 90% identical thereto.

30. The recombinant fusion protein of embodiment 28, wherein the milk protein is para-κ-casein and comprises the sequence of SEQ ID NO: 2, or a sequence at least 90% identical thereto.

31. The recombinant fusion protein of embodiment 28, wherein the milk protein is β-casein and comprises the sequence of SEQ ID NO: 6, or a sequence at least 90% identical thereto.

32. The recombinant fusion protein of embodiment 28, wherein the milk protein is α-S1 casein and comprises the sequence SEQ ID NO: 8, or a sequence at least 90% identical thereto.

33. The recombinant fusion protein of embodiment 28, wherein the milk protein is α-S2 casein and comprises the sequence SEQ ID NO: 84, or a sequence at least 90% identical thereto.

34. The recombinant fusion protein of any one of embodiments 26-33, wherein the structured animal protein is a structured mammalian protein.

35. The recombinant fusion protein of embodiment 34, wherein the structured mammalian protein is β-lactoglobulin, α-lactalbumin, albumin, lysozyme, lactoferrin, lactoperoxidase, hemoglobin, collagen, or an immunoglobulin.

36. The recombinant fusion protein of embodiment 34, wherein the structured mammalian protein is β-lactoglobulin and comprises the sequence of SEQ ID NO: 10, or a sequence at least 90% identical thereto.

37. The recombinant fusion protein of any one of embodiments 26-33, wherein the structured animal protein is a structured avian protein.

38. The recombinant fusion protein of embodiment 37, wherein the structured avian protein is ovalbumin, ovotransferrin, lysozyme or ovoglobulin.

39. The recombinant fusion protein embodiment 34, wherein the milk protein is κ-casein and the structured mammalian protein is β-lactoglobulin.

40. The recombinant fusion protein of embodiment 34, wherein the milk protein is para-κ-casein and the structured mammalian protein is β-lactoglobulin.

41. The recombinant fusion protein of embodiment 34, wherein the milk protein is β-casein and the structured mammalian protein is β-lactoglobulin.

42. The recombinant fusion protein of embodiment 34, wherein the milk protein is α-S1 casein or α-S2 casein and the structured mammalian protein is β-lactoglobulin.

43. The recombinant fusion protein of embodiment 34, wherein the fusion protein comprises a protease cleavage site.

44. The recombinant fusion protein of embodiment 34, wherein the protease cleavage site is a chymosin cleavage site.

45. A nucleic acid encoding the recombinant fusion protein of any one of embodiments 26 to 44.

46. The nucleic acid of embodiment 45, wherein the nucleic acid is codon optimized for expression in a plant species.

47. The nucleic of embodiment 45 or 46, wherein the nucleic acid is codon optimized for expression in soybean.

48. A vector comprising a nucleic acid encoding a recombinant fusion protein, wherein the recombinant fusion protein comprises: (i) an unstructured milk protein, and (ii) a structured animal protein.

49. The vector of embodiment 48, wherein the vector is a plasmid.

50. The vector of embodiment 49, wherein the vector is an *Agrobacterium* Ti plasmid.

51. The vector of any one of embodiments 48-50, wherein the nucleic acid comprises, in order from 5' to 3': a promoter; a 5' untranslated region; a sequence encoding the fusion protein; and a terminator.

52. The vector of embodiment 51, wherein the promoter is a seed-specific promoter.

53. The vector of embodiment 52, wherein the seed-specific promoter is selected from the group consisting of PvPhas, BnNap, AtOle1, GmSeed2, GmSeed3, GmSeed5, GmSeed6, GmSeed7, GmSeed8, GmSeed10, GmSeed11, GmSeed12, pBCON, GmCEP1-L, GmTHIC, GmBg7S1, GmGRD, GmOLEA, GmOLER, Gm2S-1, and GmBBld-II.

54. The vector of embodiment 53, wherein the seed-specific promoter is PvPhas and comprises the sequence of SEQ ID NO: 18, or a sequence at least 90% identical thereto.

55. The vector of embodiment 53, wherein the seed-specific promoter is GmSeed2 and comprises the sequence of SEQ ID NO: 19, or a sequence at least 90% identical thereto.

56. The vector of any one of embodiments 51-55, wherein the 5' untranslated region is selected from the group consisting of Arc5'UTR and glnB1UTR.

57. The vector of embodiment 56, wherein the 5' untranslated region is Arc5'UTR and comprises the sequence of SEQ ID NO: 20, or a sequence at least 90% identical thereto.

58. The vector of any one of embodiments 51-57, wherein the expression cassette comprises a 3' untranslated region.

59. The vector of embodiment 58, wherein the 3' untranslated region is Arc5-1 and comprises SEQ ID NO: 21, or a sequence at least 90% identical thereto.

60. The vector of any one of embodiments 51-59, wherein the terminator sequence is a terminator isolated or derived from a gene encoding Nopaline synthase, Arc5-1, an Extensin, Rb7 matrix attachment region, a Heat shock protein, Ubiquitin 10, Ubiquitin 3, and M6 matrix attachment region.

61. The vector of embodiment 60, wherein the terminator sequence is isolated or derived from a Nopaline synthase gene and comprises the sequence of SEQ ID NO: 22, or a sequence at least 90% identical thereto.

62. A plant comprising the recombinant fusion protein of any one of embodiments 26-44 or the nucleic acid of any one of embodiments 45-47.

63. A method for stably expressing a recombinant fusion protein in a plant, the method comprising: a) transforming a plant with a plant transformation vector comprising an expression cassette comprising: a sequence encoding a fusion protein, wherein the fusion protein comprises an unstructured milk protein, and a structured animal protein; and b) growing the transformed plant under conditions wherein the recombinant fusion protein is expressed in an amount of 1% or higher per total protein weight of soluble protein extractable from the plant.

64. The method of embodiment 63, wherein the unstructured milk protein is κ-casein.

65. The method of embodiment 63 or 64, wherein the structured animal protein is β-lactoglobulin.

66. A food composition comprising the recombinant fusion protein of any one of embodiments 26-44.

67. A method for making a food composition, the method comprising: expressing the recombinant fusion protein of any one of embodiments 26-44 in a plant; extracting the recombinant fusion protein from the plant; optionally, separating the milk protein from the structured animal protein or the structured plant protein; and creating a food composition using the milk protein or the fusion protein.

68. The method of embodiment 67, wherein the plant stably expresses the recombinant fusion protein.

69. The method of embodiment 68, wherein the plant expresses the recombinant fusion protein in an amount of 1% or higher per total protein weight of soluble protein extractable from the plant.

70. The method of any one of embodiments 67-69, wherein the plant is soybean.

71. The method of any one of embodiments 67-70, wherein the food composition comprises the structured animal or plant protein.

72. The method of any one of embodiments 67-71, wherein the milk protein and the structured animal or plant protein are separated from one another in the plant cell, prior to extraction.

73. The method of any one of embodiments 67-71, wherein the milk protein is separated from the structured animal or plant protein after extraction, by contacting the fusion protein with an enzyme that cleaves the fusion protein.

74. A food composition produced using the method of any one of embodiments 67-73.

75. A plant-expressed recombinant fusion protein, comprising: κ-casein; and β-lactoglobulin.

76. The plant-expressed recombinant fusion protein of embodiment 75, wherein the fusion protein comprises, in order from N-terminus to C-terminus, the κ-casein and the β-lactoglobulin.

77. The plant-expressed recombinant fusion protein of embodiment 75 or 76, wherein the fusion protein comprises a protease cleavage site.

78. The plant-expressed recombinant fusion protein of embodiment 77, wherein the protease cleavage site is a chymosin cleavage site.

79. The plant-expressed recombinant fusion protein of any one of embodiments 75-78, wherein the fusion protein comprises a signal peptide.

80. The plant-expressed recombinant fusion protein of embodiment 79, wherein the signal peptide is located at the N-terminus of the fusion protein.

81. The plant-expressed recombinant fusion protein of any one of embodiments 75-80, wherein the fusion protein is encoded by a nucleic acid that is codon optimized for expression in a plant.

82. The plant-expressed recombinant fusion protein of any one of embodiments 75-81, wherein the fusion protein is expressed in a soybean.

83. The plant-expressed recombinant fusion protein of any one of embodiments 75-81, wherein the fusion protein has a molecular weight of 30 kDa to 50 kDa.

84. The plant-expressed recombinant fusion protein of any one of embodiments 75-83, wherein the fusion protein is expressed in a plant in an amount of 1% or higher per total protein weight of soluble protein extractable from the plant.

85. The plant-expressed recombinant fusion protein of any one of embodiments 75-84, wherein the fusion protein is expressed in the plant at a level at least 2-fold higher than κ-casein expressed individually in a plant.

86. The plant-expressed recombinant fusion protein of any one of embodiments 75-84, wherein the fusion protein accumulates in the plant at least 2-fold higher than κ-casein expressed without β-lactoglobulin.

87. A stably transformed plant, comprising in its genome: a recombinant DNA construct encoding a fusion protein, the fusion protein comprising: κ-casein; and β-lactoglobulin; wherein the fusion protein is stably expressed in the plant in an amount of 1% or higher per total protein weight of soluble protein extractable from the plant.

88. The stably transformed plant of embodiment 87, wherein the fusion protein comprises, in order from N-terminus to C-terminus, the κ-casein and the β-lactoglobulin.

89. The stably transformed plant of embodiment 87 or 88, wherein the fusion protein comprises a protease cleavage site.

90. The stably transformed plant of embodiment 89, wherein the protease cleavage site is a chymosin cleavage site.

91. The stably transformed plant of any one of embodiments 87-90, wherein the fusion protein comprises a signal peptide.

92. The stably transformed plant of embodiment 91, wherein the signal peptide is located at the N-terminus of the fusion protein.

93. The stably transformed plant of any one of embodiments 87-92, wherein the plant is soybean.

94. The stably transformed plant of any one of embodiments 87-93, wherein the recombinant DNA construct comprises codon-optimized nucleic acids for expression in the plant.

95. The stably transformed plant of any one of embodiments 87-94, wherein the fusion protein has a molecular weight of 30 kDa to 50 kDa.

96. The stably transformed plant of any one of embodiments 87-95, wherein the fusion protein is expressed at a level at least 2-fold higher than κ-casein expressed individually in a plant.

97. The stably transformed plant of any one of embodiments 87-96, wherein the fusion protein accumulates in the plant at least 2-fold higher than κ-casein expressed without β-lactoglobulin.

98. A plant-expressed recombinant fusion protein comprising: a casein protein and β-lactoglobulin.

99. The plant-expressed recombinant fusion protein of embodiment 98, wherein the casein protein is α-S1 casein, α-S2 casein, β-casein, or κ-casein.

100. A stably transformed plant, comprising in its genome: a recombinant DNA construct encoding a fusion protein, the fusion protein comprising: a casein protein and β-lactoglobulin; wherein the fusion protein is stably expressed in the plant in an amount of 1% or higher per total protein weight of soluble protein extractable from the plant.

101. The stably transformed plant of embodiment 100, wherein the casein protein is α-S1 casein, α-S2 casein, β-casein, or κ-casein.

The invention claimed is:

1. A nucleic acid sequence encoding a recombinant fusion protein, said fusion protein comprising: i) a bovine casein component and ii) a bovine β-lactoglobulin component.

2. The nucleic acid sequence of claim 1, wherein the recombinant fusion protein comprises, in order from N-terminus to C-terminus, the bovine casein component and the bovine β-lactoglobulin component.

3. The nucleic acid sequence of claim 1, wherein the bovine casein component is κ-casein.

4. The nucleic acid sequence of claim 1, wherein the bovine casein component is β-casein.

5. The nucleic acid sequence of claim 1, wherein the recombinant fusion protein comprises a protease cleavage site.

6. The nucleic acid sequence of claim 1, wherein the recombinant fusion protein comprises a chymosin cleavage site.

7. The nucleic acid sequence of claim 1, wherein the recombinant fusion protein comprises a signal peptide.

8. The nucleic acid sequence of claim 1, wherein the recombinant fusion protein has a molecular weight of 30 kDa to 50 kDa.

9. The nucleic acid sequence of claim 1, wherein the nucleic acid sequence is codon optimized for expression in a plant.

10. The nucleic acid sequence of claim 1, wherein the nucleic acid sequence is codon optimized for expression in a *Glycine max* plant.

11. An expression cassette, comprising: the nucleic acid sequence of claim 1.

12. The expression cassette of claim 11, comprising: a nucleic acid regulatory sequence.

13. The expression cassette of claim 11, comprising: a promoter.

14. An expression vector, comprising: the expression cassette of claim 11.

15. A plant transformation vector, comprising: the expression cassette of claim 11.

16. A binary plant transformation vector, comprising: the expression cassette of claim 11.

* * * * *